United States Patent
Berg et al.

(10) Patent No.: US 8,030,050 B2
(45) Date of Patent: *Oct. 4, 2011

(54) **MODIFIED AMYLASES FROM *PSEUDOMONAS* SPECIES**

(75) Inventors: Casper Tune Berg, Vedbak (DK); Patrick Maria Franciscus Derkx, Tikøb (DK); Carol Fioresi, Redwood City, CA (US); Gijsbert Gerritse, Heerjansdam (NL); Anja Hemmingen Kellet-Smith, Copenhagen (DK); Karsten Matthias Kragh, Viby J (DK); Wei Liu, Palo Alto, CA (US); Andrew Shaw, San Francisco, CA (US); Bo Spange Sørensen, Skanderborg (DK); Charlotte Refdahl Thoudahl, Greve (DK)

(73) Assignee: Danisco A/S, Copenhagen (DK)

( * ) Notice: Subject to any disclaimer, the term of this patent is extended or adjusted under 35 U.S.C. 154(b) by 481 days.

This patent is subject to a terminal disclaimer.

(21) Appl. No.: 11/534,624

(22) Filed: Sep. 22, 2006

(65) Prior Publication Data

US 2008/0227173 A1    Sep. 18, 2008

Related U.S. Application Data

(63) Continuation-in-part of application No. PCT/GB2006/002513, filed on Jul. 7, 2006, and a continuation-in-part of application No. 11/483,220, filed on Jul. 7, 2006, now abandoned.

(60) Provisional application No. 60/697,302, filed on Jul. 7, 2005.

(51) Int. Cl.
| | |
|---|---|
| *C12N 9/28* | (2006.01) |
| *C12N 9/26* | (2006.01) |
| *C12N 9/24* | (2006.01) |
| *C12N 9/00* | (2006.01) |
| *C12P 21/06* | (2006.01) |
| *A21D 2/00* | (2006.01) |
| *A23C 9/12* | (2006.01) |
| *C07H 21/04* | (2006.01) |

(52) U.S. Cl. ........ 435/202; 435/201; 435/200; 435/183; 435/69.1; 426/20; 426/61; 536/23.2; 536/23.74

(58) Field of Classification Search .................. 435/202, 435/201, 200, 183, 69.1; 426/20, 61; 536/23.2, 536/23.74
See application file for complete search history.

(56) References Cited

U.S. PATENT DOCUMENTS

| | | | |
|---|---|---|---|
| 4,683,202 A | 7/1987 | Mullis | |
| 4,946,779 A | 8/1990 | Kameda et al. | |
| 5,204,254 A | 4/1993 | Schmid et al. | |
| 5,958,749 A | 9/1999 | Kubota et al. | |
| 5,989,169 A | 11/1999 | Svendsen et al. | |
| 6,162,628 A | 12/2000 | Cherry et al. | |
| 6,242,224 B1 | 6/2001 | Nakano et al. | |
| 6,667,065 B1 | 12/2003 | Kragh et al. | |
| 7,166,453 B2 | 1/2007 | Kragh et al. | |
| 7,371,552 B2 * | 5/2008 | Kragh et al. | .................. 435/202 |
| 2005/0059131 A1 | 3/2005 | Bisgard-Frantzen et al. | |
| 2005/0136524 A1 | 6/2005 | Kragh et al. | |
| 2005/0137111 A1 | 6/2005 | Kragh et al. | |
| 2006/0008888 A1 | 1/2006 | Kragh et al. | |
| 2006/0008890 A1 | 1/2006 | Kragh et al. | |
| 2006/0018997 A1 | 1/2006 | Kragh et al. | |
| 2006/0073583 A1 | 4/2006 | Kragh et al. | |
| 2007/0020727 A1 | 1/2007 | Berg et al. | |
| 2007/0020731 A1 | 1/2007 | Kragh et al. | |
| 2007/0072270 A1 | 3/2007 | Kragh et al. | |
| 2007/0141693 A1 | 6/2007 | Berg et al. | |
| 2008/0107773 A1 | 5/2008 | Kragh et al. | |
| 2008/0274531 A1 | 11/2008 | Berg et al. | |
| 2008/0292747 A1 | 11/2008 | Berg et al. | |

FOREIGN PATENT DOCUMENTS

| | | |
|---|---|---|
| EP | 120 693 | 3/1984 |
| EP | 0 494 233 | 1/1991 |
| EP | 0 412 607 | 2/1991 |
| EP | 0 298 645 | 6/1998 |
| JP | 6-279745 | 10/1994 |
| JP | 6-279746 | 10/1994 |
| JP | 8-205865 | 8/1996 |
| JP | 2000-245466 | 9/2000 |
| WO | WO 91/04669 | 4/1991 |
| WO | WO 99/23211 | 5/1999 |
| WO | WO 99/50399 | 10/1999 |

(Continued)

OTHER PUBLICATIONS

Zhou et al., Nucleotide sequence of the maltotetrahydrolase gene from *Pseudomonas saccharophila*. FEBS Lett., 1989, vol. 225 (1): 37-41.*

(Continued)

*Primary Examiner* — Ganapathirama Raghu
(74) *Attorney, Agent, or Firm* — Vedder Price P.C.; Thomas J. Kowalski; Smitha B. Uthaman

(57) ABSTRACT

The invention describes a PS4 variant polypeptide derivable from a parent polypeptide having amylase activity selected from the group consisting of: (a) a polypeptide comprising an amino acid mutation at each of positions 33, 34, 121, 134, 141, 146, 157, 161, 178, 179, 223, 229, 272, 303, 307, 309 and 334; (b) a polypeptide comprising an amino acid mutation at each of positions 33, 34, 121, 134, 141, 145, 146, 157, 178, 179, 223, 229, 272, 303, 307 and 334; (c) a polypeptide comprising an amino acid mutation at each of positions 33, 34, 121, 134, 141, 146, 157, 178, 179, 223, 229, 272, 303, 307, 309 and 334; and (d) a polypeptide comprising an amino acid mutation at each of positions 3, 33, 34, 70, 121, 134, 141, 146, 157, 178, 179, 223, 229, 272, 303, 307, 309 and 334; with reference to the position numbering of a *Pseudomonas saccharophilia* exoamylase sequence shown as SEQ ID NO: 1, uses of such a polypeptide as a food or feed additive, and nucleic acids encoding such.

30 Claims, 4 Drawing Sheets

FOREIGN PATENT DOCUMENTS

| | | |
|---|---|---|
| WO | WO 00/58447 | 10/2000 |
| WO | WO 01/04273 | 1/2001 |
| WO | WO 02/068589 | 9/2002 |
| WO | WO 2004/091544 | 10/2004 |
| WO | WO 2004/111217 | 12/2004 |
| WO | WO 2005/003339 | 1/2005 |
| WO | WO 2005/007818 | 1/2005 |
| WO | WO 2005/007867 | 1/2005 |
| WO | WO 2006/003461 | 1/2006 |

OTHER PUBLICATIONS

Broun et al., Catalytic plasticity of fatty acid modification enzymes underlying chemical diversity of plant lipids. Science, 1998, vol. 282: 1315-1317.*

Kisselev L., Polypeptide release factors in prokaryotes and eukaryotes: same function, different structure. Structure, 2002, vol. 10: 8-9.*

Seffernick et al., Melamine deaminase and Atrazine chlorohydrolase: 98 percent identical but functionally different. J. Bacteriol.,2001, vol. 183 (8): 2405-2410.*

Wishart et al., A single mutation converts a novel phosphotyrosine binding domain into a dual-specificity phosphatase. J. Biol. Chem., 1995, vol. 270(45): 26782-26785.*

Witkowski et al., Conversion of b-ketoacyl synthase to a Malonyl Decarboxylase by replacement of the active cysteine with glutamine. Biochemistry, 1999, vol. 38: 11643-11650.*

U.S. Appl. No. 11/887,977, filed Oct. 5, 2007, Berg et al.

U.S. Appl. No. 12/339,718, filed Dec. 19, 2008, Derkx et al.

PCT US04/21723, Jun. 21, 2007, International Search Report.

Yoshiyuki Takasaki, "Production of Maltohexaose by α-Amylase from *Bacillus circulans* G-6", Agric. Biol. Chem., vol. 46, No. 6, 1982, pp. 1539-1547.

Hajime Taniguchi et al., "Purification of *Baccillus circulans* F-2 Amylase and Its General Properties", Agric. Biol. Chem. vol. 47, No. 3, 1983, pp. 511-519.

Francis J. Bealin-Kelly et al., "The α-amylase of the caldoactive bacterium *Bacillus caldovelox*", Biochemical Society Transactions, vol. 18, No. 2, 1990, pp. 310-311.

William M. Fogarty et al., "A novel maltohexaose-forming α-amylase from *Bacillus caldovelox*: patterns and mechanisms of action", Appl Microbiol Biotechnol, 1991, vol. 36, pp. 184-189.

Narimasa Saito, "A Thermophilic Extracellular α-Amylase from *Baccilus licheniformis*", Archives of Biochemistry and Biophysics, vol. 155, 1973, pp. 290-298.

Hajime Taniguchi "Matohexaose-Producing Amylase of *Bacillus circulans* F-2" National Food Research Institute, 1991, pp. 111-124.

Altschul et al., 1990, J. Mol. Biol. 403-410 . "Basic Local Alignment Search Tool".

Bernfeld, Methods Enzymol., (1954), 1, 149-158. "Amylase, α and β."

Beucage S.L. et al.,(1981) Tetrahedron Letters 22, p. 1859-1869. "Deoxynucleoside Phosphoramidites-A New Class of Key Intermediates for Deoxypolynucleotide Synthesis".

Bradford, 1976, Anal. Biochem., 72, 248. "A Rapid and Senstitive Method for The Quantitation of Microgram Quantifes of Protein Utilizing the Principle of Protein-Dye Binding".

Caruthers MH et al., (1980) Nuc. Acids Res. Symp. Ser. 215-23. "New Chemical Methods for Synthesizing Polynucleotides."

Devereux et al., 1984, Nuc. Acids Research 12 p. 387. "A Comprehensive set of sequence analysis programs for the VAX".

Henrissat B, Bairoch A; Biochem. J., 316,695-696 (1996)) "Updating the sequence-based classification of glycosyl hydrolases."

Higgins DG & Sharp PM (1988), Gene 73(1),237-244. "CLUSTAL: a package for performing multiple sequence alignment on a microcomputer".

Horn T. et al., 1980, Nuc. Acids Resp. Symp. Ser. 225-232. "Synthesis of Oligonucleotides on Cellulose."

Horwell DC, Trends Biotechnol. (1995) 13(4),132-134. "The 'peptoid' approach to the design of non-peptide, small molecule agonists and antagonists of neuropeptides."

Matthes et al., (1984) EMBO J. 3, p. 801-805 "Simultaneous rapid chemical synthesis of over one hundred oligonucleotides on a microscale".

Morinaga et al., (Biotechnology (1984) 2, p. 646-649). "Improvement of Oligonucleotide-Directed Site-Specific Mutagenesis Using Double-Stranded Plasmid DNA".

Nelson and Long, Analytical Biochemistry, 1989, 180, p. 147-151. "A General Method of Site-Specific Mutagenesis Using a Modification of The Thermus aquaticus Polymerase Chain Reaction".

Saiki R K et al. (Science (1988) 239, pp. 487-491. "Primer-Directed Enzymatic Amplification of DNA with a Thermostable DNA polymerase".

Sarkar and Sommer (Biotechniques (1990), 8, p. 404-407. "The "Megaprimer" Method of Site-Directed Mutagenesis".

Yoshiyuki Sakano et al., "Purification and Properties of an exo-α-Amylase from *Pseudomonas stutze*", Agric. Biol. Chem., vol. 46, No. 3, 1982, pp. 639-646.

Yoshiyuki Takasaki et al., "Maltotetraose-producing Amylase from *Bacillus* sp. MG-4", Agric. Biol. Chem., vol. 55, No. 7, 1991, pp. 1715-1720.

Geneseq Database Accession No. ADW75735, A. Gemot, et al., Stutzeri Maltotetrahydrolase Mature Protein Seq ID 7, Apr. 7, 2005.

Geneseq Database Accession No. ADW73063, C. T. Berg, et al., Stutzeri Maltotetrahydrolase Protein Seq ID12, Apr. 7, 2005.

Geneseq Database Accession No. ADW75733, A. Gemot, et al., Saccharophilia Variant Maltotetrahydrolase Protein Seq ID 5, Apr. 7, 2005.

A.K. Chandra et al., "Production of Extracellular Thermostable α-Amylase by *Bacillus licheniformis*", J. Ferment. Technol. vol. 58, No. 1, 1980, pp. 1-10.

R.A.K. Srivastava et al., "Culture Conditions for Production of Thermostable Amylase by *Bacillus stearothermophilus*", Applied and Environmental Microbiology, Jul. 1986, pp. 179-184.

Veronique Planchot et al.., "Purification and characterization of extracellular alpha-amylase from *Aspergillus fumigatus*", Carbohydrate Research, vol. 272, 1995, pp. 97-109.

Ohnishi et al., "General Consideration for Conditions and Methods of Amylase Assay", Handbook of Amylases and Related Enzymes, The Amylase Research Society of Japan, 1988, pp. 10-14.

Kim L. Larsen et al., "Purification and characterization of cyclodextrin glycosyltransferase from *Paenibacillus* sp. F8", Carbohydrate Research, vol. 310, 1998, pp. 211-219.

Helmut Blum et al., "Improved silver staining of plant proteins, RNA and DNA in polyacrylamide gels", Electrophoresis, 1987, vol. 8, pp. 93-99.

Hidetsugu Fuwa, "A New Method for Microdetermination of Amylase Activity by the Use of Amylose as the Substrate", The Journal of Biochemistry, vol. 41, No. 5, 1954, pp. 583-603.

Akira Tsukamoto et al., "Nucleotide Sequence of the Maltohexaose-Producing Amylase Gene from an Alkalophilic *Bacillus* sp. #707 and Structural Similarity to Liquefying Type α-Amylase", Biochemical and Biophysical Research Communications, vol. 151, No. 1, Feb. 29, 1988, pp. 25-31.

Y.C. Lee, "Carbohydrate analyses with high-performance anion-exchange chromatography", Journal of Chromatography A., vol. 720, 1996, pp. 137-149.

Robert N. Ammeraal et al., "High-performance anion-exchange chromatography with pulsed amperometric detection of linear and branched glucose oligosaccharides", Carbohydrate Research, vol. 215, 1991, pp. 179-192.

Greg Winter et al., "Man-made antibodies", Nature, vol. 349, 1991, pp. 293-299.

Rosario Orlandi et al.., "Cloning immunoglobulin variable domains for expression by the polymerase chain reaction", Proc. Natl. Acad. Sci. USA, vol. 86, May 1989, pp. 3833-3837.

Shun-ichi Takeda et al., "Construction of chimaeric processed immunoglobulin genes containing mouse variable and human constant region sequences", Nature, vol. 314, Apr. 1985, 452-454.

Michael S. Neuberger, et al., "Recombinant antibodies possessing novel effector functions", Nature, vol. 312, Dec. 13, 1984, pp. 604-608.

Sherie L. Morrison et al., "Chimeric human antibody molecules: Mouse antigen-binding domains with human constant region domains", Proc. Natl. Acad. Sci. USA, vol. 81, Nov. 1984, pp. 6851-6855.

J. F. Kennedy et al., "Characteristics of alpha-Amylase K, a Novel Amylase from a Strain of *Bacillus subtilis*", Starch/Starke, vol. 31, No. 3, 1979, pp. 93-99.

Sambrook, J., E. F. Fritsch, and T. Maniatis, 1989, "Molecular Cloning: A Laboratory Manual", Second Edition, Books 1-3.

S.P.C. Cole et al., "The EBV-Hybridoma Technique and Its Application to Human Lung Cancer", Monoclonal Antibodies and Cancer Therapy, 1985, pp. 77-96.

Richard J. Cote, et al., "Generation of human monoclonal antibodies reactive with cellular antigens", Proc. Natl. Acad. Sci. USA, vol. 80, Apr. 1983, pp. 2026-2030.

Danuta Kozbor et al., "The production of monoclonal antibodies from human lymphocytes", Immunology Today, vol. 4, No. 3, 1983.

Kohler et al., Nature, vol. 256, 1975, pp. 495-497 "Continuous cultures of fused cells secreting antibody of predefined specificity."

M. Antoinette Mc Tigue et al., The alkaline amylase of the alkalophilic *Bacillus* sp. IMD 370, Department of Industrial Microbiology, vol. 17, 1995, pp. 570-573.

Takaya Hayashi et al., "Properties of new alkaline maltohexaose-forming amylases", Appl Microbiol Biotechnol, vol. 28, 1988, pp. 281-285.

Tae Un Kim et al., "Purification and Characterization of a Maltotetraose-Forming Alkaline αAmylase from an Alkalophilic *Bacillus* Strain, GM8901", Applied and Environmental Microbiology, Aug. 1995, pp. 3105-3112.

Keiji Kainuma et al., "Isolation and Action Pattern of Maltohexaose Producing Amylase From *Aerobacter Aerogenes*", FEBS Letters, vol. 26, No. 1, Oct. 1972, pp. 281-285.

Claus Christophersen et al., "Enzymatic Characterizatoin of Novamyl a Thermostable α-Amylase", 1998, Starch/Starke, vol. 50, No. 1, pp. 39-45.

Byoung-Cheol Min et al., "Cloning of Novel Maltooligosaccharide-Producing Amylases as Antistaling Agents for Bread", J. Agric. Food Chem., 1998, vol. 46, pp. 779-782.

Tadeusz Jakubezyk et al., "Scientific Transactions of the Academy of Agriculture in Warsaw", Agricultural and Food Technology, vol. 8, 1973, pp. 223-235.

Jianhua Zhou et al., "Properties of the enzyme expressed by the *Pseudomonas saccharophila* maltotetraohydrolase gene (*mta*) in *Escherichia coli*", Carbohydrate Research, vol. 223, 1992, pp. 255-261.

Mitsuru Monma et al. "Formation and Hydrolysis of Maltohexaose by an Extracellular Exo-maltohexaohydrolase", Agric. Biol. Chem., vol. 47, No. 8, 1983, pp. 1769-1774.

William M. Fogarty et al., "Extracellular Maltotetraose-Forming Amylase of *Pseudomonas* SP". IMD 353, Biotechnology Letters, vol. 16, No. 5, May 1994, pp. 473-478.

Katsuo Wako et al., "Purification and Some Properties of a Maltotriose-producing Amylase", J. Jap. Soc. Starch Sci., vol. 26, No. 3, 1979, pp. 175-181.

Yoshiyuki Takasaki, "An Amylase Producing Maltotriose from *Bacillus subtilis*", Agric. Biol. Chem., vol. 49, No. 4, 1985, pp. 1091-1097.

E. Ann MacGregor, "Relationship of Sequence and Structure to Specificity in the α-amylase family of Enzymes", Biochimica et Biphysica Acta 1546 (2001) p. 1-20.

Simon RJ et al. *PNAS* (1992) 89(20), 9367-9371. "Peptoids: A Modular approach to drug discovery".

Smith et al., 1988, Gene 70, 351-361. "Characterization of signal-sequence-coding regions selected from the *Bacillus subtilis* chromosome".

Tatusova, T. FEMS Microbiol Lett 1999 174(2): 247-50. "BLAST 2 sequences, a new tool for comparing protein and nucleotide sequences".

Tatusova, T. FEMS Microbiol Lett 1999 177(1): 187-188. Erratum to "BLAST 2 Sequences, a new tool for comparing protein and nucleotide sequences".

Taylor W.R. (1986) "The classification of amino acid conservation" *J. Theor.Biol.* 119; 205-218.

Fujita et al. "Cloning and Nucleotide Sequence of the Gene (amyP) for Maltotetraose-Forming Amylase from *Pseudomonas stutzeri* MO-19," *J. Bactrol.* 1989, 171, 1333-1339.

Van der Maarel et al., "Properties and applications of starch-converting enzymes of the beta-amylase family," *J. of Biotechnology*, 94 (2002) pp. 137-155.

Ausubel et al., 1999, "Short Protocols in Molecular Biology", pp. 7-58 to 7-60.

Ausubel, F. M. et al. Cold Spring Harbor Laboratory Press; (1995 and periodic supplements).

Ed Harlow and David Lane "Antibodies, A Laboratory Manual", Cold Spring Harbor Laboratory Press, ISBN 0-87969-314-2, 1988.

Roskams, Jane and Linda Rodgers, "Lab Ref: A Handbook of Recipes, Reagents, and Other Reference Tools for Use at the Bench", Cold Spring Harbor Laboratory, ISBN 0-87969-630-3, 2002.

Larsson, Lars-Inge "Immunocytochemistry: Theory and Practice", CRC Press inc., Baca Raton, Florida, 1988, ISBN 0-8493-6078-1.

Seethala, Ramakrishna; Prabhavathi B. Fernandes, "Handbook of Drug Screening" vol. 114, Marcel Dekker, 2001, New York, NY, ISBN 0-8247-0562-9.

Harlow, Ed, "Using Antibodies: A Laboratory Manual",1988.

Lane, David; Ed Harlow, "Using Antibodies: A Laboratory Manual: Portable Protocol No. I" (1998, Cold Spring Harbor Laboratory Press, ISBN 0-87969-544-7).

Lilley, D. M. J. and J. E. Dahlberg, 1992, "Oligonucleotide Synthesis: A Practical Approach", IRL Press.

Polak, J. M. and James O'D. McGee, 1990, "In Situ Hybridization: Principles and Practice".

Pound John D. (ed); "Immunochemical Protocols, vol. 80", in the series: "Methods in Molecular Biology", Humana Press, Totowa, New Jersey, 1998.

Roe, B., Crabtree, J., and A. Kahn, "Current Protocols in Molecular Biology", ch. 9, 13, and 16, John Wiley & Sons, New York, N.Y., 1996.

Seethala, Ramakrishna; Prabhavathi B. Fernandes, "Handbook of Drug Screening", 1998, ISBN 0-89603-493-3.

Hisashi Okemoto et al., "Isolation and cultivation of a novel microorganism producing a maltopentaose-forming enzyme", Appl Microbiol Biotechnol, 1986, vol. 25, pp. 137-142.

William M. Fogarty, Department of Industrial Microbiology, University College, Dublin, Ireland, "Microbial Amylases", 1983, W.M Fogarty (Ed.) Microbial Enzymes and biotechnology, Applied Science, London, pp. 1-92.

William M. Fogarty et al., "Starch-Degrading Enzymes of Microbial Origin", Progress in Industrial Microbiology, vol. 15, M.J. Bull (Ed), Elsevier Scientific, 1979, pp. 87-150.

Keiji Kainuma et al., "Purification and some properties of a novel Maltohexaose-Producing Exo-Amylase From *Aerobacter aerogenes*", Biochimica et Biophysica Acta, 410 (1975) 333-346.

Osamu Shida et al., "Cloning and Nucleotide Sequence of the Maltopentaose-forming Amylase Gene from *Pseudomonas* sp. KO-8940", Biosci. Biotech. Biochem. vol. 56, No. 1, pp. 76-80, 1992.

UniProt database Accession No. P22963, Glucan 1,4-alpha-maltotetraohydrolase, Aug. 1, 1991.

GenomeNet 1GCY, Aug. 14, 2000, High Resolution Crystal Structure Of Maltotetraose-Forming Exo-Amylase.

Damien Devos, et al., Practical Limits Of Function Prediction, Proteins: Structure, Function, and Genetics (2000) vol. 41, p. 98-107.

S. Sen, et al., Developments In Directed Evolution For Improving Enzyme Functions, Applied Biochemistry and Biotechnology (2007) vol. 143, p. 212-223.

James C. Whisstock, et al., Prediction Of Protein Function From Protein Sequence And Structure, Quarterly Reviews of Biophysics (2003) vol. 36, No. 3, p. 307-340.

\* cited by examiner

SEQUENCE LISTING

<160> NUMBER OF SEQ ID NOS: 42

<210> SEQ ID NO 1
<211> LENGTH: 530
<212> TYPE: PRT
<213> ORGANISM: Pseudomonas saccharophila

<400> SEQUENCE: 1

```
Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
    130                 135                 140

Asn Tyr Pro Asn Asp Cys Asp Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175
```

```
Glu Leu Ala Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Gly Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly Glu Gly Gly
            420                 425                 430

Leu Val Asn Val Asn Phe Arg Cys Asp Asn Gly Val Thr Gln Met Gly
        435                 440                 445

Asp Ser Val Tyr Ala Val Gly Asn Val Ser Gln Leu Gly Asn Trp Ser
    450                 455                 460

Pro Ala Ser Ala Val Arg Leu Thr Asp Thr Ser Ser Tyr Pro Thr Trp
465                 470                 475                 480

Lys Gly Ser Ile Ala Leu Pro Asp Gly Gln Asn Val Glu Trp Lys Cys
                485                 490                 495

Leu Ile Arg Asn Glu Ala Asp Ala Thr Leu Val Arg Gln Trp Gln Ser
            500                 505                 510

Gly Gly Asn Asn Gln Val Gln Ala Ala Gly Ala Ser Thr Ser Gly
        515                 520                 525

Ser Phe
    530

<210> SEQ ID NO 2
<211> LENGTH: 429
<212> TYPE: PRT
<213> ORGANISM: Pseudomonas saccharophila

<400> SEQUENCE: 2

Asp Gln Ala Gly Lys Ser Pro Ala Gly Val Arg Tyr His Gly Gly Asp
1               5                   10                  15
```

```
Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
50                  55                  60

Ser Trp Thr Asp Pro Gly Lys Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
            420                 425
```

<210> SEQ ID NO 3

```
<211> LENGTH: 429
<212> TYPE: PRT
<213> ORGANISM: Pseudomonas saccharophila

<400> SEQUENCE: 3

Asp Gln Ala Gly Lys Ser Pro Ala Gly Val Arg Tyr His Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Pro Gly Arg Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400
```

```
Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
            420                 425

<210> SEQ ID NO 4
<211> LENGTH: 429
<212> TYPE: PRT
<213> ORGANISM: Pseudomonas saccharophila

<400> SEQUENCE: 4

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Pro Gly Arg Ser Gly Gly Gly Glu Gly Tyr Phe Trp
65                  70                  75                  80

His Asp Phe Asn Lys Asn Ser Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350
```

```
Arg Thr Ala Gly Val Arg Ala Asp Ser Ala Ile Ser Phe His Ser Gly
            355                 360                 365
Tyr Ser Gly Leu Val Ala Thr Val Ser Gly Ser Gln Gln Thr Leu Val
        370                 375                 380
Val Ala Leu Asn Ser Asp Leu Ala Asn Pro Gly Gln Val Ala Ser Gly
385                 390                 395                 400
Ser Phe Ser Glu Ala Val Asn Ala Ser Asn Gly Gln Val Arg Val Trp
                405                 410                 415
Arg Ser Gly Ser Gly Asp Gly Gly Asn Asp Gly Gly
            420                 425

<210> SEQ ID NO 5
<211> LENGTH: 551
<212> TYPE: PRT
<213> ORGANISM: Pseudomonas saccharophila

<400> SEQUENCE: 5

Met Ser His Ile Leu Arg Ala Ala Val Leu Ala Ala Val Leu Leu Pro
1               5                   10                  15
Phe Pro Ala Leu Ala Asp Gln Ala Gly Lys Ser Pro Ala Gly Val Arg
            20                  25                  30
Tyr His Gly Gly Asp Glu Ile Ile Leu Gln Gly Phe His Trp Asn Val
        35                  40                  45
Val Arg Glu Ala Pro Asn Asp Trp Tyr Asn Ile Leu Arg Gln Gln Ala
    50                  55                  60
Ser Thr Ile Ala Ala Asp Gly Phe Ser Ala Ile Trp Met Pro Val Pro
65                  70                  75                  80
Trp Arg Asp Phe Ser Ser Trp Thr Asp Gly Gly Lys Ser Gly Gly Gly
                85                  90                  95
Glu Gly Tyr Phe Trp His Asp Phe Asn Lys Asn Gly Arg Tyr Gly Ser
            100                 105                 110
Asp Ala Gln Leu Arg Gln Ala Ala Gly Ala Leu Gly Gly Ala Gly Val
        115                 120                 125
Lys Val Leu Tyr Asp Val Val Pro Asn His Met Asn Arg Gly Tyr Pro
    130                 135                 140
Asp Lys Glu Ile Asn Leu Pro Ala Gly Gln Gly Phe Trp Arg Asn Asp
145                 150                 155                 160
Cys Ala Asp Pro Gly Asn Tyr Pro Asn Asp Cys Asp Asp Gly Asp Arg
                165                 170                 175
Phe Ile Gly Gly Glu Ser Asp Leu Asn Thr Gly His Pro Gln Ile Tyr
            180                 185                 190
Gly Met Phe Arg Asp Glu Leu Ala Asn Leu Arg Ser Gly Tyr Gly Ala
        195                 200                 205
Gly Gly Phe Arg Phe Asp Phe Val Arg Gly Tyr Ala Pro Glu Arg Val
    210                 215                 220
Asp Ser Trp Met Ser Asp Ser Ala Asp Ser Ser Phe Cys Val Gly Glu
225                 230                 235                 240
Leu Trp Lys Gly Pro Ser Glu Tyr Pro Ser Trp Asp Trp Arg Asn Thr
                245                 250                 255
Ala Ser Trp Gln Gln Ile Ile Lys Asp Trp Ser Asp Arg Ala Lys Cys
            260                 265                 270
Pro Val Phe Asp Phe Ala Leu Lys Glu Arg Met Gln Asn Gly Ser Val
        275                 280                 285
Ala Asp Trp Lys His Gly Leu Asn Gly Asn Pro Asp Pro Arg Trp Arg
    290                 295                 300
```

```
Glu Val Ala Val Thr Phe Val Asp Asn His Asp Thr Gly Tyr Ser Pro
305                 310                 315                 320

Gly Gln Asn Gly Gly Gln His His Trp Ala Leu Gln Asp Gly Leu Ile
            325                 330                 335

Arg Gln Ala Tyr Ala Tyr Ile Leu Thr Ser Pro Gly Thr Pro Val Val
        340                 345                 350

Tyr Trp Ser His Met Tyr Asp Trp Gly Tyr Gly Asp Phe Ile Arg Gln
    355                 360                 365

Leu Ile Gln Val Arg Arg Thr Ala Gly Val Arg Ala Asp Ser Ala Ile
370                 375                 380

Ser Phe His Ser Gly Tyr Ser Gly Leu Val Ala Thr Val Ser Gly Ser
385                 390                 395                 400

Gln Gln Thr Leu Val Ala Leu Asn Ser Asp Leu Ala Asn Pro Gly
            405                 410                 415

Gln Val Ala Ser Gly Ser Phe Ser Glu Ala Val Asn Ala Ser Asn Gly
        420                 425                 430

Gln Val Arg Val Trp Arg Ser Ser Gly Asp Gly Gly Asn Asp
    435                 440                 445

Gly Gly Glu Gly Gly Leu Val Asn Val Asn Phe Arg Cys Asp Asn Gly
450                 455                 460

Val Thr Gln Met Gly Asp Ser Val Tyr Ala Val Gly Asn Val Ser Gln
465                 470                 475                 480

Leu Gly Asn Trp Ser Pro Ala Ser Ala Val Arg Leu Thr Asp Thr Ser
            485                 490                 495

Ser Tyr Pro Thr Trp Lys Gly Ser Ile Ala Leu Pro Asp Gly Gln Asn
        500                 505                 510

Val Glu Trp Lys Cys Leu Ile Arg Asn Glu Ala Asp Ala Thr Leu Val
    515                 520                 525

Arg Gln Trp Gln Ser Gly Gly Asn Asn Gln Val Gln Ala Ala Ala Gly
    530                 535                 540

Ala Ser Thr Ser Gly Ser Phe
545                 550

<210> SEQ ID NO 6
<211> LENGTH: 3050
<212> TYPE: DNA
<213> ORGANISM: Pseudomonas saccharophila

<400> SEQUENCE: 6
gatcggcgta ggtttcgcat tcgttgccca ggcgatattt cgccggtgcg ccagcagcct        60
ggaagcaggc ctggtcgccg ccgccggccg tggcgccgac gcccgaacgc agatagccgt       120
ggaaatcgac cgccagggcc gggccgccga ccagcagggc ggcaagcagg caggcgggtt       180
ttaggacgaa caggggggtgc gcggtgtgct tcatgacgag gtccttgttt ttcttgttaa      240
tgccgaatcg atcacgcctt cgctgcgtgt cgcagggcgc agctcggtgg cgaaagcctc       300
ggggatggct ccgctggcgg catcctcccg accagagatt cgctggcgc agctcgaggg       360 cgtaatcagg atgagtgcgg cgtaatccct ggggtgcggc tacgcccggc agggcgcaga      420
tgattgccag gggccttcgg cctggccact acgccgcctg caactggcg ggggaggttg       480 gtggtcgggg cgtgcagggg cagctgcgg gtgccggtcg aagacccggc cggcgttcat       540
cctcgtccgg cggccttgcc gtaggatacc cgaacaagca caagaaccgg agtattgcga       600
tgagccacat cctgcgtgcc gccgtattgg cggcggtcct gctgccgttt ccgcactgg       660 ccgatcaggc cggcaagagc ccggccgggg tgcgctacca cggcggcgac gaaatcatcc       720
```

```
tccagggctt ccactggaac gtcgtccgcg aagcgcccaa cgactggtac aacatcctcc    780
gccaacaggc ctcgacgatc gcggccgacg gcttctcggc aatctggatg ccggtgccct    840
ggcgtgactt ctccagctgg accgacggcg gcaagtccgg cggcggcgaa ggctacttct    900
ggcacgactt caacaagaac ggccgctacg gcagcgacgc ccagctgcgc caggccgccg    960
gcgcactcgg tggcgccggg gtgaaggtgc tctacgatgt ggtgcccaat cacatgaacc   1020
gcggctaccc ggacaaggag atcaacctgc cggccggcca gggcttctgg cgcaacgact   1080
gcgccgaccc gggcaactac cccaacgact gcgacgacgg tgaccgcttc atcggcggcg   1140
agtcggacct gaacaccggc catccgcaga tttacggcat gtttcgcgac gagcttgcca   1200
acctgcgcag cggctacggc gccggcggct tccgcttcga cttcgttcgc ggctatgcgc   1260
ccgagcgggt cgacagctgg atgagcgaca cgccgacga cagcttctgc gttggcgagc   1320
tgtggaaagg cccttctgaa tatccgagct gggactggcg caacacggcg agctggcagc   1380
agatcatcaa ggactggtcc gaccgggcca agtgcccggt gttcgacttc gctctcaagg   1440
agcgcatgca gaacggctcg gtcgccgact ggaagcatgg cctcaatggc aaccccgacc   1500
cgcgctggcg cgaggtggcg gtgaccttcg tcgacaacca cgacaccggc tattcgcccg   1560
ggcagaacgg cggccagcac cactgggcgc tgcaggacgg gctgatccgc caggcctacg   1620
cctacatcct caccagcccg ggcacgccgg tggtgtactg gtcgcacatg tacgactggg   1680
gctacggcga cttcatccgc cagctgatcc aggtgcggcg caccgccggc gtgcgcgccg   1740
attcggcgat cagcttccat agcggctaca gcggtctggt cgctaccgtc agcggcagcc   1800
agcagaccct ggtggtggcg ctcaactccg atctggccaa ccccggccag gttgccagcg   1860
gcagcttcag cgaggcggtc aacgccagca acggccaggt gcgcgtctgg cgcagcggta   1920
gcggcgatgg cggcgggaat gacggcggcg agggtggctt ggtcaatgtg aactttcgct   1980
gcgacaacgg cgtgacgcag atgggcgaca cgtctacgc ggtgggcaac gtcagccagc   2040
tcggcaactg gagcccggcc tccgcggtac ggctgaccga caccagcagc tatccgacct   2100
ggaagggcag catcgccctg cctgacggtc agaacgtgga atggaagtgc ctgatccgca   2160
acgaggcgga cgcgacgctg gtgcgtcagt ggcaatcggg cggcaacaac caggtccagg   2220
ccgccgccgg cgcgagcacc agcggctcgt tctgacgaca tgcccgcccg gcctcggcta   2280
cgcctacgcc gggcggctcc tcccgaccca gggtgggcag ggaggaggcc ggcgacgggc   2340
cgggccgccg atgctggcac gacaaccata aaagccttcg cgctgcgctg tcgtatcagg   2400
agctgttcat gttggcccag acccgctcga ccccttccg gcttggcttc ctggcccggc   2460
tgtacctgct gatcgccgca ctggtggcct tgctgatgct ggtagccggc accagcctgg   2520
ttgccatcgg ccgcctgcaa ggcaatgccg agcaaatctc gtcgaccgcg tcgcgtctgc   2580
tggtcagcga gagcttcttc ggtacgttgc agagcctgac gcagaacctg tccgacgccc   2640
tggccgagga ccggcctgac cagctcgacg gctatgtcgg ccggcatcgc acgctgcagg   2700
accaggccct cgagctgttc gcccagctgg agcgggtgac gccggacat gccgagacca   2760
agcaagcctg gcggcgctgt tgccggagct cgaccgccgc agcctggcgc tgatcgatgc   2820
gcacgcgacc tgctcgcgcg tggggcgcaa cgccgtcgcc tgcgcgatct gcagctgcag   2880
ttctcgcggc tcaagcagga cctgctgcag gcgcagttcg tgacgggcga cgagctggtc   2940
gcctattcca tcaagcagtt catcatcccg ctcgagcagg tcgagcgctg ctgttcgatg   3000
ccatcggcgt gtcttcgatc aaggcactcg atgaagcggg tgcgcagatc              3050
```

<210> SEQ ID NO 7
<211> LENGTH: 527
<212> TYPE: PRT
<213> ORGANISM: Pseudomonas stutzeri

<400> SEQUENCE: 7

```
Asp Gln Ala Gly Lys Ser Pro Asn Ala Val Arg Tyr His Gly Gly Asp
1               5                   10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ala Thr Ile Ala Ala
        35                  40                  45

Asp Gly Phe Ser Ala Ile Trp Met Pro Val Pro Trp Arg Asp Phe Ser
    50                  55                  60

Ser Trp Ser Asp Gly Ser Lys Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Ser Ala Leu Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
    130                 135                 140

Asn Tyr Pro Asn Asp Cys Asp Asp Gly Asp Arg Phe Ile Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Gly Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
```

```
                385                 390                 395                 400
Ser Phe Ser Glu Ala Val Asn Ala Ser Asn Gly Gln Val Arg Val Trp
                    405                 410                 415

Arg Ser Gly Thr Gly Ser Gly Gly Glu Pro Gly Ala Leu Val Ser
            420                 425                 430

Val Ser Phe Arg Cys Asp Asn Gly Ala Thr Gln Met Gly Asp Ser Val
            435                 440                 445

Tyr Ala Val Gly Asn Val Ser Gln Leu Gly Asn Trp Ser Pro Ala Ala
        450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525

<210> SEQ ID NO 8
<211> LENGTH: 527
<212> TYPE: PRT
<213> ORGANISM: Pseudomonas stutzeri

<400> SEQUENCE: 8

Asp Gln Ala Gly Lys Ser Pro Asn Ala Val Arg Tyr His Gly Gly Asp
1               5                   10                  15

Glu Ile Ile Leu Gln Gly Phe His Trp Asn Val Val Arg Glu Ala Pro
                20                  25                  30

Tyr Asn Trp Tyr Asn Ile Leu Arg Gln Gln Ala Ala Thr Ile Ala Ala
            35                  40                  45

Asp Gly Phe Ser Ala Ile Trp Met Pro Val Pro Trp Arg Asp Phe Ser
        50                  55                  60

Ser Trp Ser Asp Pro Ser Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ser Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
```

```
                    245                 250                 255
Ala Leu Lys Glu Arg Met Gln Asn Gly Ser Ile Ala Asp Trp Lys His
                260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
        290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
                370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
                450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525

<210> SEQ ID NO 9
<211> LENGTH: 527
<212> TYPE: PRT
<213> ORGANISM: Pseudomonas stutzeri

<400> SEQUENCE: 9

Asp Gln Ala Gly Lys Ser Pro Asn Ala Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ala Thr Ile Ala Ala
        35                  40                  45

Asp Gly Phe Ser Ala Ile Trp Met Pro Val Pro Trp Arg Asp Phe Ser
    50                  55                  60

Ser Trp Ser Asp Pro Ser Arg Ser Gly Gly Glu Tyr Phe Trp
65                  70                  75                  80

His Asp Phe Asn Lys Asn Gly Arg Tyr Gly Ser Asp Ala Gln Leu Arg
                85                  90                  95

Gln Ala Ala Ser Ala Leu Gly Gly Ala Gly Val Lys Val Leu Tyr Asp
```

```
                  100             105             110
Val Val Pro Asn His Met Asn Arg Asp Tyr Pro Asp Lys Glu Ile Asn
            115                 120             125
Leu Pro Ala Gly Gln Arg Phe Trp Arg Asn Asp Cys Pro Asp Pro Gly
        130                 135             140
Asn Tyr Pro Asn Asp Cys Asp Gly Asp Arg Phe Leu Gly Gly Asp
145                 150                 155             160
Ala Asp Leu Asn Thr Gly His Pro Gln Val Tyr Gly Met Phe Arg Asp
                165                 170             175
Glu Phe Thr Asn Leu Arg Ser Gln Tyr Gly Ala Gly Gly Phe Arg Phe
            180                 185             190
Asp Phe Val Arg Gly Tyr Ala Pro Glu Arg Val Asn Ser Trp Met Thr
        195                 200             205
Asp Ser Ala Asp Asn Ser Phe Cys Val Gly Glu Leu Trp Lys Ala Pro
    210                 215             220
Ser Glu Tyr Pro Asn Trp Asp Trp Arg Asn Thr Ala Ser Trp Gln Gln
225                 230                 235             240
Ile Ile Lys Asp Trp Ser Asp Arg Ala Lys Cys Pro Val Phe Asp Phe
                245                 250             255
Ala Leu Lys Glu Arg Met Gln Asn Gly Ser Ile Ala Asp Trp Lys His
            260                 265             270
Gly Leu Asn Gly Asn Pro Asp Pro Arg Trp Arg Glu Val Ala Val Thr
        275                 280             285
Phe Val Asp Asn His Asp Thr Gly Tyr Ser Pro Gly Gln Asn Gly Gly
        290                 295             300
Gln His Leu Trp Ala Leu Gln Asp Gly Leu Ile Arg Gln Ala Tyr Ala
305                 310                 315             320
Tyr Ile Leu Thr Ser Pro Gly Thr Pro Val Val Tyr Trp Pro His Met
                325                 330             335
Tyr Asp Trp Gly Tyr Gly Glu Phe Ile Arg Gln Leu Ile Gln Val Arg
            340                 345             350
Arg Ala Ala Gly Val Arg Ala Asp Ser Ala Ile Ser Phe His Ser Gly
        355                 360             365
Tyr Ser Gly Leu Val Ala Thr Val Ser Gly Ser Gln Gln Thr Leu Val
    370                 375             380
Val Ala Leu Asn Ser Asp Leu Gly Asn Pro Gly Gln Val Ala Ser Gly
385                 390                 395             400
Ser Phe Ser Glu Ala Val Asn Ala Ser Asn Gly Gln Val Arg Val Trp
                405                 410             415
Arg Ser Gly Thr Gly Ser Gly Gly Glu Pro Gly Ala Leu Val Ser
            420                 425             430
Val Ser Phe Arg Cys Asp Asn Gly Ala Thr Gln Met Gly Asp Ser Val
        435                 440             445
Tyr Ala Val Gly Asn Val Ser Gln Leu Gly Asn Trp Ser Pro Ala Ala
    450                 455             460
Ala Leu Arg Leu Thr Asp Thr Ser Gly Tyr Pro Thr Trp Lys Gly Ser
465                 470                 475             480
Ile Ala Leu Pro Ala Gly Gln Asn Glu Glu Trp Lys Cys Leu Ile Arg
                485                 490             495
Asn Glu Ala Asn Ala Thr Gln Val Arg Gln Trp Gln Gly Gly Ala Asn
            500                 505             510
Asn Ser Leu Thr Pro Ser Glu Gly Ala Thr Thr Val Gly Arg Leu
        515                 520             525
```

```
<210> SEQ ID NO 10
<211> LENGTH: 527
<212> TYPE: PRT
<213> ORGANISM: Pseudomonas stutzeri

<400> SEQUENCE: 10

Asp Gln Ala Gly Lys Ser Pro Asn Ala Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ala Thr Ile Ala Ala
        35                  40                  45

Asp Gly Phe Ser Ala Ile Trp Met Pro Val Pro Trp Arg Asp Phe Ser
    50                  55                  60

Ser Trp Ser Asp Pro Ser Arg Ser Gly Gly Gly Glu Gly Tyr Phe Trp
65                  70                  75                  80

His Asp Phe Asn Lys Asn Ser Arg Tyr Gly Ser Asp Ala Gln Leu Arg
                85                  90                  95

Gln Ala Ala Ser Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380
```

```
Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
            435                 440                 445

Tyr Ala Val Gly Asn Val Ser Gln Leu Gly Asn Trp Ser Pro Ala Ala
        450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
                500                 505                 510

Asn Ser Leu Thr Pro Ser Glu Gly Ala Thr Thr Val Gly Arg Leu
            515                 520                 525

<210> SEQ ID NO 11
<211> LENGTH: 548
<212> TYPE: PRT
<213> ORGANISM: Pseudomonas stutzeri

<400> SEQUENCE: 11

Met Ser His Ile Leu Arg Ala Ala Val Leu Ala Ala Met Leu Leu Pro
1               5                   10                  15

Leu Pro Ser Met Ala Asp Gln Ala Gly Lys Ser Pro Asn Ala Val Arg
                20                  25                  30

Tyr His Gly Gly Asp Glu Ile Ile Leu Gln Gly Phe His Trp Asn Val
            35                  40                  45

Val Arg Glu Ala Pro Asn Asp Trp Tyr Asn Ile Leu Arg Gln Gln Ala
        50                  55                  60

Ala Thr Ile Ala Ala Asp Gly Phe Ser Ala Ile Trp Met Pro Val Pro
65                  70                  75                  80

Trp Arg Asp Phe Ser Ser Trp Ser Asp Gly Ser Lys Ser Gly Gly Gly
                85                  90                  95

Glu Gly Tyr Phe Trp His Asp Phe Asn Lys Asn Gly Arg Tyr Gly Ser
            100                 105                 110

Asp Ala Gln Leu Arg Gln Ala Ser Ala Leu Gly Gly Ala Gly Val
            115                 120                 125

Lys Val Leu Tyr Asp Val Val Pro Asn His Met Asn Arg Gly Tyr Pro
130                 135                 140

Asp Lys Glu Ile Asn Leu Pro Ala Gly Gln Gly Phe Trp Arg Asn Asp
145                 150                 155                 160

Cys Ala Asp Pro Gly Asn Tyr Pro Asn Asp Cys Asp Asp Gly Asp Arg
                165                 170                 175

Phe Ile Gly Gly Asp Ala Asp Leu Asn Thr Gly His Pro Gln Val Tyr
            180                 185                 190

Gly Met Phe Arg Asp Glu Phe Thr Asn Leu Arg Ser Gln Tyr Gly Ala
            195                 200                 205

Gly Gly Phe Arg Phe Asp Phe Val Arg Gly Tyr Ala Pro Glu Arg Val
        210                 215                 220

Asn Ser Trp Met Thr Asp Ser Ala Asp Asn Ser Phe Cys Val Gly Glu
225                 230                 235                 240
```

Leu Trp Lys Gly Pro Ser Glu Tyr Pro Asn Trp Asp Trp Arg Asn Thr
            245                 250                 255

Ala Ser Trp Gln Gln Ile Ile Lys Asp Trp Ser Arg Ala Lys Cys
        260                 265                 270

Pro Val Phe Asp Phe Ala Leu Lys Glu Arg Met Gln Asn Gly Ser Ile
        275                 280                 285

Ala Asp Trp Lys His Gly Leu Asn Gly Asn Pro Asp Pro Arg Trp Arg
290                 295                 300

Glu Val Ala Val Thr Phe Val Asp Asn His Asp Thr Gly Tyr Ser Pro
305                 310                 315                 320

Gly Gln Asn Gly Gly Gln His Trp Ala Leu Gln Asp Gly Leu Ile
            325                 330                 335

Arg Gln Ala Tyr Ala Tyr Ile Leu Thr Ser Pro Gly Thr Pro Val Val
            340                 345                 350

Tyr Trp Ser His Met Tyr Asp Trp Gly Tyr Gly Asp Phe Ile Arg Gln
            355                 360                 365

Leu Ile Gln Val Arg Arg Ala Ala Gly Val Arg Ala Asp Ser Ala Ile
    370                 375                 380

Ser Phe His Ser Gly Tyr Ser Gly Leu Val Ala Thr Val Ser Gly Ser
385                 390                 395                 400

Gln Gln Thr Leu Val Val Ala Leu Asn Ser Asp Leu Gly Asn Pro Gly
            405                 410                 415

Gln Val Ala Ser Gly Ser Phe Ser Glu Ala Val Asn Ala Ser Asn Gly
            420                 425                 430

Gln Val Arg Val Trp Arg Ser Gly Thr Gly Ser Gly Gly Glu Pro
    435                 440                 445

Gly Ala Leu Val Ser Val Ser Phe Arg Cys Asp Asn Gly Ala Thr Gln
450                 455                 460

Met Gly Asp Ser Val Tyr Ala Val Gly Asn Val Ser Gln Leu Gly Asn
465                 470                 475                 480

Trp Ser Pro Ala Ala Ala Leu Arg Leu Thr Asp Thr Ser Gly Tyr Pro
            485                 490                 495

Thr Trp Lys Gly Ser Ile Ala Leu Pro Ala Gly Gln Asn Glu Glu Trp
            500                 505                 510

Lys Cys Leu Ile Arg Asn Glu Ala Asn Ala Thr Gln Val Arg Gln Trp
    515                 520                 525

Gln Gly Gly Ala Asn Asn Ser Leu Thr Pro Ser Glu Gly Ala Thr Thr
530                 535                 540

Val Gly Arg Leu
545

<210> SEQ ID NO 12
<211> LENGTH: 2082
<212> TYPE: DNA
<213> ORGANISM: Pseudomonas stutzeri

<400> SEQUENCE: 12
gatcggcctt tacggaaagt gatagagctt ctcttccggc aaactttgtt ccccagtgac      60
agagggttag tatcggatcg cttcctcttt gggtttggta gatcaggagc gccgagagca     120
ggatgaaatc ctgcggccag aaggtcgcgc gaagatgtgt gaactgctgc tggccgagat     180
ccggccggcg ttcatcctcg tccggcggcc ttgccgccag ctacccgaac aagcacaaga     240
accggagtat tgcgatgagc cacatcctgc gagccgccgt attggcggcg atgctgttgc     300
cgttgccgtc catggccgat caggccggca agagccccaa cgctgtgcgc taccacggcg     360

```
gcgacgaaat cattctccag ggctttcact ggaacgtcgt ccgcgaagcg cccaacgact    420
ggtacaacat cctgcgccag caggccgcga ccatcgccgc cgacggcttc tcggcgatct    480
ggatgccggt gccctggcgc gacttctcca gctggagcga cggcagcaag tccggcggcg    540
gtgaaggcta cttctggcac gacttcaaca agaacggccg ctatggcagt gacgcccagc    600
tgcgtcaggc cgccagcgcg ctcggtggcg ccggcgtgaa agtgctttac gacgtggtgc    660
ccaaccacat gaaccgtggc tatccggaca aggagatcaa cctcccggcc ggccagggct    720
tctggcgcaa cgactgcgcc gacccgggca actaccccaa tgattgcgac gacggcgacc    780
gcttcatcgg cggcgatgcg gacctcaaca ccggccaccc gcaggtctac ggcatgttcc    840
gcgatgaatt caccaacctg cgcagtcagt acggtgccgg cggcttccgc ttcgactttg    900
ttcggggcta tgcgccggag cgggtcaaca gctggatgac cgatagcgcc gacaacagct    960
tctgcgtcgg cgaactgtgg aaaggcccct ctgagtaccc gaactgggac tggcgcaaca   1020
ccgccagctg gcagcagatc atcaaggact ggtccgaccg ggccaagtgc ccggtgttcg   1080
acttcgccct caaggaacgc atgcagaacg ctcgatcgcc gactggaagc acgcctgaac   1140
ggcaatcccg accgcgtggg cgcgaggtgg cggtgacctt cgtcgacaac cacgacaccg   1200
gctactcgcc cgggcagaac ggtgggcagc accactgggc tctgcaggac gggctgatcc   1260
gccaggccta cgcctacatc ctcaccagcc cggtacgcc ggtggtgtac tggtcgcaca   1320
tgtacgactg gggttacggc gacttcatcc gtcagctgat ccaggtgcgt cgcgccgccg   1380
gcgtgcgcgc cgattcggcg atcagcttcc acagcggcta cagcggtctg gtcgccaccg   1440
tcagcggcag ccagcagacc ctggtggtgg cgctcaactc cgacctgggc aatcccggcc   1500
aggtggccag cggcagcttc agcgaggcgg tcaacgccag caacggccag gtgcgcgtgt   1560
ggcgtagcgg cacgggcagc ggtggcggtg aacccggcgc tctggtcagt gtgagtttcc   1620
gctgcgacaa cggcgcgacg cagatggcg acagcgtcta cgcggtcggc aacgtcagcc   1680
agctcggtaa ctggagcccg ccgcggcgt tgcgcctgac cgacaccagc ggctacccga   1740
cctggaaggg cagcattgcc ttgcctgccg gccagaacga ggaatggaaa tgcctgatcc   1800
gcaacgaggc caacgccacc caggtgcggc aatggcaggg cggggcaaac aacagcctga   1860
cgccgagcga gggcgccacc accgtcggcc ggctctagcc cgggcggcaa ctcggccgtc   1920
tcgcggatgt gaggcggctg gtctcggcgg cggtatcgtt gcgctggggg cggggccgcc   1980
gttcacgcgc cctgctatcg ctagttttcg gcgctccgcg catcggccag ttgccagcga   2040
atcgcctgcg cttcggcctg gtgcaggtcg tcgagcagcg ct                      2082
```

<210> SEQ ID NO 13
<211> LENGTH: 430
<212> TYPE: PRT
<213> ORGANISM: Pseudomonas saccharophila

<400> SEQUENCE: 13

Met Asp Gln Ala Gly Lys Ser Pro Ala Gly Val Arg Tyr His Gly
1               5                   10                  15

Asp Glu Ile Ile Leu Gln Gly Phe His Trp Asn Val Val Arg Glu Ala
            20                  25                  30

Pro Tyr Asn Trp Tyr Asn Ile Leu Arg Gln Gln Ala Ser Thr Ile Ala
        35                  40                  45

Ala Asp Gly Phe Ser Ala Ile Trp Met Pro Val Pro Trp Arg Asp Phe
    50                  55                  60

Ser Ser Trp Thr Asp Gly Gly Lys Ser Gly Gly Gly Glu Gly Tyr Phe
65                  70                  75                  80

```
Trp His Asp Phe Asn Lys Asn Gly Arg Tyr Gly Ser Asp Ala Gln Leu
            85                  90                  95

Arg Gln Ala Ala Gly Ala Leu Gly Gly Ala Gly Val Lys Val Leu Tyr
       100                 105                 110

Asp Val Val Pro Asn His Met Asn Arg Phe Tyr Pro Asp Lys Glu Ile
       115                 120                 125

Asn Leu Pro Ala Gly Gln Arg Phe Trp Arg Asn Asp Cys Pro Asp Pro
       130                 135                 140

Gly Asn Gly Pro Asn Asp Cys Asp Asp Gly Asp Arg Phe Leu Gly Gly
145                 150                 155                 160

Glu Ala Asp Leu Asn Thr Gly His Pro Gln Ile Tyr Gly Met Phe Arg
                165                 170                 175

Asp Glu Phe Thr Asn Leu Arg Ser Gly Tyr Gly Ala Gly Gly Phe Arg
            180                 185                 190

Phe Asp Phe Val Arg Gly Tyr Ala Pro Glu Arg Val Asp Ser Trp Met
        195                 200                 205

Ser Asp Ser Ala Asp Ser Ser Phe Cys Val Gly Glu Leu Trp Lys Glu
    210                 215                 220

Pro Ser Glu Tyr Pro Pro Trp Asp Trp Arg Asn Thr Ala Ser Trp Gln
225                 230                 235                 240

Gln Ile Ile Lys Asp Trp Ser Asp Arg Ala Lys Cys Pro Val Phe Asp
                245                 250                 255

Phe Ala Leu Lys Glu Arg Met Gln Asn Gly Ser Val Ala Asp Trp Lys
            260                 265                 270

Gln Gly Leu Asn Gly Asn Pro Asp Pro Arg Trp Arg Glu Val Ala Val
        275                 280                 285

Thr Phe Val Asp Asn His Asp Thr Gly Tyr Ser Pro Gly Gln Asn Glu
    290                 295                 300

Gly Gln His Leu Trp Pro Leu Gln Asp Gly Leu Ile Arg Gln Ala Tyr
305                 310                 315                 320

Ala Tyr Ile Leu Thr Ser Pro Gly Thr Pro Val Val Tyr Trp Pro His
                325                 330                 335

Met Tyr Asp Trp Gly Tyr Gly Asp Phe Ile Arg Gln Leu Ile Gln Val
            340                 345                 350

Arg Arg Thr Ala Gly Val Arg Ala Asp Ser Ala Ile Ser Phe His Ser
        355                 360                 365

Gly Tyr Ser Gly Leu Val Ala Thr Val Ser Gly Ser Gln Gln Thr Leu
    370                 375                 380

Val Val Ala Leu Asn Ser Asp Leu Ala Asn Pro Gly Gln Val Ala Ser
385                 390                 395                 400

Gly Ser Phe Ser Glu Ala Val Asn Ala Ser Asn Gly Gln Val Arg Val
                405                 410                 415

Trp Arg Ser Gly Ser Gly Asp Gly Gly Asn Asp Gly Gly
            420                 425                 430

<210> SEQ ID NO 14
<211> LENGTH: 1293
<212> TYPE: DNA
<213> ORGANISM: Pseudomonas saccharophila

<400> SEQUENCE: 14
atggatcagg ccggcaagag cccggccggg gtgcgctacc acggcggcga cgaaatcatc      60
ctccagggct ccactggaa cgtcgtccgc gaagcgccct acaactggta acacatcctc      120
cgccaacagg cctcgacgat cgcggccgac ggcttctcgg caatctggat gccagtgccc     180
```

```
tggcgtgact tctccagctg gaccgacggc ggcaagtccg gcggcggcga aggctacttc      240
tggcacgact tcaacaagaa cggccgctac ggcagcgacg cccagctgcg ccaggccgcc      300
ggcgcactcg gtggcgccgg ggtgaaggtg ctctacgatg tggtgcccaa tcacatgaac      360
cgcttctacc cggacaagga gatcaacctg ccggccggcc agcgcttctg gcgcaacgac      420
tgcccggatc cgggcaacgg ccccaacgac tgcgacgacg gtgaccgctt cctgggcggc      480
gaggcggacc tgaacaccgg ccatccgcag atttacggca tgtttcgcga cgagtttacc      540
aacctgcgca gcggctacgg cgccggcggc ttccgcttcg acttcgttcg cggctatgcg      600
cccgagcggg tcgacagctg gatgagcgac agcgccgaca gcagcttctg cgttggcgag      660
ctgtggaaag agccttctga atatccgccg tgggactggc gcaacacggc gagctggcag      720
cagatcatca aggactggtc cgaccgggcc aagtgcccgg tgttcgactt cgctctcaag      780
gagcgcatgc agaacggctc ggtcgccgac tggaagcagg gcctcaatgg caaccccgac      840
ccgcgctggc gcgaggtggc ggtgaccttc gtcgacaacc acgacaccgg ctattcgccc      900
gggcagaacg aaggccagca cctgtggccg ctgcaggacg gctgatccg ccaggcctac      960 gcctacatcc tcaccagccc gggcacgccg gtggtgtact ggccgcacat gtacgactgg     1020
ggctacggcg acttcatccg ccagctgatc caggtgcggc gcaccgccgg cgtgcgcgcc     1080
gattcggcga tcagcttcca tagcggctac agcggtctgg tcgctaccgt cagcggcagc     1140
cagcagaccc tggtggtggc gctcaactcc gatctggcca accccggcca ggttgccagc     1200
ggcagcttca gcgaggcggt caacgccagc aacggccagg tgcgcgtctg cgcagcggt     1260 agcggcgatg gcggcgggaa tgacggcggc tga                                 1293

<210> SEQ ID NO 15
<211> LENGTH: 430
<212> TYPE: PRT
<213> ORGANISM: Pseudomonas saccharophila

<400> SEQUENCE: 15

Met Asp Gln Ala Gly Lys Ser Pro Ala Gly Val Arg Tyr His Gly Gly
1               5                   10                  15

Asp Glu Ile Ile Leu Gln Gly Phe His Trp Asn Val Val Arg Glu Ala
                20                  25                  30

Pro Tyr Asn Trp Tyr Asn Ile Leu Arg Gln Gln Ala Ser Thr Ile Ala
            35                  40                  45

Ala Asp Gly Phe Ser Ala Ile Trp Met Pro Val Pro Trp Arg Asp Phe
        50                  55                  60

Ser Ser Trp Thr Asp Gly Gly Lys Ser Gly Gly Glu Gly Tyr Phe
65                  70                  75                  80

Trp His Asp Phe Asn Lys Asn Gly Arg Tyr Gly Ser Asp Ala Gln Leu
                85                  90                  95

Arg Gln Ala Ala Gly Ala Leu Gly Gly Ala Gly Val Lys Val Leu Tyr
            100                 105                 110

Asp Val Val Pro Asn His Met Asn Arg Phe Tyr Pro Asp Lys Glu Ile
        115                 120                 125

Asn Leu Pro Ala Gly Gln Arg Phe Trp Arg Asn Asp Cys Pro Asp Pro
    130                 135                 140

Gly Asp Gly Pro Asn Asp Cys Asp Asp Gly Asp Arg Phe Leu Gly Gly
145                 150                 155                 160

Glu Ser Asp Leu Asn Thr Gly His Pro Gln Ile Tyr Gly Met Phe Arg
                165                 170                 175
```

Asp Glu Phe Thr Asn Leu Arg Ser Gly Tyr Gly Ala Gly Gly Phe Arg
            180                 185                 190

Phe Asp Phe Val Arg Gly Tyr Ala Pro Glu Arg Val Asp Ser Trp Met
        195                 200                 205

Ser Asp Ser Ala Asp Ser Ser Phe Cys Val Gly Glu Leu Trp Lys Glu
    210                 215                 220

Pro Ser Glu Tyr Pro Pro Trp Asp Trp Arg Asn Thr Ala Ser Trp Gln
225                 230                 235                 240

Gln Ile Ile Lys Asp Trp Ser Asp Arg Ala Lys Cys Pro Val Phe Asp
                245                 250                 255

Phe Ala Leu Lys Glu Arg Met Gln Asn Gly Ser Val Ala Asp Trp Lys
            260                 265                 270

Gln Gly Leu Asn Gly Asn Pro Asp Pro Arg Trp Arg Glu Val Ala Val
        275                 280                 285

Thr Phe Val Asp Asn His Asp Thr Gly Tyr Ser Pro Gly Gln Asn Glu
    290                 295                 300

Gly Gln His Leu Trp Ala Leu Gln Asp Gly Leu Ile Arg Gln Ala Tyr
305                 310                 315                 320

Ala Tyr Ile Leu Thr Ser Pro Gly Thr Pro Val Val Tyr Trp Pro His
                325                 330                 335

Met Tyr Asp Trp Gly Tyr Gly Asp Phe Ile Arg Gln Leu Ile Gln Val
            340                 345                 350

Arg Arg Thr Ala Gly Val Arg Ala Asp Ser Ala Ile Ser Phe His Ser
        355                 360                 365

Gly Tyr Ser Gly Leu Val Ala Thr Val Ser Gly Ser Gln Gln Thr Leu
    370                 375                 380

Val Val Ala Leu Asn Ser Asp Leu Ala Asn Pro Gly Gln Val Ala Ser
385                 390                 395                 400

Gly Ser Phe Ser Glu Ala Val Asn Ala Ser Asn Gly Gln Val Arg Val
                405                 410                 415

Trp Arg Ser Gly Ser Gly Asp Gly Gly Asn Asp Gly Gly
            420                 425                 430

<210> SEQ ID NO 16
<211> LENGTH: 1293
<212> TYPE: DNA
<213> ORGANISM: Pseudomonas saccharophila

<400> SEQUENCE: 16
atggatcagg ccggcaagag cccggccggg gtgcgctacc acggcggcga cgaaatcatc    60
ctccagggct ccactggaa cgtcgtccgc gaagcgccct acaactggta caacatcctc    120
cgccaacagg cctcgacgat cgcggccgac ggcttctcgg caatctggat gccagtgccc    180
tggcgtgact ctctccagctg accgacggc ggcaagtccg gcggcggcga aggctacttc    240
tggcacgact tcaacaagaa cggccgctac ggcagcgacg cccagctgcg ccaggccgcc    300
ggcgcactcg gtggcgccgg ggtgaaggtg ctctacgatg tggtgcccaa tcacatgaac    360
cgcttctacc cggacaagga gatcaacctg ccggccggcc agcgcttctg cgcaacgac    420 tgcccggacc cgggcgacgg ccccaacgac tgcgacgacg tgaccgcttc ctgggcggc    480 gagtcggacc tgaacaccgg ccatccgcag atttacggca tgtttcgcga cgagtttacc    540
aacctgcgca gcggctacgg cgccggcggc ttccgcttcg acttcgttcg cggctatgcg    600
cccgagcggg tcgacagctg gatgagcgac agcgccgaca gcagcttctg cgttggcgag    660
ctgtggaaag agccttctga atatccgccg tgggactggc gcaacacggc gagctggcag    720

```
cagatcatca aggactggtc cgaccgggcc aagtgcccgg tgttcgactt cgctctcaag    780
gagcgcatgc agaacggctc ggtcgccgac tggaagcagg gcctcaatgg caaccccgac    840
ccgcgctggc gcgaggtggc ggtgaccttc gtcgacaacc acgacaccgg ctattcgccc    900
gggcagaacg aaggccagca cctgtgggcg ctgcaggacg gctgatccg  ccaggcctac    960 gcctacatcc tcaccagccc gggcacgccg gtggtgtact ggccgcacat gtacgactgg   1020
ggctacggcg acttcatccg ccagctgatc caggtgcggc gcaccgccgg cgtgcgcgcc   1080
gattcggcga tcagcttcca tagcggctac agcggtctgg tcgctaccgt cagcggcagc   1140
cagcagaccc tggtggtggc gctcaactcc gatctggcca accccggcca ggttgccagc   1200
ggcagcttca gcgaggcggt caacgccagc aacggccagg tgcgcgtctg gcgcagcggt   1260
agcggcgatg gcggcgggaa tgacggcggc tga                                1293
```

<210> SEQ ID NO 17
<211> LENGTH: 430
<212> TYPE: PRT
<213> ORGANISM: Pseudomonas saccharophila

<400> SEQUENCE: 17

```
Met Asp Gln Ala Gly Lys Ser Pro Ala Gly Val Arg Tyr His Gly Gly
1               5                   10                  15

Asp Glu Ile Ile Leu Gln Gly Phe His Trp Asn Val Val Arg Glu Ala
            20                  25                  30

Pro Tyr Asn Trp Tyr Asn Ile Leu Arg Gln Gln Ala Ser Thr Ile Ala
        35                  40                  45

Ala Asp Gly Phe Ser Ala Ile Trp Met Pro Val Pro Trp Arg Asp Phe
    50                  55                  60

Ser Ser Trp Thr Asp Gly Gly Lys Ser Gly Gly Glu Gly Tyr Phe
65                  70                  75                  80

Trp His Asp Phe Asn Lys Asn Gly Arg Tyr Gly Ser Asp Ala Gln Leu
                85                  90                  95

Arg Gln Ala Ala Gly Ala Leu Gly Gly Ala Gly Val Lys Val Leu Tyr
            100                 105                 110

Asp Val Val Pro Asn His Met Asn Arg Asp Tyr Pro Asp Lys Glu Ile
        115                 120                 125

Asn Leu Pro Ala Gly Gln Arg Phe Trp Arg Asn Asp Cys Pro Asp Pro
    130                 135                 140

Gly Asn Gly Pro Asn Asp Cys Asp Asp Gly Asp Arg Phe Leu Gly Gly
145                 150                 155                 160

Glu Ser Asp Leu Asn Thr Gly His Pro Gln Ile Tyr Gly Met Phe Arg
                165                 170                 175

Asp Glu Phe Thr Asn Leu Arg Ser Gly Tyr Gly Ala Gly Gly Phe Arg
            180                 185                 190

Phe Asp Phe Val Arg Gly Tyr Ala Pro Glu Arg Val Asp Ser Trp Met
        195                 200                 205

Ser Asp Ser Ala Asp Ser Ser Phe Cys Val Gly Glu Leu Trp Lys Glu
    210                 215                 220

Pro Ser Glu Tyr Pro Pro Trp Asp Trp Arg Asn Thr Ala Ser Trp Gln
225                 230                 235                 240

Gln Ile Ile Lys Asp Trp Ser Asp Arg Ala Lys Cys Pro Val Phe Asp
                245                 250                 255

Phe Ala Leu Lys Glu Arg Met Gln Asn Gly Ser Val Ala Asp Trp Lys
            260                 265                 270

Gln Gly Leu Asn Gly Asn Pro Asp Pro Arg Trp Arg Glu Val Ala Val
```

```
                     275                 280                 285
Thr Phe Val Asp Asn His Asp Thr Gly Tyr Ser Pro Gly Gln Asn Glu
    290                 295                 300

Gly Gln His Leu Trp Pro Leu Gln Asp Gly Leu Ile Arg Gln Ala Tyr
305                 310                 315                 320

Ala Tyr Ile Leu Thr Ser Pro Gly Thr Pro Val Val Tyr Trp Pro His
                325                 330                 335

Met Tyr Asp Trp Gly Tyr Gly Asp Phe Ile Arg Gln Leu Ile Gln Val
                340                 345                 350

Arg Arg Thr Ala Gly Val Arg Ala Asp Ser Ala Ile Ser Phe His Ser
                355                 360                 365

Gly Tyr Ser Gly Leu Val Ala Thr Val Ser Gly Ser Gln Gln Thr Leu
    370                 375                 380

Val Val Ala Leu Asn Ser Asp Leu Ala Asn Pro Gly Gln Val Ala Ser
385                 390                 395                 400

Gly Ser Phe Ser Glu Ala Val Asn Ala Ser Asn Gly Gln Val Arg Val
                405                 410                 415

Trp Arg Ser Gly Ser Gly Asp Gly Gly Gly Asn Asp Gly Gly
                420                 425                 430

<210> SEQ ID NO 18
<211> LENGTH: 1293
<212> TYPE: DNA
<213> ORGANISM: Pseudomonas saccharophila

<400> SEQUENCE: 18
atggatcagg ccggcaagag cccggccggg gtgcgctacc acggcggcga cgaaatcatc      60
ctccagggct ccactggaa cgtcgtccgc gaagcgccct acaactggta caacatcctc     120
cgccaacagg cctcgacgat cgcggccgac ggcttctcgg caatctggat gccagtgccc     180
tggcgtgact tctccagctg gaccgacggc ggcaagtccg cggcggcga aggctacttc     240 tggcacgact tcaacaagaa cggccgctac ggcagcgacg cccagctgcg ccaggccgcc     300
ggcgcactcg gtggccgg ggtgaaggtg ctctacgatg tggtgcccaa tcacatgaac     360
cgcgactacc cggacaagga gatcaacctg ccggccggcc agcgcttctg cgcaacgac     420 tgccccggacc cgggcaacgg ccccaacgac tgcgacgacg tgaccgcctt cctgggcggc     480
gagtcggacc tgaacaccgg ccatccgcag atttacggca tgtttcgcga cgagtttacc     540
aacctgcgca gcggctacgg cgccggcggc ttccgcttcg acttcgttcg cggctatgcg     600
cccgagcggg tcgacagctg gatgagcgac agcgccgaca gcagcttctg cgttggcgag     660
ctgtggaaag agccttctga atatccgccg tgggactggc gcaacaccgg cagctggcag     720
cagatcatca aggactggtc cgaccgggcc aagtgcccgg tgttcgactt cgctctcaag     780
gagcgcatgc agaacggctc ggtcgccgac tggaagcagg gcctcaatgg caaccccgac     840
ccgcgctggc gcgaggtggc ggtgaccttc gtcgacaacc acgacaccgg ctattcgccc     900
gggcagaacg aaggccagca cctgtggccc ctgcaggacg gctgatccg ccaggcctac     960 gcctacatcc tcaccagccc gggcacgccg gtggtgtact ggccgcacat gtacgactgg    1020
ggctacggcg acttcatccg ccagctgatc caggtgcggc gcaccgccgg cgtgcgcgcc    1080
gattcggcga tcagcttcca tagcggctac agcggtctgg tcgctaccgt cagcggcagc    1140
cagcagaccc tggtggtggc gctcaactcc gatctggcca accccggcca ggttgccagc    1200
ggcagcttca gcgaggcggt caacgccagc aacggccagg tgcgcgtctg cgcgcagcggt    1260 agcggcgatg gcggcgggaa tgacggcggc tga                                 1293
```

<210> SEQ ID NO 19
<211> LENGTH: 430
<212> TYPE: PRT
<213> ORGANISM: Pseudomonas saccharophila

<400> SEQUENCE: 19

Met Asp Gln Ser Gly Lys Ser Pro Ala Gly Val Arg Tyr His Gly Gly
1               5                   10                  15

Asp Glu Ile Ile Leu Gln Gly Phe His Trp Asn Val Val Arg Glu Ala
            20                  25                  30

Pro Tyr Asn Trp Tyr Asn Ile Leu Arg Gln Gln Ala Ser Thr Ile Ala
        35                  40                  45

Ala Asp Gly Phe Ser Ala Ile Trp Met Pro Val Pro Trp Arg Asp Phe
    50                  55                  60

Ser Ser Trp Thr Asp Gly Asp Lys Ser Gly Gly Gly Glu Gly Tyr Phe
65                  70                  75                  80

Trp His Asp Phe Asn Lys Asn Gly Arg Tyr Gly Ser Asp Ala Gln Leu
                85                  90                  95

Arg Gln Ala Ala Gly Ala Leu Gly Gly Ala Gly Val Lys Val Leu Tyr
            100                 105                 110

Asp Val Val Pro Asn His Met Asn Arg Asp Tyr Pro Asp Lys Glu Ile
        115                 120                 125

Asn Leu Pro Ala Gly Gln Arg Phe Trp Arg Asn Asp Cys Pro Asp Pro
130                 135                 140

Gly Asn Gly Pro Asn Asp Cys Asp Asp Gly Asp Arg Phe Leu Gly Gly
145                 150                 155                 160

Glu Ser Asp Leu Asn Thr Gly His Pro Gln Ile Tyr Gly Met Phe Arg
                165                 170                 175

Asp Glu Phe Thr Asn Leu Arg Ser Gly Tyr Gly Ala Gly Gly Phe Arg
            180                 185                 190

Phe Asp Phe Val Arg Gly Tyr Ala Pro Glu Arg Val Asp Ser Trp Met
        195                 200                 205

Ser Asp Ser Ala Asp Ser Ser Phe Cys Val Gly Glu Leu Trp Lys Glu
    210                 215                 220

Pro Ser Glu Tyr Pro Pro Trp Asp Trp Arg Asn Thr Ala Ser Trp Gln
225                 230                 235                 240

Gln Ile Ile Lys Asp Trp Ser Asp Arg Ala Lys Cys Pro Val Phe Asp
                245                 250                 255

Phe Ala Leu Lys Glu Arg Met Gln Asn Gly Ser Val Ala Asp Trp Lys
            260                 265                 270

Gln Gly Leu Asn Gly Asn Pro Asp Pro Arg Trp Arg Glu Val Ala Val
        275                 280                 285

Thr Phe Val Asp Asn His Asp Thr Gly Tyr Ser Pro Gly Gln Asn Glu
    290                 295                 300

Gly Gln His Leu Trp Pro Leu Gln Asp Gly Leu Ile Arg Gln Ala Tyr
305                 310                 315                 320

Ala Tyr Ile Leu Thr Ser Pro Gly Thr Pro Val Val Tyr Trp Pro His
                325                 330                 335

Met Tyr Asp Trp Gly Tyr Gly Asp Phe Ile Arg Gln Leu Ile Gln Val
            340                 345                 350

Arg Arg Thr Ala Gly Val Arg Ala Asp Ser Ala Ile Ser Phe His Ser
        355                 360                 365

Gly Tyr Ser Gly Leu Val Ala Thr Val Ser Gly Ser Gln Gln Thr Leu
370                 375                 380

-continued

Val Val Ala Leu Asn Ser Asp Leu Ala Asn Pro Gly Gln Val Ala Ser
385                 390                 395                 400

Gly Ser Phe Ser Glu Ala Val Asn Ala Ser Asn Gly Gln Val Arg Val
            405                 410                 415

Trp Arg Ser Gly Ser Gly Asp Gly Gly Gly Asn Asp Gly Gly
            420                 425                 430

<210> SEQ ID NO 20
<211> LENGTH: 1293
<212> TYPE: DNA
<213> ORGANISM: Pseudomonas saccharophila

<400> SEQUENCE: 20
atggatcaga gcggcaagag cccggccggg gtgcgctacc acggcggcga cgaaatcatc       60
ctccagggct tccactggaa cgtcgtccgc gaagcgccct acaactggta caacatcctc      120
cgccaacagg cctcgacgat cgcggccgac ggcttctcgg caatctggat gccagtgccc      180
tggcgtgact tctccagctg gaccgacggc gacaagtccg gcggcggcga aggctacttc      240
tggcacgact tcaacaagaa cggccgctac ggcagcgacg cccagctgcg ccaggccgcc      300
ggcgcactcg gtggcgccgg ggtgaaggtg ctctacgatg tggtgcccaa tcacatgaac      360
cgcgactacc cggacaagga gatcaacctg ccggccggcc agcgcttctg cgcaacgac       420 tgcccggacc cgggcaacgg ccccaacgac tgcgacgacg tgaccgcttc ctgggcggc       480 gagtcggacc tgaacaccgg ccatccgcag atttacggca tgtttcgcga cgagtttacc      540
aacctgcgca gcggctacgg cgccggcggc ttccgcttcg acttcgttcg cggctatgcg      600
cccgagcggg tcgacagctg gatgagcgac agcgccgaca gcagcttctg cgttggcgag      660
ctgtggaaag agccttctga atatccgccg tgggactggc gcaacacggc gagctggcag      720
cagatcatca aggactggtc cgaccgggcc aagtgcccgg tgttcgactt cgctctcaag      780
gagcgcatgc agaacggctc ggtcgccgac tggaagcagg gcctcaatgg caaccccgac      840
ccgcgctggc gcgaggtggc ggtgaccttc gtcgacaacc acgacaccgg ctattcgccc      900
gggcagaacg aaggccagca cctgtggccg ctgcaggacg gctgatccg ccaggcctac       960 gcctacatcc tcaccagccc gggcacgccg gtggtgtact ggccgcacat gtacgactgg     1020
ggctacggcg acttcatccg ccagctgatc caggtgcggc gcaccgccgg cgtgcgcgcc     1080
gattcggcga tcagcttcca tagcggctac agcggtctgg tcgctaccgt cagcggcagc     1140
cagcagaccc tggtggtggc gctcaactcc gatctggcca accccggcca ggttgccagc     1200
ggcagcttca gcgaggcggt caacgccagc aacggccagg tgcgcgtctg gcgcagcggt     1260
agcggcgatg gcggcgggaa tgacggcggc tga                                  1293

<210> SEQ ID NO 21
<211> LENGTH: 26
<212> TYPE: DNA
<213> ORGANISM: Artificial
<220> FEATURE:
<223> OTHER INFORMATION: Oligonucleotide primer

<400> SEQUENCE: 21
gcgaagcgcc ctacaactgg tacaac                                            26

<210> SEQ ID NO 22
<211> LENGTH: 35
<212> TYPE: DNA
<213> ORGANISM: Artificial
<220> FEATURE:

```
<223> OTHER INFORMATION: Oligonucleotide primer

<400> SEQUENCE: 22
ccaatcacat gaaccgcttc tacccggaca aggag                              35

<210> SEQ ID NO 23
<211> LENGTH: 26
<212> TYPE: DNA
<213> ORGANISM: Artificial
<220> FEATURE:
<223> OTHER INFORMATION: Oligonucleotide primer

<400> SEQUENCE: 23
ctgccggccg gccagcgctt ctggcg                                        26

<210> SEQ ID NO 24
<211> LENGTH: 26
<212> TYPE: DNA
<213> ORGANISM: Artificial
<220> FEATURE:
<223> OTHER INFORMATION: Oligonucleotide primer

<400> SEQUENCE: 24
cgccagaagc gctggccggc cggcag                                        26

<210> SEQ ID NO 25
<211> LENGTH: 23
<212> TYPE: DNA
<213> ORGANISM: Artificial
<220> FEATURE:
<223> OTHER INFORMATION: Oligonucleotide primer

<400> SEQUENCE: 25
cgcaacgact gcgccgaccc ggg                                           23

<210> SEQ ID NO 26
<211> LENGTH: 28
<212> TYPE: DNA
<213> ORGANISM: Artificial
<220> FEATURE:
<223> OTHER INFORMATION: Oligonucleotide primer

<400> SEQUENCE: 26
gatccgggca acggcccaa cgactgcg                                       28

<210> SEQ ID NO 27
<211> LENGTH: 30
<212> TYPE: DNA
<213> ORGANISM: Artificial
<220> FEATURE:
<223> OTHER INFORMATION: Oligonucleotide primer

<400> SEQUENCE: 27
gacggtgacc gcttcctggg cggcgagtcg                                    30

<210> SEQ ID NO 28
<211> LENGTH: 30
<212> TYPE: DNA
<213> ORGANISM: Artificial
<220> FEATURE:
<223> OTHER INFORMATION: Oligonucleotide primer

<400> SEQUENCE: 28
cgactcgccg cccaggaagc ggtcaccgtc                                    30

<210> SEQ ID NO 29
```

```
<211> LENGTH: 23
<212> TYPE: DNA
<213> ORGANISM: Artificial
<220> FEATURE:
<223> OTHER INFORMATION: Oligonucleotide primer

<400> SEQUENCE: 29
gggcggcgag gcggacctga aca                                              23

<210> SEQ ID NO 30
<211> LENGTH: 23
<212> TYPE: DNA
<213> ORGANISM: Artificial
<220> FEATURE:
<223> OTHER INFORMATION: Oligonucleotide primer

<400> SEQUENCE: 30
cgcgacgagt ttaccaacct gcg                                              23

<210> SEQ ID NO 31
<211> LENGTH: 35
<212> TYPE: DNA
<213> ORGANISM: Artificial
<220> FEATURE:
<223> OTHER INFORMATION: Oligonucleotide primer

<400> SEQUENCE: 31
ggcgagctgt ggaaagagcc ttctgaatat ccgag                                 35

<210> SEQ ID NO 32
<211> LENGTH: 34
<212> TYPE: DNA
<213> ORGANISM: Artificial
<220> FEATURE:
<223> OTHER INFORMATION: Oligonucleotide primer

<400> SEQUENCE: 32
gccttctgaa tatccgccgt gggactggcg caac                                  34

<210> SEQ ID NO 33
<211> LENGTH: 26
<212> TYPE: DNA
<213> ORGANISM: Artificial
<220> FEATURE:
<223> OTHER INFORMATION: Oligonucleotide primer

<400> SEQUENCE: 33
ccgactggaa gcagggcctc aatggc                                           26

<210> SEQ ID NO 34
<211> LENGTH: 28
<212> TYPE: DNA
<213> ORGANISM: Artificial
<220> FEATURE:
<223> OTHER INFORMATION: Oligonucleotide primer

<400> SEQUENCE: 34
ccgggcagaa cgaaggccag cacctgtg                                         28

<210> SEQ ID NO 35
<211> LENGTH: 31
<212> TYPE: DNA
<213> ORGANISM: Artificial
<220> FEATURE:
<223> OTHER INFORMATION: Oligonucleotide primer

<400> SEQUENCE: 35
```

-continued gaacggcggc cagcacctgt gggcgctgca g       31

<210> SEQ ID NO 36
<211> LENGTH: 31
<212> TYPE: DNA
<213> ORGANISM: Artificial
<220> FEATURE:
<223> OTHER INFORMATION: Oligonucleotide primer

<400> SEQUENCE: 36
ctgcagcgcc cacaggtgct ggccgccgtt c       31

<210> SEQ ID NO 37
<211> LENGTH: 23
<212> TYPE: DNA
<213> ORGANISM: Artificial
<220> FEATURE:
<223> OTHER INFORMATION: Oligonucleotide primer

<400> SEQUENCE: 37
gcacctgtgg ccgctgcagg acg       23

<210> SEQ ID NO 38
<211> LENGTH: 43
<212> TYPE: DNA
<213> ORGANISM: Artificial
<220> FEATURE:
<223> OTHER INFORMATION: Oligonucleotide primer

<400> SEQUENCE: 38
gtactggccg cacatgtacg actggggcta cggcgaattc atc       43

<210> SEQ ID NO 39
<211> LENGTH: 43
<212> TYPE: DNA
<213> ORGANISM: Artificial
<220> FEATURE:
<223> OTHER INFORMATION: Oligonucleotide primer

<400> SEQUENCE: 39
gatgaattcg ccgtagcccc agtcgtacat gtgcggccag tac       43

<210> SEQ ID NO 40
<211> LENGTH: 21
<212> TYPE: PRT
<213> ORGANISM: Pseudomonas saccharophila

<400> SEQUENCE: 40

Met Ser His Ile Leu Arg Ala Ala Val Leu Ala Ala Val Leu Leu Pro
1               5                   10                  15

Phe Pro Ala Leu Ala
            20

<210> SEQ ID NO 41
<211> LENGTH: 101
<212> TYPE: PRT
<213> ORGANISM: Pseudomonas saccharophila

<400> SEQUENCE: 41

Glu Gly Gly Leu Val Asn Val Asn Phe Arg Cys Asp Asn Gly Val Thr
1               5                   10                  15

Gln Met Gly Asp Ser Val Tyr Ala Val Gly Asn Val Ser Gln Leu Gly
            20                  25                  30

Asn Trp Ser Pro Ala Ser Ala Val Arg Leu Thr Asp Thr Ser Ser Tyr
        35                  40                  45

-continued

```
Pro Thr Trp Lys Gly Ser Ile Ala Leu Pro Asp Gly Gln Asn Val Glu
    50                  55                  60

Trp Lys Cys Leu Ile Arg Asn Glu Ala Asp Ala Thr Leu Val Arg Gln
65                  70                  75                  80

Trp Gln Ser Gly Gly Asn Asn Gln Val Gln Ala Ala Gly Ala Ser
                85                  90                  95

Thr Ser Gly Ser Phe
            100

<210> SEQ ID NO 42
<211> LENGTH: 530
<212> TYPE: PRT
<213> ORGANISM: Pseudomonas saccharophila
<220> FEATURE:
<221> NAME/KEY: MUTAGEN
<222> LOCATION: (3)..(3)
<223> OTHER INFORMATION: Xaa may be Ala or Ser
<220> FEATURE:
<221> NAME/KEY: MUTAGEN
<222> LOCATION: (26)..(26)
<223> OTHER INFORMATION: Xaa may be Asn, Glu or Asp
<220> FEATURE:
<221> NAME/KEY: MUTAGEN
<222> LOCATION: (33)..(33)
<223> OTHER INFORMATION: Xaa may be Asn or Tyr
<220> FEATURE:
<221> NAME/KEY: MUTAGEN
<222> LOCATION: (34)..(34)
<223> OTHER INFORMATION: Xaa may be Asp, Asn, Gly, Ala, Ser or Thr
<220> FEATURE:
<221> NAME/KEY: MUTAGEN
<222> LOCATION: (46)..(46)
<223> OTHER INFORMATION: Xaa may be Ile or Gly
<220> FEATURE:
<221> NAME/KEY: MUTAGEN
<222> LOCATION: (70)..(70)
<223> OTHER INFORMATION: Xaa may be Gly or Asp
<220> FEATURE:
<221> NAME/KEY: MUTAGEN
<222> LOCATION: (87)..(87)
<223> OTHER INFORMATION: Xaa may be Gly or Ser
<220> FEATURE:
<221> NAME/KEY: MUTAGEN
<222> LOCATION: (121)..(121)
<223> OTHER INFORMATION: Xaa may be Gly, Phe, Tyr, Trp, His, Ala, Met,
    Ser, Thr, Asp, Glu, Leu, Lys, or Val
<220> FEATURE:
<221> NAME/KEY: MUTAGEN
<222> LOCATION: (134)..(134)
<223> OTHER INFORMATION: Xaa may be Gly or Arg
<220> FEATURE:
<221> NAME/KEY: MUTAGEN
<222> LOCATION: (141)..(141)
<223> OTHER INFORMATION: Xaa may be Ala or Pro
<220> FEATURE:
<221> NAME/KEY: MUTAGEN
<222> LOCATION: (145)..(145)
<223> OTHER INFORMATION: Xaa may be Asn or Asp
<220> FEATURE:
<221> NAME/KEY: MUTAGEN
<222> LOCATION: (146)..(146)
<223> OTHER INFORMATION: Xaa may be Tyr, Met or Gly
<220> FEATURE:
<221> NAME/KEY: MUTAGEN
<222> LOCATION: (157)..(157)
<223> OTHER INFORMATION: Xaa may be Ile, Leu, Met, Val, or Asn
<220> FEATURE:
<221> NAME/KEY: MUTAGEN
<222> LOCATION: (158)..(158)
<223> OTHER INFORMATION: Xaa may be Gly, Thr, Ala or Ser
<220> FEATURE:
<221> NAME/KEY: MUTAGEN
<222> LOCATION: (160)..(160)
<223> OTHER INFORMATION: Xaa may be Glu or Asp
<220> FEATURE:
```

```
<221> NAME/KEY: MUTAGEN
<222> LOCATION: (161)..(161)
<223> OTHER INFORMATION: Xaa may be Ser or Ala
<220> FEATURE:
<221> NAME/KEY: MUTAGEN
<222> LOCATION: (178)..(178)
<223> OTHER INFORMATION: Xaa may be Leu or Phe
<220> FEATURE:
<221> NAME/KEY: MUTAGEN
<222> LOCATION: (179)..(179)
<223> OTHER INFORMATION: Xaa may be Ala, Thr, or Val
<220> FEATURE:
<221> NAME/KEY: MUTAGEN
<222> LOCATION: (188)..(188)
<223> OTHER INFORMATION: Xaa may be Gly, Ser, Thr or His
<220> FEATURE:
<221> NAME/KEY: MUTAGEN
<222> LOCATION: (198)..(198)
<223> OTHER INFORMATION: Xaa may be Tyr, Trp or Phe
<220> FEATURE:
<221> NAME/KEY: MUTAGEN
<222> LOCATION: (223)..(223)
<223> OTHER INFORMATION: Xaa may be Gly, Ala, Glu, Lys, Leu, Ile, Ser,
      Thr, Val, Arg, Pro or Asp
<220> FEATURE:
<221> NAME/KEY: MUTAGEN
<222> LOCATION: (229)..(229)
<223> OTHER INFORMATION: Xaa may be Ser or Pro
<220> FEATURE:
<221> NAME/KEY: MUTAGEN
<222> LOCATION: (272)..(272)
<223> OTHER INFORMATION: Xaa may be His or Gln
<220> FEATURE:
<221> NAME/KEY: MUTAGEN
<222> LOCATION: (303)..(303)
<223> OTHER INFORMATION: Xaa may be Gly, Glu, or Asp
<220> FEATURE:
<221> NAME/KEY: MUTAGEN
<222> LOCATION: (306)..(306)
<223> OTHER INFORMATION: Xaa may be His, Thr, or Gly
<220> FEATURE:
<221> NAME/KEY: MUTAGEN
<222> LOCATION: (307)..(307)
<223> OTHER INFORMATION: Xaa may be His, Leu, Ile, or Val
<220> FEATURE:
<221> NAME/KEY: MUTAGEN
<222> LOCATION: (309)..(309)
<223> OTHER INFORMATION: Xaa may be Ala or Pro
<220> FEATURE:
<221> NAME/KEY: MUTAGEN
<222> LOCATION: (316)..(316)
<223> OTHER INFORMATION: Xaa may be Arg, Ser, Pro, Lys, or Gln
<220> FEATURE:
<221> NAME/KEY: MUTAGEN
<222> LOCATION: (334)..(334)
<223> OTHER INFORMATION: Xaa may be Ser or Pro
<220> FEATURE:
<221> NAME/KEY: MUTAGEN
<222> LOCATION: (339)..(339)
<223> OTHER INFORMATION: Xaa may be Trp, Ala or Glu
<220> FEATURE:
<221> NAME/KEY: MUTAGEN
<222> LOCATION: (353)..(353)
<223> OTHER INFORMATION: Xaa may be Arg or Thr

<400> SEQUENCE: 42

Asp Gln Xaa Gly Lys Ser Pro Ala Gly Val Arg Tyr His Gly Gly Asp
1               5                   10                  15

Glu Ile Ile Leu Gln Gly Phe His Trp Xaa Val Val Arg Glu Ala Pro
            20                  25                  30

Xaa Xaa Trp Tyr Asn Ile Leu Arg Gln Gln Ala Ser Thr Xaa Ala Ala
        35                  40                  45

Asp Gly Phe Ser Ala Ile Trp Met Pro Val Pro Trp Arg Asp Phe Ser
    50                  55                  60

Ser Trp Thr Asp Gly Xaa Lys Ser Gly Gly Gly Glu Gly Tyr Phe Trp
```

```
65                  70                  75                  80
His Asp Phe Asn Lys Asn Xaa Arg Tyr Gly Ser Asp Ala Gln Leu Arg
                85                  90                  95
Gln Ala Ala Gly Ala Leu Gly Gly Ala Gly Val Lys Val Leu Tyr Asp
            100                 105                 110
Val Val Pro Asn His Met Asn Arg Xaa Tyr Pro Asp Lys Glu Ile Asn
        115                 120                 125
Leu Pro Ala Gly Gln Xaa Phe Trp Arg Asn Asp Cys Xaa Asp Pro Gly
    130                 135                 140
Xaa Xaa Pro Asn Asp Cys Asp Asp Gly Asp Arg Phe Xaa Xaa Gly Xaa
145                 150                 155                 160
Xaa Asp Leu Asn Thr Gly His Pro Gln Ile Tyr Gly Met Phe Arg Asp
                165                 170                 175
Glu Xaa Xaa Asn Leu Arg Ser Gly Tyr Gly Ala Xaa Gly Phe Arg Phe
            180                 185                 190
Asp Phe Val Arg Gly Xaa Ala Pro Glu Arg Val Asp Ser Trp Met Ser
        195                 200                 205
Asp Ser Ala Asp Ser Ser Phe Cys Val Gly Glu Leu Trp Lys Xaa Pro
    210                 215                 220
Ser Glu Tyr Pro Xaa Trp Asp Trp Arg Asn Thr Ala Ser Trp Gln Gln
225                 230                 235                 240
Ile Ile Lys Asp Trp Ser Asp Arg Ala Lys Cys Pro Val Phe Asp Phe
                245                 250                 255
Ala Leu Lys Glu Arg Met Gln Asn Gly Ser Val Ala Asp Trp Lys Xaa
            260                 265                 270
Gly Leu Asn Gly Asn Pro Asp Pro Arg Trp Arg Glu Val Ala Val Thr
        275                 280                 285
Phe Val Asp Asn His Asp Thr Gly Tyr Ser Pro Gly Gln Asn Xaa Gly
    290                 295                 300
Gln Xaa Xaa Trp Xaa Leu Gln Asp Gly Leu Ile Xaa Gln Ala Tyr Ala
305                 310                 315                 320
Tyr Ile Leu Thr Ser Pro Gly Thr Pro Val Val Tyr Trp Xaa His Met
                325                 330                 335
Tyr Asp Xaa Gly Tyr Gly Asp Phe Ile Arg Gln Leu Ile Gln Val Arg
            340                 345                 350
Xaa Thr Ala Gly Val Arg Ala Asp Ser Ala Ile Ser Phe His Ser Gly
        355                 360                 365
Tyr Ser Gly Leu Val Ala Thr Val Ser Gly Ser Gln Gln Thr Leu Val
    370                 375                 380
Val Ala Leu Asn Ser Asp Leu Ala Asn Pro Gly Gln Val Ala Ser Gly
385                 390                 395                 400
Ser Phe Ser Glu Ala Val Asn Ala Ser Asn Gly Gln Val Arg Val Trp
                405                 410                 415
Arg Ser Gly Ser Gly Asp Gly Gly Asn Asp Gly Gly Glu Gly Gly Gly
            420                 425                 430
Leu Val Asn Val Asn Phe Arg Cys Asp Asn Gly Val Thr Gln Met Gly
        435                 440                 445
Asp Ser Val Tyr Ala Val Gly Asn Val Ser Gln Leu Gly Asn Trp Ser
    450                 455                 460
Pro Ala Ser Ala Val Arg Leu Thr Asp Thr Ser Ser Tyr Pro Thr Trp
465                 470                 475                 480
Lys Gly Ser Ile Ala Leu Pro Asp Gly Gln Asn Val Glu Trp Lys Cys
                485                 490                 495
```

-continued

```
Leu Ile Arg Asn Glu Ala Asp Ala Thr Leu Val Arg Gln Trp Gln Ser
            500                 505                 510

Gly Gly Asn Asn Gln Val Gln Ala Ala Gly Ala Ser Thr Ser Gly
            515                 520                 525

Ser Phe
    530
```

MODIFIED AMYLASES FROM *PSEUDOMONAS* SPECIES

INCORPORATION BY REFERENCE

This application is a continuation-in-part of International Patent Application PCT/GB2006/002513 filed Jul. 7, 2006 and U.S. application Ser. No. 11/483,220, filed Jul. 7, 2006 now abandoned, both of which claim the benefit of U.S. provisional application Ser. No. 60/697,302 filed Jul. 7, 2005.

Reference is made to U.S. provisional applications Ser. Nos. 60/485,413, 60/485,539 and 60/485,616 filed Jul. 7, 2003. Reference is also made to international applications PCT/US2004/021723 and PCT/US2004/021739 filed Jul. 7, 2004 and designating the US (applicant: Genencor International, Inc). Reference is also made to U.S. utility application Ser. Nos. 10/886,905 and 10/866,903 all of which were also filed Jul. 7, 2004.

Reference is also made to U.S. provisional application Ser. No. 60/608,919 (filed as U.S. utility application Ser. No. 10/887,056 on Jul. 7, 2004 but converted to a provisional application on Sep. 15, 2004). Reference is also made to U.S. provisional application Ser. No. 60/612,407 which was filed Sep. 22, 2004.

Reference is additionally made to U.S. application Ser. No. 60/485,539 filed Jul. 7, 2003. Reference is also made to international application PCT/IB2004/002487 filed Jul. 7, 2004 and designating the US (applicant: Danisco A/S). Reference is also made to U.S. utility application Ser. No. 10/886,023 filed Jul. 7, 2004.

Reference is also made to U.S. utility application Ser. Nos. 10/886,505, 10/886,527 and 10/886,504, all of which were filed Jul. 7, 2004. Reference is also made to U.S. utility application Ser. No. 10/947,612 filed Sep. 22, 2004.

Reference is also made to International Patent Application serial number PCT/GB2005/002675 filed Jul. 7, 2005 and designating the US (applicants: Danisco A/S and Genencor International, Inc, D Young & Co).

The foregoing applications, and each document cited or referenced in each of the present and foregoing applications, including during the prosecution of each of the foregoing applications ("application and article cited documents"), and any manufacturer's instructions or catalogues for any products cited or mentioned in each of the foregoing applications and articles and in any of the application and article cited documents, are hereby incorporated herein by reference. Furthermore, all documents cited in this text, and all documents cited or reference in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

FIELD OF THE INVENTION

This invention relates to polypeptides, specifically amylase polypeptides and nucleic acids encoding these, and their uses as non-maltogenic exoamylases in producing food products. The amylases of the present invention have been engineered to have more beneficial qualities. Specifically, the amylases of the current invention show an altered exospecifity and/or altered thermostability. In particular, the polypeptides are derived from polypeptides having non-maltogenic exoamylase activity, in particular, glucan 1,4-alpha-maltotetrahydrolase (EC 3.2.1.60) activity.

BACKGROUND OF THE INVENTION

Improved amylases can ameliorate problems inherent in certain processes, such as baking. Crystallisation of amylopectin takes place in starch granules days after baking, which leads to increased firmness of bread and causes bread staling. When bread stales, bread loses crumb softness and crumb moisture. As a result, crumbs become less elastic, and bread develops a leathery crust.

Enzymatic hydrolysis (by amylases, for example) of amylopectin side chains can reduce crystallization and increase anti-staling. Crystallization depends upon the length of amylopectin side chains: the longer the side chains, the greater the crystallization. Most starch granules are composed of a mixture of two polymers: amylopectin and amylose, of which about 75% is amylopectin. Amylopectin is a very large, branched molecule consisting of chains of α-D-glucopyranosyl units joined by (1-4) linkages, where the chains are attached by α-D-(1-6) linkages to form branches. Amylose is a linear chain of (1-4) linked α-D-glucopyranosyl units having few α-D-(1-6) branches.

Baking of farinaceous bread products such as white bread, bread made from bolted rye flour and wheat flour and rolls is accomplished by baking the bread dough at oven temperatures in the range of from 180 to 250° C. for about 15 to 60 minutes. During the baking process a steep temperature gradient (200→120° C.) prevails over the outer dough layers where the crust of the baked product is developed. However, due to steam, the temperature in the crumb is only about 100° C. at the end of the baking process. Above temperatures of about 85° C., enzyme inactivation can take place and the enzyme will have no anti-staling properties. Only thermostable amylases, thus, are able to modify starch efficiently during baking.

Endoamylase activity can negatively affect the quality of the final bread product by producing a sticky or gummy crumb due to the accumulation of branched dextrins. Exoamylase activity is preferred, because it accomplishes the desired modification of starch that leads to retardation of staling, with fewer of the negative effects associated with endo-amylase activity. Reduction of endoamylase activity can lead to greater exospecifity, which can reduce branched dextrins and produce a higher quality bread.

Citation or identification of any document in this application is not an admission that such document is available as prior art to the present invention.

SUMMARY OF THE INVENTION

The invention provides a PS4 variant polypeptide which may be set out in the claims. The invention further provides for the use of such a PS4 variant polypeptide, including in and as food additives, food products, bakery products, improver compositions, feed products including animal feeds, etc as set out in the claims. The invention also provides for nucleic acids which encode and which relate to PS4 variant polypeptides, as set out in the claims. Methods for producing such PS4 variant polypeptides, as well as other aspects of the invention, are also set out in the claims.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which.

SEQUENCE LISTINGS

Figure 1:
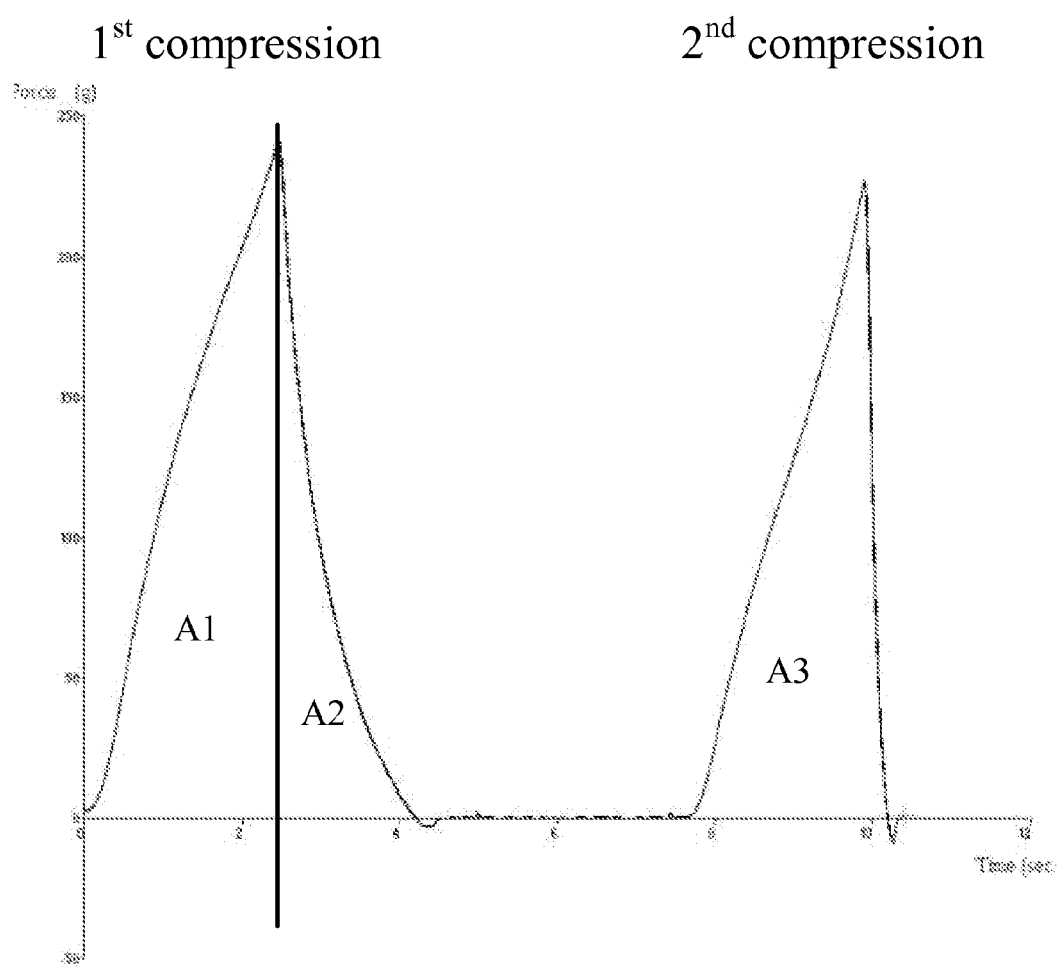
FIG. 1 shows an example of a curve from a Texture Analyser.

SEQ ID NO: 1 shows a PS4 reference sequence, derived from *Pseudomonas saccharophila* maltotetrahydrolase amino acid sequence. SEQ ID NO: 2 shows a pSac-D34 sequence; *Pseudomonas saccharophila* maltotetrahydrolase amino acid sequence with 11 substitutions and deletion of the starch binding domain. SEQ ID NO: 3 shows a pSac-D20 sequence; *Pseudomonas saccharophila* maltotetrahydrolase amino acid sequence with 13 substitutions and deletion of the starch binding domain. SEQ ID NO: 4 shows a pSac-D14 sequence; *Pseudomonas saccharophila* maltotetrahydrolase amino acid sequence with 14 substitutions and deletion of the starch binding domain. SEQ ID NO: 5 shows a *Pseudomonas saccharophila* Glucan 1,4-alpha-maltotetrahydrolase precursor (EC 3.2.1.60) (G4-amylase) (Maltotetraose-forming amylase) (Exo-maltotetraohydrolase) (Maltotetraose-forming exo-amylase). SWISS-PROT accession number P22963. SEQ ID NO: 6 shows a *P. saccharophila* mta gene encoding maltotetraohydrolase (EC number=3.2.1.60). GenBank accession number X16732. SEQ ID NO:7 shows a PS4 reference sequence, derived from *Pseudomonas stutzeri* maltotetrahydrolase amino acid sequence. SEQ ID NO: 8 shows a PStu-D34 sequence; *Pseudomonas stutzeri* maltotetrahydrolase amino acid sequence with 9 substitutions. SEQ ID NO: 9 shows a PStu-D20 sequence; *Pseudomonas stutzeri* maltotetrahydrolase amino acid sequence with 11 substitutions. SEQ ID NO: 10 shows a PStu-D14 sequence; *Pseudomonas stutzeri* maltotetrahydrolase amino acid sequence with 12 substitutions. SEQ ID NO: 11 shows a *Pseudomonas stutzeri* (*Pseudomonas perfectomarina*). Glucan 1,4-alpha-maltotetrahydrolase precursor (EC 3.2.1.60) (G4-amylase) (Maltotetraose-forming amylase) (Exo-maltotetraohydrolase) (Maltotetraose-forming exo-amylase). SWISS-PROT accession number P13507. SEQ ID NO: 12 shows a *P. stutzeri* maltotetraose-forming amylase (amyP) gene, complete cds. GenBank accession number M24516.

SEQ ID NO: 13 shows a pSac-pMD229 amino acid sequence having mutations at 33Y, 34N, 121F, 134R, 141P, 146G, 157L, 161A, 178F, 179T, 223E, 229P, 272Q, 303E, 307L, 309P and 334P. SEQ ID NO: 14 shows a pSac-pMD229 nucleic acid sequence. SEQ ID NO: 15 shows a pSac-pMD248 amino acid sequence having mutations at 33Y, 34N, 121F, 134R, 141P, 145D, 146G, 157L, 178F, 179T, 223E, 229P, 272Q, 303E, 307L and 334P. SEQ ID NO: 16 shows a pSac-pMD248 nucleic acid sequence. SEQ ID NO: 17 shows a pSac-pMD253 amino acid sequence having mutations at 33Y, 34N, 121D, 134R, 141P, 146G, 157L, 178F, 179T, 223E, 229P, 272Q, 303E, 307L, 309P and 334P. SEQ ID NO: 18 shows a pSac-pMD253 nucleic acid sequence. SEQ ID NO: 19 shows a pSac-pMD271 amino acid sequence having mutations at 3S, 33Y, 34N, 70D, 121D, 134R, 141P, 146G, 157L, 178F, 179T, 223E, 229P, 272Q, 303E, 307L, 309P and 334P. SEQ ID NO: 20 shows a pSac-pMD271 nucleic acid sequence.

DETAILED DESCRIPTION

In the following description and examples, unless the context dictates otherwise, dosages of PS4 variant polypeptides are given in parts per million (micrograms per gram) of flour. For example, "1 D34" indicates 1 part per million of pSac-D34 based on weight per weight. Preferably, enzyme quantities or amounts are determined based on activity assays as equivalents of pure enzyme protein measured with bovine serum albumin (BSA) as a standard, using the assay described in Bradford (1976, A rapid and sensitive method for the quantification of microgram quantities of protein utilizing the principle of protein-dye binding. Anal. Biochem. 72:248-254).

In describing the different PS4 variant polypeptide variants produced or which are contemplated to be encompassed by this document, the following nomenclature will be adopted for ease of reference:
  (i) where the substitution includes a number and a letter, e.g., 141P, then this refers to [position according to the numbering system/substituted amino acid]. Accordingly, for example, the substitution of an amino acid to proline in position 141 is designated as 141P;
  (ii) where the substitution includes a letter, a number and a letter, e.g., A141P, then this refers to [original amino acid/position according to the numbering system/substituted amino acid]. Accordingly, for example, the substitution of alanine with proline in position 141 is designated as A141P.

Where two or more possible substituents are possible at a particular position, this will be designated by contiguous letters, which may optionally be separated by slash marks "/", e.g., G303ED or G303E/D. Where the relevant amino acid at a position can be substituted by any amino acid, this is designated by [position according to the numbering system/X], e.g., 121X.

Multiple mutations may be designated by being separated by slash marks "/", e.g. A141P/G223A or commas ",", e.g., A141P, G223A representing mutations in position 141 and 223 substituting alanine with proline and glycine with alanine respectively.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855, Lars-Inge Larsson "*Immunocytochemistry: Theory and Practice*", CRC Press inc., Baca Raton, Fla., 1988, ISBN 0-8493-6078-1, John D. Pound (ed); "*Immunochemical Protocols, vol 80*", in the series: "Methods in Molecular Biology", Humana Press, Totowa, N.J., 1998, ISBN 0-89603-493-3, Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

All patents and publications, including all sequences disclosed within such patents and publications, referred to herein are expressly incorporated by reference.

A polypeptide is provided having a substitution at one or more positions which effect an altered property, preferably altered exospecificity or altered thermostability, or both, relative to the parent enzyme. Such variant polypeptides are referred to in this document for convenience as "PS4 variant polypeptides".

The PS4 variant polypeptides preferably exhibit enzyme activity. More preferably, the PS4 variant polypeptides comprise amylase activity, preferably exoamylase activity. In highly preferred embodiments, the PS4 variant polypeptides exhibit non-maltogenic exoamylase activity.

The invention further provides for compositions, including food additives, food products, bakery products, improver compositions, feed products including animal feeds, etc comprising such altered PS4 variant polypeptides, preferably those which have non-maltogenic exoamylase activity, as well as methods of making and using such polypeptides and the compositions.

As noted above, the PS4 variant polypeptides may comprise one or more improved handling properties, preferably improved baking properties. Thus, the PS4 variant polypeptides are such that the food products so treated have one or more of (preferably all of) a lower firmness, a higher resilience or a higher cohesiveness. Such improved handling or baking properties exhibited by the PS4 variant polypeptides are described in further detail below.

The invention provides for the treatment of food products, particularly doughs and bakery products with such polypeptides, and such that the food products exhibit the desired qualities set out above.

The invention provides for other uses of such compositions such as in the preparation of detergents, as sweeteners, syrups, etc. The compositions include the polypeptide together with at least one other component. In particular, the invention provides for food or feed additives comprising the polypeptides.

Such polypeptides and nucleic acids vary from their parent sequences by including a number of mutations. In other words, the sequence of the PS4 variant polypeptide or nucleic acid is different from that of its parent at a number of positions or residues. In preferred embodiments, the mutations comprise amino acid substitutions, that is, a change of one amino acid residue for another. Thus, the PS4 variant polypeptides comprise a number of changes in the nature of the amino acid residue at one or more positions of the parent sequence.

As used herein, the term "variant" should be taken to mean a molecule being derivable from a parent molecule. Variants include polypeptides as well as nucleic acids. Variants include deletions, insertions and substitutions at the amino acid level and transversions, transitions and inversions at the nucleic acid level among other things, at one or more locations. Variants also include truncations. Variants include homologous and functional derivatives of parent molecules. Variants include sequences that are complementary to sequences that are capable of hybridising to the nucleotide sequences presented herein.

The invention provides for PS4 variant polypeptides with sequence alterations comprising amino acid substitutions in a amylase sequence, preferably an exoamylase activity, more preferably a non-maltogenic exoamylase sequence.

Specifically, the invention provides for a PS4 variant polypeptide derivable from a parent polypeptide having non-maltogenic exoamylase activity comprising an amino acid mutation at each of positions 33, 34, 121, 134, 141, 146, 157, 161, 178, 179, 223, 229, 272, 303, 307, 309 and 334 with reference to the position numbering of a *Pseudomonas saccharophilia* exoamylase sequence shown as SEQ ID NO: 1.

The invention further provides for a PS4 variant polypeptide derivable from a parent polypeptide having non-maltogenic exoamylase activity comprising an amino acid mutation at each of positions 33, 34, 121, 134, 141, 145, 146, 157, 178, 179, 223, 229, 272, 303, 307 and 334 with reference to the position numbering of a *Pseudomonas saccharophilia* exoamylase sequence shown as SEQ ID NO: 1.

The invention also provides for a PS4 variant polypeptide derivable from a parent polypeptide having non-maltogenic exoamylase activity comprising an amino acid mutation at each of positions 33, 34, 121, 134, 141, 146, 157, 178, 179, 223, 229, 272, 303, 307, 309 and 334 with reference to the position numbering of a *Pseudomonas saccharophilia* exoamylase sequence shown as SEQ ID NO: 1.

Finally, the invention provides for a PS4 variant polypeptide derivable from a parent polypeptide having non-maltogenic exoamylase activity comprising an amino acid mutation at each of positions 3, 33, 34, 70, 121, 134, 141, 146, 157, 178, 179, 223, 229, 272, 303, 307, 309 and 334 with reference to the position numbering of a *Pseudomonas saccharophilia* exoamylase sequence shown as SEQ ID NO: 1.

In preferred embodiments each of the amino acid mutations in these polypeptides are independently selected from the group consisting of: 3S, 33Y, 34N, 70D, 121D, 121F, 134R, 141P, 145D, 146G, 157L, 161A, 178F, 179T, 223E, 229P, 272Q, 303E, 307L, 309P and 334P.

In such preferred embodiments, each of the amino acid mutations in these polypeptides are preferably independently selected from the group of substitutions consisting of: A3S, N33Y, D34N, G70D, G121D, G121F, G134R, A141P, N145D, Y146G, I157L, S161A, L178F, A179T, G223E, S229P, H272Q, G303E, H307L, A309P and S334P.

In highly preferred embodiments, the PS4 variant polypeptide a comprises the sequence pSac-pMD229 (SEQ ID NO: 13), pSac-pMD248 (SEQ ID NO: 15), pSac-pMD253 (SEQ ID NO: 17) or pSac-pMD271 (SEQ ID NO: 19).

The PS4 variant polypeptides may comprise mutations at other sites, as described in further detail below.

Such variant polypeptides, and others as described in this document, are referred to in this document as "PS4 variant polypeptides". Nucleic acids encoding such variant polypeptides are also disclosed and will be referred to for convenience as "PS4 variant nucleic acids". PS4 variant polypeptides and nucleic acids will be described in further detail below.

The "parent" sequences, i.e., the sequences on which the PS4 variant polypeptides and nucleic acids are based, preferably are polypeptides having non-maltogenic exoamylase activity. The terms "parent enzymes" and "parent polypeptides" should be interpreted accordingly, and taken to mean the enzymes and polypeptides on which the PS4 variant polypeptides are based. They are described in further detail below.

The mutations and amino acid changes may be made on any suitable polypeptide backbone or background, wild type or mutated, as described in further detail below.

In particularly preferred embodiments, the parent sequences are non-maltogenic exoamylase enzymes, preferably bacterial non-maltogenic exoamylase enzymes. In highly preferred embodiments, the parent sequence comprises a glucan 1,4-alpha-maltotetrahydrolase (EC 3.2.1.60). Preferably, the parent sequence is derivable from *Pseudomonas* species, for example *Pseudomonas saccharophilia* or *Pseudomonas stutzeri*.

In some embodiments, the parent polypeptide comprises, or is homologous to, a wild type non-maltogenic exoamylase sequence, e.g., from *Pseudomonas* spp.

Thus, the parent polypeptide may comprise a *Pseudomonas saccharophilia* non-maltogenic exoamylase having a sequence shown as SEQ ID NO: 1. In other preferred embodiments, the parent polypeptide comprises a non-maltogenic exoamylase from *Pseudomonas stutzeri* having a sequence shown as SEQ ID NO: 11, or a *Pseudomonas stutzeri* non-maltogenic exoamylase having SWISS-PROT accession number P13507.

On the other hand, the parent polypeptide may be a variant of any of the wild type sequences, that is to say, the parent polypeptide may itself be engineered, or comprise a PS4 variant polypeptide.

In preferred embodiments, the mutations and changes are made on a PS4 sequence which is already mutated, preferably pSac-D34 (e.g., SEQ ID NO: 2).

However, it will be clear to the skilled reader that although the PS4 variant polypeptides may be derivable by mutating already mutated sequences, it is possible to construct such variant polypeptides by starting from a wild type sequence (or indeed any suitable sequence), identifying the differences between the starting sequence and the desired variant, and introducing the required mutations into the starting sequence in order to achieve the desired variant.

Proteins and nucleic acids related to, preferably having sequence or functional homology with *Pseudomonas saccharophilia* non-maltogenic exoamylase sequence shown as SEQ ID NO: 1 or a *Pseudomonas stutzeri* non-maltogenic exoamylase having a sequence shown as SEQ ID NO: 11 are referred to in this document as members of the "PS4 family". Examples of "PS4 family" non-maltogenic exoamylase enzymes suitable for use in generating the PS4 variant polypeptides and nucleic acids are disclosed in further detail below.

The PS4 variant polypeptides described in this document preferably retain the features of the parent polypeptides, and additionally preferably have additional beneficial properties, for example, enhanced activity or thermostability, or pH resistance, or any combination (preferably all). This is described in further detail below.

The PS4 substitution mutants described here may be used for any suitable purpose. They may preferably be used for purposes for which the parent enzyme is suitable. In particular, they may be used in any application for which exo-maltotetraohydrolase is used. In highly preferred embodiments, they have the added advantage of higher thermostability, or higher exoamylase activity or higher pH stability, or any combination. Examples of suitable uses for the PS4 variant polypeptides and nucleic acids include food production, in particular baking, as well as production of foodstuffs; further examples are set out in detail below.

The PS4 variant polypeptides may comprise one or more further mutations in addition to those positions set out above. There may be one, two, three, four, five, six, seven or more mutations preferably substitutions in addition to those already set out. Other mutations, such as deletions, insertions and substitutions at the amino acid level and transversions, transitions and inversions at the nucleic acid level, at one or more other locations, may also be included, as described below. In addition, the PS4 variants need not have all the substitutions at the positions listed. Indeed, they may have one, two, three, four, or five substitutions missing, i.e., the wild type amino acid residue is present at such positions.

The substitution at position 3, where present, may comprise 3S, preferably, A3S.

The substitution at position 33, where present, may comprise 33Y, preferably, N33Y.

The substitution at position 34 may comprise any of 34N, 34G, 34A, 34S or 34T, preferably 34N, D34G, D34A, D34S or D34T. In highly preferred embodiments, the substitution at position 34 comprises 34N, preferably D34N.

The substitution at position 70, where present, may comprise 70D, preferably, G70D.

The substitution at position 121 may comprise any of 121F, 121Y, 121W, 121H, 121A, 121M, 121G, 121S, 121T, 121D, 121E, 121L, 121K, 121V, preferably G121F, G121Y, G121W, G121H, G121A, G121M, G121G, G121S, G121T, G121D, G121E, G121L, G121K, G121V. In highly preferred embodiments, the substitution at position 121 comprises 121D or 121F, preferably G121D or G121F.

The substitution at position 134 may comprise 134R, preferably G134R.

The substitution at position 141 may comprise 141P, preferably A141P.

The substitution at position 145, where present, may comprise 145D, preferably N145D.

The substitution at position 146 may comprise any of 146M, 146G, preferably Y146M, Y146G. In highly preferred embodiments, the substitution at position 146 comprises 146G, preferably Y146G.

The substitution at position 157 may comprise any of 157L, 157M, 157V, 157N, 157L, preferably I157L, I157M, I157V, I157N, I157L. In highly preferred embodiments, the substitution at position 157 comprises 157L, preferably I157L.

The substitution at position 161, where present, may comprise 161A, preferably S161A.

The substitution at position 178 may comprise 178F, preferably L178F.

The substitution at position 179 may comprise any of 179T, 179V, preferably A179T, A179V. In highly preferred embodiments, the substitution at position 179 comprises 179T, preferably A179T.

The substitution at position 223 may comprise any of 223A, 223E, 223K, G223L, 223I, 223S, 223T, 223V, 223R, 223P, 223D, preferably G223A, G223E, G223K, G223L, G223I, G223S, G223T, G223V, G223R, G223P, G223D. In highly preferred embodiments, the substitution at position 223 comprises 223E, preferably G223E.

The substitution at position 229 may comprise 229P, preferably S229P.

The substitution at position 272 may comprise 272Q, preferably H272Q.

The substitution at position 303 may comprise any of 303E, 303D G303E, G303D. In highly preferred embodiments, the substitution at position 303 comprises 303E, preferably G303E.

The substitution at position 307 may comprise 307L, preferably H307L.

The substitution at position 309, where present, may comprise 309P, preferably A309P.

The substitution at position 334 may comprise 334P, preferably S334P.

A mutation at 160 may also be present, preferably 160D, more preferably E160D. One or more other mutations as set out in the table below may further be present.

These substitutions in the PS4 variant polypeptides are as set out in SEQ ID NO:42.

| Position | Mutation | Substitution |
|---|---|---|
| 26 | 26E, 26D | N26E, N26D |
| 46 | 46G | I46G |
| 87 | 87S | G87S |
| 158 | 158T, 158A, 158S | G158T, G158A, G158S |
| 188 | 188, 188S, 188T or 188H | G188, G188S, G188T, G188H |
| 198 | 198W, 198F | Y198W, Y198F |
| 179 | 179T | A179T |
| 306 | 306T, 306G, 306T, 306G | H306T, H306G, H306T, H306G |
| 307 | 307L, 307I, 307V | H307L, H307I, H307V |
| 316 | 316S, 316P, 316K, 316Q | R316S, R316P, R316K, R316Q |
| 339 | 339A, 339E | W339A, W339E |
| 353 | 353T | R353T |

The invention specifically provides for a PS4 variant polypeptide derivable from a parent polypeptide having non-maltogenic exoamylase activity, in which the PS4 variant polypeptide comprises a mutation at each of the following positions 33, 34, 121, 134, 141, 146, 157, 178, 179, 223, 229, 272, 303, 307 and 334, with reference to the position numbering of a *Pseudomonas saccharophilia* exoamylase sequence shown as SEQ ID NO: 1.

The position 33 mutation may comprise 33Y, preferably N33Y. The position 34 mutation may comprise 34N, preferably D34N. The position 121 mutation may comprise 121F, preferably G121F. The position 134 mutation may comprise 134R, preferably G134R. The position 141 mutation may comprise 141P, preferably A141P. The position 146 mutation may comprise 146G, preferably Y146G. The position 157 mutation may comprise 157L, preferably I157L. The position 178 mutation may comprise 178F, preferably L178F. The position 179 mutation may comprise 179T, preferably A179T. The position 223 mutation may comprise 223E, preferably G223E. The position 229 mutation may comprise 229P, preferably S229P. The position 272 mutation may comprise 272Q, preferably H272Q. The position 303 mutation may comprise 303E, preferably G303E. The position 307 mutation may comprise 307L, preferably H307L. The position 334 mutation may comprise 334P, preferably S334P.

Preferably, the PS4 variant polypeptide comprises each of the following substitutions 33Y, 34N, 121F, 134R, 141P, 146G, 157L, 178F, 179T, 223E, 229P, 272Q, 303E, 307L and 334P, preferably N33Y, D34N, G121F, G134R, A141P, Y146G, I157L, L178F, A179T, G223E, S229P, H272Q, G303E, H307L and S334P.

In a preferred embodiment, the PS4 variant polypeptide comprises further mutations at positions 161 and 309. The position 161 mutation may comprise 161A, preferably S161A. Furthermore, the position 309 mutation may comprise 309P, preferably A309P. Preferably, the PS4 variant polypeptide comprises the sequence pSac-pMD229 (SEQ ID NO: 13).

In another preferred embodiment, the PS4 variant polypeptide comprises a further mutation at position 145. The position 145 mutation may comprise 145D, preferably N145D. Preferably, the PS4 variant polypeptide comprises the sequence pSac-pMD248 (SEQ ID NO: 15).

In a further preferred embodiment, the PS4 variant polypeptide comprises a further mutation at position 309. The position 309 mutation may comprise 309P, preferably A309P. Preferably, the PS4 variant polypeptide comprises the sequence pSac-pMD253 (SEQ ID NO: 17).

In yet a further preferred embodiment, the PS4 variant polypeptide comprises further mutations at positions 3, 70 and 309. The position 3 mutation may comprise 3S, preferably A3S. The position 70 mutation may comprise 70D, preferably G70D. The position 309 mutation may comprise 309P, preferably A309P. Preferably, the PS4 variant polypeptide comprises the sequence pSac-pMD271 (SEQ ID NO: 19).

The invention also provides PS4 nucleic acids having sequences which correspond to or encode the alterations in the PS4 variant polypeptide sequences, for use in producing such polypeptides for the purposes described here. Thus, the invention provides nucleic acids capable of encoding any polypeptide sequence set out in this document.

The skilled person will be aware of the relationship between nucleic acid sequence and polypeptide sequence, in particular, the genetic code and the degeneracy of this code, and will be able to construct such PS4 nucleic acids without difficulty. For example, the skilled artisan will be aware that for each amino acid substitution in the PS4 variant polypeptide sequence, there may be one or more codons which encode the substitute amino acid. Accordingly, it will be evident that, depending on the degeneracy of the genetic code with respect to that particular amino acid residue, one or more PS4 nucleic acid sequences may be generated corresponding to that PS4 variant polypeptide sequence. Furthermore, where the PS4 variant polypeptide comprises more than one substitution, for example A141P/G223A, the corresponding PS4 nucleic acids may comprise pairwise combinations of the codons which encode respectively the two amino acid changes.

The PS4 variant nucleic acid sequences may be derivable from parent nucleic acids which encode any of the parent polypeptides described above. In particular, parent nucleic acids may comprise wild type sequences, e.g., SEQ ID NO: 6 or SEQ ID NO: 12. The PS4 variant nucleic acids may therefore comprise nucleic acids encoding wild type non-maltogenic exoamylases, but which encode another amino acid at the relevant position instead of the wild type amino acid residue. The PS4 variant nucleic acid sequences may also comprise wild type sequences with one or more mutations, e.g., which encode parent polypeptides described above under "Combinations".

It will be understood that nucleic acid sequences which are not identical to the particular PS4 variant nucleic acid sequences, but are related to these, will also be useful for the methods and compositions described here, such as a variant, homologue, derivative or fragment of a PS4 variant nucleic acid sequence, or a complement or a sequence capable of hybridising thereof. Unless the context dictates otherwise, the term "PS4 variant nucleic acid" should be taken to include each of these entities listed above.

Mutations in amino acid sequence and nucleic acid sequence may be made by any of a number of techniques, as known in the art. Variant sequences may easily be made using any of the known mutagenesis techniques, for example, site directed mutagenesis using PCR with appropriate oligonucleotide primers, 5' add-on mutagenesis, mismatched primer mutagenesis, etc. Alternatively, or in addition, the PS4 variant nucleic acid sequences may be made de novo.

In particularly preferred embodiments, the mutations are introduced into parent sequences by means of PCR (polymerase chain reaction) using appropriate primers, as illustrated in the Examples. It is therefore possible to alter the sequence of a polypeptide by introducing any desired amino acid substitutions into a parent polypeptide, preferably having non-maltogenic exoamylase activity, such as into a *Pseudomonas saccharophilia* or a *Pseudomonas stutzeri* exoamylase sequence at amino acid or nucleic acid level, as described. The invention provides a method in which the sequence of a non-maltogenic exoamylase is altered by altering the sequence of a nucleic acid which encodes the non-maltogenic exoamylase.

However, it will of course be appreciated that the PS4 variant polypeptide does not need in fact to be actually derived from a wild type polypeptide or nucleic acid sequence by, for example, step by step mutation. Rather, once the sequence of the PS4 variant polypeptide is established, the skilled person can easily make that sequence from the wild type with all the mutations, via means known in the art, for example, using appropriate oligonucleotide primers and PCR. In fact, the PS4 variant polypeptide can be made de novo with all its mutations, through, for example, peptide synthesis methodology.

In general, however, the PS4 variant polypeptides and/or nucleic acids are derived or derivable from a "precursor" sequence. The term "precursor" as used herein means an enzyme that precedes the enzyme which is modified according to the methods and compositions described here. A precursor therefore includes an enzyme used to produce a modified enzyme. Thus, the precursor may be an enzyme that is modified by mutagenesis as described elsewhere in this document. Likewise, the precursor may be a wild type enzyme, a variant wild type enzyme or an already mutated enzyme.

The PS4 variant polypeptides and nucleic acids may be produced by any means known in the art. Specifically, they may be expressed from expression systems, which may be in vitro or in vivo in nature. Specifically, plasmids and expression vectors comprising PS4 nucleic acid sequences, preferably capable of expressing PS4 variant polypeptides are described. Cells and host cells which comprise and are preferably transformed with such PS4 nucleic acids, plasmids and vectors are also disclosed, and it should be made clear that these are also encompassed in this document.

In preferred embodiments, the PS4 variant polypeptide sequence is used as a food additive in an isolated form. The term "isolated" means that the sequence is at least substantially free from at least one other component with which the sequence is naturally associated in nature and as found in nature. In one aspect, preferably the sequence is in a purified form. The term "purified" means that the sequence is in a relatively pure state—e.g. at least about 90% pure, or at least about 91% pure, or at least about 92% pure, or at least about 93% pure, or at least about 94% pure, or at least about 95% pure, or at least about 96% pure, or at least about 97% pure, or at least about 98% pure.

The PS4 variant polypeptides may for example be made using site directed mutagenesis using PCR with appropriate oligonucleotide primers, 5' add-on mutagenesis, mismatched primer mutagenesis, etc as described in the Examples. In order to produce PS4 variant polypeptides with the relevant mutations, for example, a nucleic acid sequence corresponding to a pSac-D34 sequence (SEQ ID NO: 2) may be made and the relevant changes introduced. The skilled reader will be aware, however, that any suitable starting sequence can be used, and indeed that it is possible to start from a wild type exoamylase sequence to get to the desired variant polypeptide either in a single step, or via other intermediate sequences.

In highly preferred embodiments, the nucleic acid sequence comprises the sequence pSac-pMD229 (SEQ ID NO: 14), pSac-pMD248 (SEQ ID NO: 16), pSac-pMD253 (SEQ ID NO: 18) or pSac-pMD271 (SEQ ID NO: 20).

All positions referred to in the present document by numbering refer to the numbering of a *Pseudomonas saccharophilia* exoamylase reference sequence shown below (SEQ ID NO: 1):

```
  1 DQAGKSPAGV RYHGGDEIIL QGFHWNVVRE APNDWYNILR QQASTIAADG FSAIWMPVPW

61 RDFSSWTDGG KSGGGEGYFW HDFNKNGRYG SDAQLRQAAG ALGGAGVKVL YDVVPNHMNR

121 GYPDKEINLP AGQGFWRNDC ADPGNYPNDC DDGDRFIGGE SDLNTGHPQI YGMFRDELAN

181 LRSGYGAGGF RFDFVRGYAP ERVDSWMSDS ADSSFCVGEL WKGPSEYPSW DWRNTASWQQ

241 IIKDWSDRAK CPVFDFALKE RMQNGSVADW KHGLNGNPDP RWREVAVTFV DNHDTGYSPG

301 QNGGQHHWAL QDGLIRQAYA YILTSPGTPV VYWSHMYDWG YGDFIRQLIQ VRRTAGVRAD

361 SAISFHSGYS GLVATVSGSQ QTLVVALNSD LANPGQVASG SFSEAVNASN GQVRVWRSGS

421 GDGGGNDGGE GGLVNVNFRC DNGVTQMGDS VYAVGNVSQL GNWSPASAVR LTDTSSYPTW

481 KGSIALPDGQ NVEWKCLIRN EADATLVRQW QSGGNNQVQA AAGASTSGSF
```

The reference sequence is derived from the *Pseudomonas saccharophilia* sequence having SWISS-PROT accession number P22963, but without the signal sequence MSHILRAAVLAAVLLPFPALA.

The C-terminal starch binding domain EGGLVNVNFR CDNGVTQMGD SVYAVGNVSQ LGNWSPASAV RLTDTSSYPT WKGSIALPDG QNVEWKCLIR NEADATLVRQ WQSGGNNQVQ AAAGASTSGS F may optionally be deleted or disregarded. Alternatively, it may be included in the PS4 variant polypeptide sequence.

In the context of the present description a specific numbering of amino acid residue positions in PS4 exoamylase enzymes is employed. In this respect, by alignment of the amino acid sequences of various known exoamylases it is possible to unambiguously allot a exoamylase amino acid position number to any amino acid residue position in any exoamylase enzyme, the amino acid sequence of which is known. Using this numbering system originating from for example the amino acid sequence of the exoamylase obtained from *Pseudomonas saccharophilia*, aligned with amino acid sequences of a number of other known exoamylase, it is possible to indicate the position of an amino acid residue in a exoamylase unambiguously.

Therefore, the numbering system, even though it may use a specific sequence as a base reference point, is also applicable to all relevant homologous sequences. For example, the position numbering may be applied to homologous sequences from other *Pseudomonas* species, or homologous sequences from other bacteria. Preferably, such homologous sequences have 60% or greater homology, for example 61% or more, 62% or more 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, or 95% or more homology, with the reference sequence SEQ ID NO: 1 above, or the sequences having SWISS-PROT accession numbers P22963 or P13507, preferably with all these sequences. Sequence homology between proteins may be ascertained using well known alignment programs and hybridisation techniques described herein. Such homologous sequences, as well as the functional equivalents described below, will be referred to in this document as the "PS4 Family".

Furthermore, and as noted above, the numbering system used in this document makes reference to a reference sequence SEQ ID NO: 1, which is derived from the *Pseudomonas saccharophilia* sequence having SWISS-PROT accession number P22963, but without the signal sequence MSHILRAAVLAAVLLPFPALA. This signal sequence is located N terminal of the reference sequence and consists of 21 amino acid residues. Accordingly, it will be trivial to identify the particular residues to be mutated or substituted in corresponding sequences comprising the signal sequence, or indeed, corresponding sequences comprising any other N- or C-terminal extensions or deletions. In relation to N-terminal additions or deletions, all that is required is to offset the position numbering by the number of residues inserted or deleted. For example, position 1 in SEQ ID NO: 1 corresponds to position 22 in a sequence with the signal sequence.

The PS4 variant polypeptides are derived from, or are variants of, another sequence, known as a "parent enzyme", a "parent polypeptide" or a "parent sequence".

The term "parent enzyme" as used in this document means the enzyme that has a close, preferably the closest, chemical structure to the resultant variant, i.e., the PS4 variant polypeptide or nucleic acid. The parent enzyme may be a precursor enzyme (i.e. the enzyme that is actually mutated) or it may be prepared de novo. The parent enzyme may be a wild type enzyme, or it may be a wild type enzyme comprising one or more mutations.

The term "precursor" as used herein means an enzyme that precedes the enzyme which is modified to produce the enzyme. Thus, the precursor may be an enzyme that is modified by mutagenesis. Likewise, the precursor may be a wild type enzyme, a variant wild type enzyme or an already mutated enzyme.

The term "wild type" is a term of the art understood by skilled persons and means a phenotype that is characteristic of most of the members of a species occurring naturally and contrasting with the phenotype of a mutant. Thus, in the present context, the wild type enzyme is a form of the enzyme naturally found in most members of the relevant species. Generally, the relevant wild type enzyme in relation to the variant polypeptides described here is the most closely related corresponding wild type enzyme in terms of sequence homology. However, where a particular wild type sequence has been used as the basis for producing a variant PS4 polypeptide as described here, this will be the corresponding wild type sequence regardless of the existence of another wild type sequence that is more closely related in terms of amino acid sequence homology.

The parent enzyme or polypeptide can be any suitable starting polypeptide. It may preferably have some enzymatic activity. Preferably, this enzymatic activity is an amylase activity. More preferably, the parent polypeptide comprises exoamylase activity.

The parent enzyme is preferably a polypeptide which preferably exhibits non-maltogenic exoamylase activity. Preferably, the parent enzyme is a non-maltogenic exoamylase itself. For example, the parent enzyme may be a *Pseudomonas saccharophila* non-maltogenic exoamylase, such as a polypeptide having SWISS-PROT accession number P22963, or a *Pseudomonas stutzeri* non-maltogenic exoamylase, such as a polypeptide having SWISS-PROT accession number P13507.

Other members of the PS4 family may be used as parent enzymes; such "PS4 family members" will generally be similar to, homologous to, or functionally equivalent to either of these two enzymes, and may be identified by standard methods, such as hybridisation screening of a suitable library using probes, or by genome sequence analysis.

In particular, functional equivalents of either of these two enzymes, as well as other members of the "PS4 family" may also be used as starting points or parent polypeptides for the generation of PS4 variant polypeptides as described here.

A "functional equivalent" of a protein means something that shares one or more, preferably substantially all, of the functions of that protein. Preferably, such functions are biological functions, preferably enzymatic functions, such as amylase activity, preferably non-maltogenic exoamylase activity. Such functions may include any property of the protein, including exo-specificity, thermostability, and improved handling such as firmness, resilience and cohesiveness (as described below).

In relation to a parent enzyme, the term "functional equivalent" preferably means a molecule having similar or identical function to a parent molecule. The parent molecule may be a *Pseudomonas saccharophila* non-maltogenic exoamylase or a *Pseudomonas stutzeri* non-maltogenic exoamylase or a polypeptide obtained from other sources.

The term "functional equivalent" in relation to a parent enzyme being a *Pseudomonas saccharophila* non-maltogenic exoamylase, such as a polypeptide having SWISS-PROT accession number P22963, or a *Pseudomonas stutzeri* non-maltogenic exoamylase, such as a polypeptide having SWISS-PROT accession number P13507 means that the functional equivalent could be obtained from other sources. The functionally equivalent enzyme may have a different amino acid sequence but will have non-maltogenic exoamylase activity. Examples of assays to determine functionality are described herein and are known to one skilled in the art.

In highly preferred embodiments, the functional equivalent will have sequence homology to either of the *Pseudomonas saccharophila* and *Pseudomonas stutzeri* non-maltogenic exoamylases mentioned above, preferably both. The functional equivalent may also have sequence homology with any of the sequences set out as SEQ ID NOs: 1 to 14, preferably SEQ ID NO: 1 or SEQ ID NO: 7 or both. Sequence homology between such sequences is preferably at least 60%, preferably 65% or more, preferably 75% or more, preferably 80% or more, preferably 85% or more, preferably 90% or more, preferably 95% or more. Such sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

In other embodiments, the functional equivalents will be capable of specifically hybridising to any of the sequences set out above. Methods of determining whether one sequence is capable of hybridising to another are known in the art, and are for example described in Sambrook, et al (supra) and Ausubel, F. M. et al. (supra). In highly preferred embodiments, the functional equivalents will be capable of hybridising under stringent conditions, e.g. 65° C. and 0.1×SSC {1×SSC=0.15 M NaCl, 0.015 M $Na_3$ Citrate pH 7.0}.

For example, functional equivalents which have sequence homology to *Pseudomonas saccharophila* and *Pseudomonas stutzeri* non-maltogenic exoamylases are suitable for use as parent enzymes. Such sequences may differ from the *Pseudomonas saccharophila* sequence at any one or more positions. Furthermore, non-maltogenic exoamylases from other strains of *Pseudomonas* spp, such as ATCC17686, may also be used as a parent polypeptide. The PS4 variant polypeptide residues may be inserted into any of these parent sequences to generate the variant PS4 polypeptide sequences.

It will be understood that where it is desired for PS4 variant polypeptides to additionally comprise one or more mutations, as set out above, corresponding mutations may be made in the nucleic acid sequences of the functional equivalents of *Pseudomonas* spp non-maltogenic exoamylase, as well as other members of the "PS4 family", in order that they may be used as starting points or parent polypeptides for the generation of PS4 variant polypeptides as described here.

Specifically included within the term "PS4 variant polypeptides" are the polypeptides disclosed in:

U.S. 60/485,413, 60/485,539 and 60/485,616; PCT/US2004/021723 and PCT/US2004/021739; U.S. Ser. Nos. 10/886,905 and 10/866,903; U.S. 60/608,919; U.S. 60/612,407; U.S. 60/485,539; PCT/IB2004/002487; U.S. Ser. No. 10/886,023; U.S. Ser. No. 10/886,505, U.S. Ser. No. 10/886,527 and U.S. Ser. No. 10/886,504; U.S. Ser. No. 10/947,612. These documents however are not admitted to be prior art.

Such polypeptides are suitable for use in the applications described herein, in particular, as food additives, to treat starch as described, to prepare a food product, to make a bakery product, for the formulation of improver compositions, for the formulation of combinations, etc.

Modification of Parent Sequences

The parent enzymes may be modified at the amino acid level or the nucleic acid level to generate the PS4 variant sequences described here. Therefore, the invention provides for the generation of PS4 variant polypeptides by introducing one or more corresponding codon changes in the nucleotide sequence encoding a non-maltogenic exoamylase polypeptide.

The nucleic acid numbering should preferably be with reference to the position numbering of a *Pseudomonas saccharophilia* exoamylase nucleotide sequence shown as SEQ ID NO: 6. Alternatively, or in addition, reference may be made to the sequence with GenBank accession number X16732. In preferred embodiments, the nucleic acid numbering should be with reference to the nucleotide sequence shown as SEQ ID NO: 6. However, as with amino acid residue numbering, the residue numbering of this sequence is to be used only for reference purposes only. In particular, it will be appreciated that the above codon changes can be made in any PS4 family nucleic acid sequence. For example, sequence changes can be made to a *Pseudomonas saccharophila* or a *Pseudomonas stutzeri* non-maltogenic exoamylase nucleic acid sequence (e.g., X16732, SEQ ID NO: 6 or M24516, SEQ ID NO: 12).

The parent enzyme may comprise the "complete" enzyme, i.e., in its entire length as it occurs in nature (or as mutated), or it may comprise a truncated form thereof. The PS4 variant derived from such may accordingly be so truncated, or be "full-length". The truncation may be at the N-terminal end, or the C-terminal end, preferably the C-terminal end. The parent enzyme or PS4 variant may lack one or more portions, such as sub-sequences, signal sequences, domains or moieties, whether active or not etc. For example, the parent enzyme or the PS4 variant polypeptide may lack a signal sequence, as described above. Alternatively, or in addition, the parent enzyme or the PS4 variant may lack one or more catalytic or binding domains.

In highly preferred embodiments, the parent enzyme or PS4 variant may lack one or more of the domains present in non-maltogenic exoamylases, such as the starch binding domain. For example, the PS4 polypeptides may have only sequence up to position 429, relative to the numbering of a *Pseudomonas saccharophilila* non-maltogenic exoamylase shown as SEQ ID NO: 1. It is to be noted that this is the case for the PS4 variants pSac-d34, pSac-D20 and pSac-D14.

In other embodiments, the parent enzyme or PS4 variant may comprise a "complete" enzyme, i.e., in its entire length as it occurs in nature (or as mutated), together with one or more additional amino acid sequences at the N terminus or C terminus. For example, the parent enzyme or PS4 variant polypeptide may comprise a single extra amino acid residue at the C terminus or N terminus, e.g., M, A, G, etc. Preferably, the additional amino acid residue is present at the N terminus. Where one or more additional residues is included, the position numbering will be offset by the length of the addition.

The PS4 variant polypeptides generally comprise amylase activity.

The term "amylase" is used in its normal sense—e.g. an enzyme that is inter alia capable of catalysing the degradation of starch. In particular they are hydrolases which are capable of cleaving α-D-(1→4) O-glycosidic linkages in starch.

Amylases are starch-degrading enzymes, classified as hydrolases, which cleave α-D-(1→4) O-glycosidic linkages in starch. Generally, α-amylases (E.C. 3.2.1.1, α-D-(1→4)-glucan glucanohydrolase) are defined as endo-acting enzymes cleaving α-D-(1→4) O-glycosidic linkages within the starch molecule in a random fashion. In contrast, the exo-acting amylolytic enzymes, such as β-amylases (E.C. 3.2.1.2, α-D-(1→4)-glucan maltohydrolase), and some product-specific amylases like maltogenic alpha-amylase (E.C. 3.2.1.133) cleave the starch molecule from the non-reducing end of the substrate. β-Amylases, α-glucosidases (E.C. 3.2.1.20, α-D-glucoside glucohydrolase), glucoamylase (E.C. 3.2.1.3, α-D-(1→4)-glucan glucohydrolase), and product-specific amylases can produce malto-oligosaccharides of a specific length from starch.

The PS4 variant polypeptides described in this document are derived from (or variants of) polypeptides which preferably exhibit non-maltogenic exoamylase activity. Preferably, these parent enzymes are non-maltogenic exoamylases themselves. The PS4 variant polypeptides themselves in highly preferred embodiments also exhibit non-maltogenic exoamylase activity.

In highly preferred embodiments, the term "non-maltogenic exoamylase enzyme" as used in this document should be taken to mean that the enzyme does not initially degrade starch to substantial amounts of maltose as analysed in accordance with the product determination procedure as described in this document.

In highly preferred embodiments, the non-maltogenic exoamylase comprises an exo-maltotetraohydrolase. Exo-maltotetraohydrolase (E.C.3.2.1.60) is more formally known as glucan 1,4-alpha-maltotetrahydrolase. This enzyme hydrolyses 1,4-alpha-D-glucosidic linkages in amylaceous polysaccharides so as to remove successive maltotetraose residues from the non-reducing chain ends.

Non-maltogenic exoamylases are described in detail in U.S. Pat. No. 6,667,065, hereby incorporated by reference.

The following system is used to characterize polypeptides having non-maltogenic exoamylase activity which are suitable for use according to the methods and compositions described here. This system may for example be used to characterise the PS4 parent or variant polypeptides described here.

By way of initial background information, waxy maize amylopectin (obtainable as WAXILYS 200 from Roquette, France) is a starch with a very high amylopectin content (above 90%). 20 mg/ml of waxy maize starch is boiled for 3 min. in a buffer of 50 mM MES (2-(N-morpholino)ethanesulfonic acid), 2 mM calcium chloride, pH 6.0 and subsequently incubated at 50° C. and used within half an hour.

One unit of the non-maltogenic exoamylase is defined as the amount of enzyme which releases hydrolysis products equivalent to 1 μmol of reducing sugar per min. when incubated at 50 degrees C. in a test tube with 4 ml of 10 mg/ml waxy maize starch in 50 mM MES, 2 mM calcium chloride, pH 6.0 prepared as described above. Reducing sugars are measured using maltose as standard and using the dinitrosalicylic acid method of Bernfeld, *Methods Enzymol.*, (1954), 1, 149-158 or another method known in the art for quantifying reducing sugars.

The hydrolysis product pattern of the non-maltogenic exoamylase is determined by incubating 0.7 units of non-maltogenic exoamylase for 15 or 300 min. at 50° C. in a test tube with 4 ml of 10 mg/ml waxy maize starch in the buffer prepared as described above. The reaction is stopped by immersing the test tube for 3 min. in a boiling water bath.

The hydrolysis products are analyzed and quantified by anion exchange HPLC using a Dionex PA 100 column with sodium acetate, sodium hydroxide and water as eluents, with pulsed amperometric detection and with known linear maltooligosaccharides of from glucose to maltoheptaose as standards. The response factor used for maltooctaose to maltodecaose is the response factor found for maltoheptaose.

Preferably, the PS4 variant polypeptides have non-maltogenic exoamylase activity such that if an amount of 0.7 units of said non-maltogenic exoamylase were to incubated for 15 minutes at a temperature of 50° C. at pH 6.0 in 4 ml of an aqueous solution of 10 mg preboiled waxy maize starch per ml buffered solution containing 50 mM 2-(N-morpholino) ethane sulfonic acid and 2 mM calcium chloride then the enzyme would yield hydrolysis product(s) that would consist of one or more linear malto-oligosaccharides of from two to ten D-glucopyranosyl units and optionally glucose; such that at least 60%, preferably at least 70%, more preferably at least 80% and most preferably at least 85% by weight of the said hydrolysis products would consist of linear maltooligosaccharides of from three to ten D-glucopyranosyl units, preferably of linear maltooligosaccharides consisting of from four to eight D-glucopyranosyl units.

For ease of reference, and for the present purposes, the feature of incubating an amount of 0.7 units of the non-maltogenic exoamylase for 15 minutes at a temperature of 50° C. at pH 6.0 in 4 ml of an aqueous solution of 10 mg preboiled waxy maize starch per ml buffered solution containing 50 mM 2-(N-morpholino)ethane sulfonic acid and 2 mM calcium chloride, may be referred to as the "Waxy Maize Starch Incubation Test".

Thus, alternatively expressed, preferred PS4 variant polypeptides which are non-maltogenic exoamylases are characterised as having the ability in the waxy maize starch incubation test to yield hydrolysis product(s) that would consist of one or more linear malto-oligosaccharides of from two to ten D-glucopyranosyl units and optionally glucose; such that at least 60%, preferably at least 70%, more preferably at least 80% and most preferably at least 85% by weight of the said hydrolysis product(s) would consist of linear maltooligosaccharides of from three to ten D-glucopyranosyl units, preferably of linear maltooligosaccharides consisting of from four to eight D-glucopyranosyl units.

The hydrolysis products in the waxy maize starch incubation test may include one or more linear malto-oligosaccharides of from two to ten D-glucopyranosyl units and optionally glucose. The hydrolysis products in the waxy maize starch incubation test may also include other hydrolytic products. Nevertheless, the % weight amounts of linear maltooligosaccharides of from three to ten D-glucopyranosyl units are based on the amount of the hydrolysis product that consists of one or more linear malto-oligosaccharides of from two to ten D-glucopyranosyl units and optionally glucose. In other words, the % weight amounts of linear maltooligosaccharides of from three to ten D-glucopyranosyl units are not based on the amount of hydrolysis products other than one or more linear malto-oligosaccharides of from two to ten D-glucopyranosyl units and glucose.

The hydrolysis products can be analysed by any suitable means. For example, the hydrolysis products may be analysed by anion exchange HPLC using a Dionex PA 100 column with pulsed amperometric detection and with, for example, known linear maltooligosaccharides of from glucose to maltoheptaose as standards.

For ease of reference, and for the present purposes, the feature of analysing the hydrolysis product(s) using anion exchange HPLC using a Dionex PA 100 column with pulsed amperometric detection and with known linear maltooligosaccharides of from glucose to maltoheptaose used as standards, can be referred to as "analysing by anion exchange". Of course, and as just indicated, other analytical techniques would suffice, as well as other specific anion exchange techniques.

Thus, alternatively expressed, a preferred PS4 variant polypeptide is one which has non-maltogenic exoamylase such that it has the ability in a waxy maize starch incubation test to yield hydrolysis product(s) that would consist of one or more linear malto-oligosaccharides of from two to ten D-glucopyranosyl units and optionally glucose, said hydrolysis products being capable of being analysed by anion exchange; such that at least 60%, preferably at least 70%, more preferably at least 80% and most preferably at least 85% by weight of the said hydrolysis product(s) would consist of linear maltooligosaccharides of from three to ten D-glucopyranosyl units, preferably of linear maltooligosaccharides consisting of from four to eight D-glucopyranosyl units.

As used herein, the term "linear malto-oligosaccharide" is used in the normal sense as meaning 2-10 units of α-D-glucopyranose linked by an α-(1→4) bond.

In highly preferred embodiments, the PS4 polypeptides described here have improved exoamylase activity, preferably non-maltogenic exoamylase activity, when compared to the parent polypeptide, preferably when tested under the same conditions. In particular, in highly preferred embodiments, the PS4 variant polypeptides have 10% or more, preferably 20% or more, preferably 50% or more, exoamylase activity compared to their parents, preferably when measured in a waxy maize starch test.

The hydrolysis products can be analysed by any suitable means. For example, the hydrolysis products may be analysed by anion exchange HPLC using a Dionex PA 100 column with pulsed amperometric detection and with, for example, known linear maltooligosaccharides of from glucose to maltoheptaose as standards.

As used herein, the term "linear malto-oligosaccharide" is used in the normal sense as meaning 2-20 units of α-D-glucopyranose linked by an α-(1→4) bond.

The PS4 variants described here preferably have improved properties when compared to their parent enzymes, such as any one or more of improved thermostability, improved pH stability, or improved exo-specificity. The PS4 variants described here preferably also have improved handling properties, such that a food product treated with a the PS4 variant polypeptide has any one or all of lower firmness, higher resilience or higher cohesiveness compared to a food product which has been treated with a parent polypeptide or a wild type polypeptide.

Without wishing to be bound by any particular theory, it is believed that the mutations at the particular positions have individual and cumulative effects on the properties of a polypeptide comprising such mutations.

Preferably, the PS4 variant polypeptide is thermostable; preferably, it has higher thermostability than its parent enzyme.

In wheat and other cereals the external side chains in amylopectin are in the range of DP 12-19. Thus, enzymatic hydrolysis of the amylopectin side chains, for example, by PS4 variant polypeptides as described having non-maltogenic exoamylase activity, can markedly reduce their crystallisation tendencies.

Starch in wheat and other cereals used for baking purposes is present in the form of starch granules which generally are resistant to enzymatic attack by amylases. Thus starch modification is mainly limited to damaged starch and is progressing very slowly during dough processing and initial baking until gelatinisation starts at about 60 C. As a consequence hereof only amylases with a high degree of thermostability are able to modify starch efficiently during baking. And generally the efficiency of amylases is increased with increasing thermostability. That is because the more thermostable the enzyme is the longer time it can be active during baking and thus the more antistaling effect it will provide.

Accordingly, the use of PS4 variant polypeptides as described here when added to the starch at any stage of its processing into a food product, e.g., before during or after baking into bread can retard or impede or slow down the retrogradation. Such use is described in further detail below.

As used herein the term "thermostable" relates to the ability of the enzyme to retain activity after exposure to elevated temperatures. Preferably, the PS4 variant polypeptide is capable of degrading starch at temperatures of from about 55° C. to about 80° C. or more. Suitably, the enzyme retains its activity after exposure to temperatures of up to about 95° C.

The thermostability of an enzyme such as a non-maltogenic exoamylase is measured by its half life. Thus, the PS4 variant polypeptides described here have half lives extended relative to the parent enzyme by preferably 10%, 20%, 30%, 40%, 50%, 60%, 70%, 80%, 90%, 100%, 200% or more, preferably at elevated temperatures of from 55° C. to about 95° C. or more, preferably at about 80° C.

As used here, the half life (t½) is the time (in minutes) during which half the enzyme activity is inactivated under defined heat conditions. In preferred embodiments, the half life is assayed at 80 degrees C. Preferably, the sample is heated for 1-10 minutes at 80° C. or higher. The half life value is then calculated by measuring the residual amylase activity, by any of the methods described here. Preferably, a half life assay is conducted as described in more detail in the Examples.

Preferably, the PS4 variants described here are active during baking and hydrolyse starch during and after the gelatinization of the starch granules which starts at temperatures of about 55° C. The more thermostable the non-maltogenic exoamylase is the longer time it can be active and thus the more antistaling effect it will provide. However, during baking above temperatures of about 85° C., enzyme inactivation can take place. If this happens, the non-maltogenic exoamylase may be gradually inactivated so that there is substantially no activity after the baking process in the final bread. Therefore preferentially the non-maltogenic exoamylases suitable for use as described have an optimum temperature above 50° C. and below 98° C.

The thermostability of the PS4 variants described here can be improved by using protein engineering to become more thermostable and thus better suited for the uses described here; therefore the invention encompass the use of PS4 variants modified to become more thermostable by protein engineering.

Preferably, the PS4 variant polypeptide is pH stable; more preferably, it has a higher pH stability than its cognate parent polypeptide. As used herein the term "pH stable" relates to the ability of the enzyme to retain activity over a wide range of pHs. Preferably, the PS4 variant polypeptide is capable of degrading starch at a pH of from about 5 to about 10.5. In one embodiment, the degree of pH stability may be assayed by measuring the half life of the enzyme in specific pH conditions. In another embodiment, the degree of pH stability may be assayed by measuring the activity or specific activity of the enzyme in specific pH conditions. The specific pH conditions may be any pH from pH5 to pH10.5.

Thus, the PS4 variant polypeptide may have a longer half life, or a higher activity (depending on the assay) when compared to the parent polypeptide under identical conditions. The PS4 variant polypeptides may have 10%, 20%, 30%, 40%, 50%, 60%, 70%, 80%, 90%, 100%, 200% or longer half life when compared to their parent polypeptides under identical pH conditions. Alternatively, or in addition, they may have such higher activity when compared to the parent polypeptide under identical pH conditions.

It is known that some non-maltogenic exoamylases can have some degree of endoamylase activity. In some cases, this type of activity may need to be reduced or eliminated since endoamylase activity can possibly negatively effect the quality of the final bread product by producing a sticky or gummy crumb due to the accumulation of branched dextrins.

Exo-specificity can usefully be measured by determining the ratio of total amylase activity to the total endoamylase activity. This ratio is referred to in this document as a "Exo-specificity index". In preferred embodiments, an enzyme is considered an exoamylase if it has a exo-specificity index of 20 or more, i.e., its total amylase activity (including exo-amylase activity) is 20 times or more greater than its endoamylase activity. In highly preferred embodiments, the exo-specificity index of exoamylases is 30 or more, 40 or more, 50 or more, 60 or more, 70 or more, 80 or more, 90 or more, or 100 or more. In highly preferred embodiments, the exo-specificity index is 150 or more, 200 or more, 300 or more, 400 or more, 500 or more or 600 or more.

The total amylase activity and the endoamylase activity may be measured by any means known in the art. For example, the total amylase activity may be measured by assaying the total number of reducing ends released from a starch substrate. Alternatively, the use of a Betamyl assay is described in further detail in the Examples, and for convenience, amylase activity as assayed in the Examples is described in terms of "Betamyl Units" in the Tables.

Endoamylase activity may be assayed by use of a Phadebas Kit (Pharmacia and Upjohn). This makes use of a blue labelled crosslinked starch (labelled with an azo dye); only internal cuts in the starch molecule release label, while external cuts do not do so. Release of dye may be measured by spectrophotometry. Accordingly, the Phadebas Kit measures endoamylase activity, and for convenience, the results of such an assay (described in the Examples) are referred to in this document as "Phadebas units".

In a highly preferred embodiment, therefore, the exo-specificity index is expressed in terms of Betamyl Units/Phadebas Units, also referred to as "B/Phad".

Exo-specificity may also be assayed according to the methods described in the prior art, for example, in our International Patent Publication Number WO99/50399. This measures exo-specificity by way of a ratio between the endoamylase activity to the exoamylase activity. Thus, in a preferred aspect, the PS4 variants described here will have less than 0.5 endoamylase units (EAU) per unit of exoamylase activity. Preferably the non-maltogenic exoamylases which are suitable for use according to the present invention have less than 0.05 EAU per unit of exoamylase activity and more preferably less than 0.01 EAU per unit of exoamylase activity.

The PS4 variants described here will preferably have exospecificity, for example measured by exo-specificity indices, as described above, consistent with their being exoamylases. Moreover, they preferably have higher or increased exospecificity when compared to the parent enzymes or polypeptides from which they are derived. Thus, for example, the PS4 variant polypeptides may have 10%, 20%, 30%, 40%, 50%, 60%, 70%, 80%, 90%, 100%, 200% or higher exo-specificity index when compared to their parent polypeptides, preferably under identical conditions. They may have 1.5× or higher, 2× or higher, 5× or higher, 10× or higher, 50× or higher, 100× or higher, when compared to their parent polypeptides, preferably under identical conditions.

The PS4 variants described here preferably comprise one or more improved handling properties compared to a parent polypeptide or a wild type polypeptide. The improved handling properties may in preferred embodiments comprise improved baking properties.

Thus, the PS4 variants are such that a food product treated with the PS4 variant polypeptide an improved handling or preferably baking property compared to a food product which has been treated with a parent polypeptide or a wild type polypeptide. The handling or baking property may be selected from the group consisting of: firmness, resilience and cohesiveness.

These handling properties may be tested by any means known in the art. For example, firmness, resilience and cohesiveness may be determined by analysing bread slices by Texture Profile Analysis using for example a Texture Analyser, as described in the Examples.

The PS4 variants described here are preferably such that a food product treated with the PS4 variant polypeptide lower firmness compared to a food product which has been treated with a parent polypeptide or a wild type polypeptide.

The firmness is in preferred embodiments inversely correlated with the softness of the food product; thus, a higher softness may reflect a lower firmness, and vice versa.

Firmness is preferably measured by the "Firmness Evaluation Protocol" set out in Example 12.

Thus, the PS4 variants described here are preferably such that a food product treated with the PS4 variant polypeptide has a 10%, 20%, 30%, 40%, 50%, 60%, 70%, 80%, 90%, 100%, 200% or more lower firmness compared to a food product which has been treated with a parent polypeptide or a wild type polypeptide. A food product treated with the PS4 variant polypeptide may have a 1.1×, 1.5×, 2×, 3×, 4×, 5×, 6×, 7×, 8×, 9×, 10× or more lower firmness compared to a food product which has been treated with a parent polypeptide or a wild type polypeptide.

The PS4 variants described here are preferably such that a food product treated with the PS4 variant polypeptide higher resilience compared to a food product which has been treated with a parent polypeptide or a wild type polypeptide.

Resilience is preferably measured by the "Resilience Evaluation Protocol" set out in Example 13.

Thus, the PS4 variants described here are preferably such that a food product treated with the PS4 variant polypeptide has a 10%, 20%, 30%, 40%, 50%, 60%, 70%, 80%, 90%, 100%, 200% or more higher resilience compared to a food product which has been treated with a parent polypeptide or a wild type polypeptide. A food product treated with the PS4 variant polypeptide may have a 1.1×, 1.5×, 2×, 3×, 4×, 5×, ×, 7×, 8×, 9×, 10× or more higher resilience compared to a food product which has been treated with a parent polypeptide or a wild type polypeptide.

The PS4 variants described here are preferably such that a food product treated with the PS4 variant polypeptide higher cohesiveness compared to a food product which has been treated with a parent polypeptide or a wild type polypeptide.

Cohesiveness is preferably measured by the "Cohesiveness Evaluation Protocol" set out in Examples 14.

Thus, the PS4 variants described here are preferably such that a food product treated with the PS4 variant polypeptide has a 10%, 20%, 30%, 40%, 50%, 60%, 70%, 80%, 90%, 100%, 200% or more higher cohesiveness compared to a food product which has been treated with a parent polypeptide or a wild type polypeptide. A food product treated with the PS4 variant polypeptide may have a 1.1×, 1.5×, 2×, 3×, 4×, 5×, 6×, 7×, 8×, 9×, 10× or more higher cohesiveness compared to a food product which has been treated with a parent polypeptide or a wild type polypeptide.

The PS4 variant polypeptides, nucleic acids, host cells, expression vectors, etc, may be used in any application for which an amylase may be used. In particular, they may be used to substitute for any non-maltogenic exoamylase. They may be used to supplement amylase or non-maltogenic exoamylase activity, whether alone or in combination with other known amylases or non-maltogenic exoamylases.

The PS4 variant sequences described here may be used in various applications in the food industry—such as in bakery and drink products, they may also be used in other applications such as a pharmaceutical composition, or even in the chemical industry. In particular, the PS4 variant polypeptides and nucleic acids are useful for various industrial applications including baking (as disclosed in WO 99/50399) and flour standardisation (volume enhancement or improvement). They may be used to produce maltotetraose from starch and other substrates.

The invention therefore describes a method for preparing a food product, the method comprising: (a) obtaining a non-maltogenic exoamylase; (b) introducing a mutation at any one or more of the positions of the non-maltogenic exoamylase as set out in this document; (c) admixing the resulting polypeptide with a food ingredient.

The PS4 variant polypeptides may be used to enhance the volume of bakery products such as bread. While not wishing to be bound by any particular theory, it is believed that this results from the reduction in viscosity of the dough during heating (such as baking) as a result of the exoamylase shortening amylose molecules. This enables the carbon dioxide generated by fermentation to increase the size of the bread with less hindrance.

Thus, food products comprising or treated with PS4 variant polypeptides are expanded in volume when compared to products which have not been so treated, or treated with parent polypeptides. In other words, the food products have a larger volume of air per volume of food product. Alternatively, or in addition, the food products treated with PS4 variant polypeptides have a lower density, or weight (or mass) per volume ratio. In particularly preferred embodiments, the PS4 variant polypeptides are used to enhance the volume of bread. Volume enhancement or expansion is beneficial because it reduces the gumminess or starchiness of foods. Light foods are preferred by consumers, and the customer experience is enhanced. In preferred embodiments, the use of PS4 variant polypeptides enhances the volume by 10%, 20%, 30% 40%, 50% or more.

The use of PS4 variant polypeptides to increase the volume of foods is described in detail in the Examples.

The PS4 variant polypeptides and nucleic acids described here may be used as—or in the preparation of—a food. In particular, they may be added to a food, i.e., as a food additive. The term "food" is intended to include both prepared food, as well as an ingredient for a food, such as a flour. In a preferred aspect, the food is for human consumption. The food may be in the from of a solution or as a solid—depending on the use and/or the mode of application and/or the mode of administration.

The PS4 variant polypeptides and nucleic acids may be used as a food ingredient. As used herein the term "food ingredient" includes a formulation, which is or can be added to functional foods or foodstuffs and includes formulations which can be used at low levels in a wide variety of products that require, for example, acidifying or emulsifying. The food ingredient may be in the from of a solution or as a solid—depending on the use and/or the mode of application and/or the mode of administration.

The PS4 variant polypeptides and nucleic acids disclosed here may be—or may be added to—food supplements. The PS4 variant polypeptides and nucleic acids disclosed here may be—or may be added to—functional foods. As used herein, the term "functional food" means food which is capable of providing not only a nutritional effect and/or a taste satisfaction, but is also capable of delivering a further beneficial effect to consumer. Although there is no legal definition of a functional food, most of the parties with an interest in this area agree that they are foods marketed as having specific health effects.

The PS4 variant polypeptides may also be used in the manufacture of a food product or a foodstuff. Typical foodstuffs include dairy products, meat products, poultry products, fish products and dough products. The dough product may be any processed dough product, including fried, deep fried, roasted, baked, steamed and boiled doughs, such as steamed bread and rice cakes. In highly preferred embodiments, the food product is a bakery product.

Preferably, the foodstuff is a bakery product. Typical bakery (baked) products include bread—such as loaves, rolls, buns, pizza bases etc. pastry, pretzels, tortillas, cakes, cookies, biscuits, krackers etc.

The food products preferably benefit from one or more of the improved handling or baking properties of the PS4 variant polypeptides described here. The improved handling or baking property may be selected from the group consisting of: improved firmness, improved resilience and improved cohesiveness.

The invention therefore describes a method of modifying a food additive comprising a non-maltogenic exoamylase, the method comprising introducing a mutation at any one or more of the positions of the non-maltogenic exoamylase as set out in this document. The same method can be used to modify a food ingredient, or a food supplement, a food product, or a foodstuff.

The invention describes the use of PS4 variant proteins that are capable of retarding the staling of starch media, such as starch gels. The PS4 variant polypeptides are especially capable of retarding the detrimental retrogradation of starch.

Most starch granules are composed of a mixture of two polymers: an essentially linear amylose and a highly branched amylopectin. Amylopectin is a very large, branched molecule consisting of chains of α-D-glucopyranosyl units joined by (1-4) linkages, wherein said chains are attached by α-D-(1-6) linkages to form branches. Amylopectin is present in all natural starches, constituting about 75% of most common starches. Amylose is essentially a linear chain of (1-4) linked α-D-glucopyranosyl units having few α-D-(1-6) branches. Most starches contain about 25% amylose.

Starch granules heated in the presence of water undergo an order-disorder phase transition called gelatinization, where liquid is taken up by the swelling granules. Gelatinization temperatures vary for different starches. Upon cooling of freshly baked bread the amylose fraction, within hours, retrogrades to develop a network. This process is beneficial in that it creates a desirable crumb structure with a low degree of firmness and improved slicing properties. More gradually crystallisation of amylopectin takes place within the gelatinised starch granules during the days after baking. In this process amylopectin is believed to reinforce the amylose network in which the starch granules are embedded. This reinforcement leads to increased firmness of the bread crumb. This reinforcement is one of the main causes of bread staling.

It is known that the quality of baked products gradually deteriorates during storage As a consequence of starch recystallisation (also called retrogradation), the water-holding capacity of the crumb is changed with important implications on the organoleptic and dietary properties. The crumb loses softness and elasticity and becomes firm and crumbly. The increase in crumb firmness is often used as a measure of the staling process of bread.

The rate of detrimental retrogradation of amylopectin depends on the length of the side chains of amylopectin. Thus, enzymatic hydrolysis of the amylopectin side chains, for example, by PS4 variant polypeptides having non-maltogenic exoamylase activity, can markedly reduce their crystallisation tendencies.

Accordingly, the use of PS4 variant polypeptides as described here when added to the starch at any stage of its processing into a food product, e.g., before during or after baking into bread can retard or impede or slow down the retrogradation. Such use is described in further detail below.

The invention therefore describes a method of improving the ability of a non-maltogenic exoamylase to prevent staling, preferably detrimental retrogradation, of a dough product, the method comprising introducing a mutation at any one or more of the positions of the non-maltogenic exoamylase as set out in this document.

For evaluation of the antistaling effect of the PS4 variant polypeptides having non-maltogenic exoamylase activity described here, the crumb firmness can be measured 1, 3 and 7 days after baking by means of an Instron 4301 Universal Food Texture Analyzer or similar equipment known in the art.

Another method used traditionally in the art and which is used to evaluate the effect on starch retrogradation of a PS4 variant polypeptide having non-maltogenic exoamylase activity is based on DSC (differential scanning calorimetry). Here, the melting enthalpy of retrograded amylopectin in bread crumb or crumb from a model system dough baked with or without enzymes (control) is measured. The DSC equipment applied in the described examples is a Mettler-Toledo DSC 820 run with a temperature gradient of 10° C. per min. from 20 to 95° C. For preparation of the samples 10-20 mg of crumb are weighed and transferred into Mettler-Toledo aluminium pans which then are hermetically sealed.

The model system doughs used in the described examples contain standard wheat flour and optimal amounts of water or buffer with or without the non-maltogenic PS4 variant exoamylase. They are mixed in a 10 or 50 g Brabender Farinograph for 6 or 7 min., respectively. Samples of the doughs are placed in glass test tubes (15*0.8 cm) with a lid. These test tubes are subjected to a baking process in a water bath starting with 30 min. incubation at 33° C. followed by heating from 33 to 95° C. with a gradient of 1.1° C. per min. and finally a 5 min. incubation at 95° C. Subsequently, the tubes are stored in a thermostat at 20° C. prior to DSC analysis.

In preferred embodiments, the PS4 variants described here have a reduced melting enthalpy, compared to the control. In highly preferred embodiments, the PS4 variants have a 10% or more reduced melting enthalpy. Preferably, they have a 20% or more, 30%, 40%, 50%, 60%, 70%, 80%, 90% or more reduced melting enthalpy when compared to the control.

TABLE 2

|  | DSC (J/g) |
| --- | --- |
| Control | 2.29 |
| 0.5 D34 | 1.91 |
| 1 D34 | 1.54 |
| 2 D34 | 1.14 |

The above Table 2 shows DSC values of model dough systems prepared with different doses of pSac-D34 after 7 days of storage. 0.5, 1 and 2 parts per million (or microgram per gram) of flour are tested.

The invention provides the use of PS4 variant polypeptides in the preparation of food products, in particular, starch products. The method comprises forming the starch product by adding a non-maltogenic exoamylase enzyme such as a PS4 variant polypeptide, to a starch medium. If the starch medium is a dough, then the dough is prepared by mixing together flour, water, the non-maltogenic exoamylase which is a PS4 variant polypeptide and optionally other possible ingredients and additives.

The term "starch" should be taken to mean starch per se or a component thereof, especially amylopectin. The term "starch medium" means any suitable medium comprising starch. The term "starch product" means any product that contains or is based on or is derived from starch. Preferably, the starch product contains or is based on or is derived from starch obtained from wheat flour. The term "flour" as used herein is a synonym for the finely-ground meal of wheat or other grain. Preferably, however, the term means flour obtained from wheat per se and not from another grain. Thus, and unless otherwise expressed, references to "wheat flour" as used herein preferably mean references to wheat flour per se as well as to wheat flour when present in a medium, such as a dough.

A preferred flour is wheat flour or rye flour or mixtures of wheat and rye flour. However, dough comprising flour derived from other types of cereals such as for example rice, maize, barley, and durra are also contemplated. Preferably, the starch product is a bakery product. More preferably, the starch product is a bread product. Even more preferably, the starch product is a baked farinaceous bread product. The term "baked farinaceous bread product" refers to any baked product based on a dough obtainable by mixing flour, water, and a leavening agent under dough forming conditions. Further components can of course be added to the dough mixture.

Thus, if the starch product is a baked farinaceous bread product, then the process comprises mixing—in any suitable order—flour, water, and a leavening agent under dough forming conditions and further adding a PS4 variant polypeptide, optionally in the form of a premix. The leavening agent may be a chemical leavening agent such as sodium bicarbonate or any strain of *Saccharomyces cerevisiae* (Baker's Yeast).

The PS4 variant non-maltogenic exoamylase can be added together with any dough ingredient including the water or dough ingredient mixture or with any additive or additive mixture. The dough can be prepared by any conventional dough preparation method common in the baking industry or in any other industry making flour dough based products.

Baking of farinaceous bread products such as for example white bread, bread made from bolted rye flour and wheat flour, rolls and the like is typically accomplished by baking the bread dough at oven temperatures in the range of from 180 to 250° C. for about 15 to 60 minutes. During the baking process a steep temperature gradient (200→120° C.) is prevailing in the outer dough layers where the characteristic crust of the baked product is developed. However, owing to heat consumption due to steam generation, the temperature in the crumb is only close to 100° C. at the end of the baking process.

The invention therefore describes a process for making a bread product comprising: (a) providing a starch medium; (b) adding to the starch medium a PS4 variant polypeptide as described in this document; and (c) applying heat to the starch medium during or after step (b) to produce a bread product. The invention also describes a process for making a bread product comprising adding to a starch medium a PS4 variant polypeptide as described.

The non-maltogenic exoamylase PS4 variant polypeptide can be added as a liquid preparation or as a dry pulverulent composition either comprising the enzyme as the sole active component or in admixture with one or more additional dough ingredient or dough additive.

The invention describes improver compositions, which include bread improving compositions and dough improving compositions. These comprise a PS4 variant polypeptide, optionally together with a further ingredient, or a further enzyme, or both.

The invention also provides for the use of such a bread and dough improving compositions in baking. In a further aspect, the invention provides a baked product or dough obtained from the bread improving composition or dough improving composition. In another aspect, the invention describes a baked product or dough obtained from the use of a bread improving composition or a dough improving composition.

A dough may be prepared by admixing flour, water, a dough improving composition comprising PS4 variant polypeptide (as described above) and optionally other ingredients and additives.

The dough improving composition can be added together with any dough ingredient including the flour, water or optional other ingredients or additives. The dough improving composition can be added before the flour or water or optional other ingredients and additives. The dough improving composition can be added after the flour or water, or optional other ingredients and additives. The dough can be prepared by any conventional dough preparation method common in the baking industry or in any other industry making flour dough based products.

The dough improving composition can be added as a liquid preparation or in the form of a dry powder composition either comprising the composition as the sole active component or in admixture with one or more other dough ingredients or additive.

The amount of the PS4 variant polypeptide non-maltogenic exoamylase that is added is normally in an amount which results in the presence in the finished dough of 50 to 100,000 units per kg of flour, preferably 100 to 50,000 units per kg of flour. Preferably, the amount is in the range of 200 to 20,000 units per kg of flour. Alternatively, the PS4 variant polypeptide non-maltogenic exoamylase is added in an amount which results in the presence in the finished dough of 0.02-50 ppm of enzyme based on flour (0.02-50 mg enzyme per kg of flour), preferably 0.2-10 ppm.

In the present context, 1 unit of the non-maltogenic exoamylase is defined as the amount of enzyme which releases hydrolysis products equivalent to 1 μmol of reducing sugar per min. when incubated at 50 degrees C. in a test tube with 4 ml of 10 mg/ml waxy maize starch in 50 mM MES, 2 mM calcium chloride, pH 6.0 as described hereinafter.

The dough as described here generally comprises wheat meal or wheat flour and/or other types of meal, flour or starch such as corn flour, corn starch, maize flour, rice flour, rye meal, rye flour, oat flour, oat meal, soy flour, sorghum meal, sorghum flour, potato meal, potato flour or potato starch. The dough may be fresh, frozen, or part-baked.

The dough may be a leavened dough or a dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g. a commercially available strain of *S. cerevisiae*.

The dough may comprise fat such as granulated fat or shortening. The dough may further comprise a further emulsifier such as mono- or diglycerides, sugar esters of fatty acids, polyglycerol esters of fatty acids, lactic acid esters of monoglycerides, acetic acid esters of monoglycerides, polyoxethylene stearates, or lysolecithin.

The invention also describes a pre-mix comprising flour together with the combination as described herein. The pre-mix may contain other dough-improving and/or bread-improving additives, e.g. any of the additives, including enzymes, mentioned herein.

In order to improve further the properties of the baked product and impart distinctive qualities to the baked product further dough ingredients and/or dough additives may be incorporated into the dough. Typically, such further added components may include dough ingredients such as salt, grains, fats and oils, sugar or sweetener, dietary fibres, protein sources such as milk powder, gluten soy or eggs and dough additives such as emulsifiers, other enzymes, hydrocolloids, flavouring agents, oxidising agents, minerals and vitamins The emulsifiers are useful as dough strengtheners and crumb softeners. As dough strengtheners, the emulsifiers can provide tolerance with regard to resting time and tolerance to shock during the proofing. Furthermore, dough strengtheners will improve the tolerance of a given dough to variations in the fermentation time. Most dough strengtheners also improve on the oven spring which means the increase in volume from the proofed to the baked goods. Lastly, dough strengtheners will emulsify any fats present in the recipe mixture.

Suitable emulsifiers include lecithin, polyoxyethylene stearat, mono- and diglycerides of edible fatty acids, acetic acid esters of mono- and diglycerides of edible fatty acids, lactic acid esters of mono- and diglycerides of edible fatty acids, citric acid esters of mono- and diglycerides of edible fatty acids, diacetyl tartaric acid esters of mono- and diglycerides of edible fatty acids, sucrose esters of edible fatty acids, sodium stearoyl-2-lactylate, and calcium stearoyl-2-lactylate.

The further dough additive or ingredient can be added together with any dough ingredient including the flour, water or optional other ingredients or additives, or the dough improving composition. The further dough additive or ingredient can be added before the flour, water, optional other ingredients and additives or the dough improving composition. The further dough additive or ingredient can be added after the flour, water, optional other ingredients and additives or the dough improving composition.

The further dough additive or ingredient may conveniently be a liquid preparation. However, the further dough additive or ingredient may be conveniently in the form of a dry composition.

Preferably the further dough additive or ingredient is at least 1% the weight of the flour component of dough. More preferably, the further dough additive or ingredient is at least 2%, preferably at least 3%, preferably at least 4%, preferably at least 5%, preferably at least 6%. If the additive is a fat, then typically the fat may be present in an amount of from 1 to 5%, typically 1 to 3%, more typically about 2%.

In addition to the PS4 variant polypeptides, one or more further enzymes may be used, for example added to the food, dough preparation, foodstuff or starch composition.

Further enzymes that may be added to the dough include oxidoreductases, hydrolases, such as lipases and esterases as well as glycosidases like α-amylase, pullulanase, and xylanase. Oxidoreductases, such as for example glucose oxidase and hexose oxidase, can be used for dough strengthening and control of volume of the baked products and xylanases and other hemicellulases may be added to improve dough handling properties, crumb firmness and bread volume. Lipases are useful as dough strengtheners and crumb softeners and α-amylases and other amylolytic enzymes may be incorporated into the dough to control bread volume and further reduce crumb firmness.

Further enzymes that may be used may be selected from the group consisting of a cellulase, a hemicellulase, a starch degrading enzyme, a protease, a lipoxygenase.

Examples of useful oxidoreductases include oxidises such as maltose oxidising enzyme, a glucose oxidase (EC 1.1.3.4), carbohydrate oxidase, glycerol oxidase, pyranose oxidase, galactose oxidase (EC 1.1.3.10) and hexose oxidase (EC 1.1.3.5).

Among starch degrading enzymes, amylases are particularly useful as dough improving additives. α-amylase breaks downs starch into dextrins which are further broken down by β-amylase to maltose. Other useful starch degrading enzymes which may be added to a dough composition include glucoamylases and pullulanases.

Preferably, the further enzyme is at least a xylanase and/or at least an amylase. The term "xylanase" as used herein refers to xylanases (EC 3.2.1.32) which hydrolyse xylosidic linkages. A lipase may also be added.

The term "amylase" as used herein refers to amylases such as α-amylases (EC 3.2.1.1), β-amylases (EC 3.2.1.2) and γ-amylases (EC 3.2.1.3.

The further enzyme can be added together with any dough ingredient including the flour, water or optional other ingredients or additives, or the dough improving composition. The further enzyme can be added before the flour, water, and optionally other ingredients and additives or the dough improving composition. The further enzyme can be added after the flour, water, and optionally other ingredients and additives or the dough improving composition. The further enzyme may conveniently be a liquid preparation. However, the composition may be conveniently in the form of a dry composition.

Some enzymes of the dough improving composition are capable of interacting with each other under the dough conditions to an extent where the effect on improvement of the rheological and/or machineability properties of a flour dough and/or the quality of the product made from dough by the enzymes is not only additive, but the effect is synergistic.

In relation to improvement of the product made from dough (finished product), it may be found that the combination results in a substantial synergistic effect in respect to crumb structore. Also, with respect to the specific volume of baked product a synergistic effect may be found.

The further enzyme may be a lipase (EC 3.1.1) capable of hydrolysing carboxylic ester bonds to release carboxylate. Examples of lipases include but are not limited to triacylglycerol lipase (EC 3.1.1.3), galactolipase (EC 3.1.1.26), phospholipase A1 (EC 3.1.1.32, phospholipase A2 (EC 3.1.1.4) and lipoprotein lipase A2 (EC 3.1.1.34).

The PS4 variants are suitable for the production of maltose and high maltose syrups. Such products are of considerable interest in the production of certain confectioneries because of the low hygroscoposity, low viscosity, good heat stability and mild, not too sweet taste of maltose. The industrial process of producing maltose syrups comprises liquefying starch, then saccharification with a maltose producing enzyme, and optionally with an enzyme cleaving the 1.6-branching points in amylopectin, for instance an .alpha.-1,6-amyloglucosidase.

The PS4 variants described here may be added to and thus become a component of a detergent composition. The detergent composition may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In a specific aspect, the invention describes a detergent additive comprising the PS4 variant. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase. In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

The PS4 variant may also be used in the production of lignocellulosic materials, such as pulp, paper and cardboard, from starch reinforced waste paper and cardboard, especially where repulping occurs at pH above 7 and where amylases can facilitate the disintegration of the waste material through degradation of the reinforcing starch. The PS4 variants may especially be useful in a process for producing a papermaking pulp from starch-coated printed paper. The process may be performed as described in WO 95/14807, comprising the following steps: a) disintegrating the paper to produce a pulp, b) treating with a starch-degrading enzyme before, during or after step a), and c) separating ink particles from the pulp after steps a) and b). The PS4 variant may also be very useful in modifying starch where enzymatically modified starch is used in papermaking together with alkaline fillers such as calcium carbonate, kaolin and clays. With the PS4 variants described here it becomes possible to modify the starch in the presence of the filler thus allowing for a simpler integrated process. A PS4 variant may also be very useful in textile desizing. In the textile processing industry, amylases are traditionally used as auxiliaries in the desizing process to facilitate the removal of starch-containing size which has served as a protective coating on weft yarns during weaving. Complete removal of the size coating after weaving is important to ensure optimum results in the subsequent processes, in which the fabric is scoured, bleached and dyed. Enzymatic starch break-down is preferred because it does not involve any harmful effect on the fiber material. The PS4 variant may be used alone or in combination with a cellulase when desizing cellulose-containing fabric or textile.

The PS4 variant may also be an amylase of choice for production of sweeteners from starch A "traditional" process for conversion of starch to fructose syrups normally consists of three consecutive enzymatic processes, viz., a liquefaction process followed by a saccharification process and an isomerization process. During the liquefaction process, starch is degraded to dextrins by an amylase at pH values between 5.5 and 6.2 and at temperatures of 95-160° C. for a period of approx. 2 hours. In order to ensure an optimal enzyme stability under these conditions, 1 mM of calcium is added (40 ppm free calcium ions). After the liquefaction process the dextrins are converted into dextrose by addition of a glucoamylase and a debranching enzyme, such as an isoamylase or a pullulanase. Before this step the pH is reduced to a value below 4.5, maintaining the high temperature (above 95° C.), and the liquefying amylase activity is denatured. The temperature is lowered to 60° C., and glucoamylase and debranching enzyme are added. The saccharification process proceeds for 24-72 hours.

The PS4 variant polypeptide of the invention may in general be used to convert starch into sugars that can then be processed into ethanol or other value-added products such as high fructose corn sweetener. Thus, the use of PS4 variant polypeptides in the production of bioethanol is disclosed, which in this document should be regarded as any ethanol produced by biomass fermentation The ethanol so produced may be used as a fuel or beverage or may be used in a fermentation process for producing organic compounds, such as citric acid, ascorbic acid, lysine, glutamic acid.

Ethanol (or ethyl alcohol) is best known as being the basis of alcoholic beverages like spirits, beer and wine. In addition, ethanol has many uses in the production of industrial chemicals, pharmaceuticals and as a transportation fuel.

Ethanol can be produced from almost any raw material containing sugar or carbohydrates. As such, ethanol can be made from a wide variety of biological material. The 3 major types of biomass feedstocks used to produce ethanol include sugar crops, such as sugar cane; starch crops, including wheat and corn, and cellulosic materials, such as crop residues (straw, etc.), and forestry waste. Ethanol production from readily available sources of cellulose provides a stable, renewable fuel source.

The processing technology most frequently used is dry grain milling. In this process, the grain is first milled to a grain meal consistency. The meal is then mixed with water and amylase and passed through cookers where the starch in the grain is liquefied. Under the addition of gluco-amylase the liquefied starch is converted into fermentable sugars. Yeast is then added to the mash to ferment the sugars to ethanol. After fermentation, the mash goes through a distillation and dehydration process where the alcohol is removed from the solids and the water. In practice about two thirds of each tonne of grain is converted to fuel ethanol. The remaining by-products—thin stillage and wet distillers grain—are a high protein livestock feed which is particularly well suited for animals such as cattle or sheep.

Ethanol may also be made from cellulose containing sources, such as wood pulp. Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol, by treatment with a suitable enzyme such as cellulase.

Once ethanol leaves the processing plant, it can theoretically be used as an automotive fuel by itself or it can be mixed with gasoline at a ratio of 85 to 15 to form what is called "neat ethanol fuel". However, most commonly, ethanol is blended with gasoline at concentrations of 7 to 10% by volume. The ethanol may be used as an octane enhancer. Ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petro-chemical supplies.

In one embodiment, the PS4 variant polypeptide is capable of degrading resistant starch.

As used herein the term 'degrading' relates to the partial or complete hydrolysis or degradation of resistant starch to glucose and/or oligosaccharides—such as maltose and/or dextrins.

The PS4 variant polypeptide may degrade residual resistant starch that has not been completely degraded by an animals amylase. By way of example, the PS4 variant polypeptide may be used to assist an animal's amylase (eg. pancreatic amylase) in improving the degradation of resistant starch. Pancreatic α-amylase is excreted in the digestive system by animals. Pancreatic α-amylase degrades starch in the feed. However, a part of the starch, the resistant starch, is not degraded fully by the pancreatic α-amylase and is therefore not absorbed in the small intestine (see definition of resistant starch). The PS4 variant polypeptide in some embodiments is able to assist the pancreatic α-amylase in degrading starch in the digestive system and thereby increase the utilisation of starch by the animal.

The ability of an enzyme to degrade resistant starch may be analysed for example by a method developed and disclosed by Megazyme International Ireland Ltd. for the measurement of resistant starch, solubilised starch and total starch content of a sample (Resistant Starch Assay Procedure, AOAC Method 2002.02, AACC Method 32-40).

Accordingly, the PS4 variant polypeptides may be ingested by an animal for beneficial purposes, and may therefore be incorporated into animal feeds.

The invention therefore discloses the use of a PS4 variant polypeptide as a component for use in a feed comprising starch, or for use in a feed improvement composition, in which the PS4 variant polypeptide is capable of degrading resistant starch. The invention also discloses a feed comprising a starch and a PS4 variant polypeptide. The invention further discloses a method of degrading resistant starch in a feed comprising contacting said resistant starch with a PS4 variant polypeptide.

The invention further describes the use of a PS4 variant polypeptide in the preparation of a feed comprising a starch, to degrade resistant starch. Furthermore, the invention discloses the use of a PS4 variant polypeptide in the preparation of a feed to improve the calorific value of said feed. The invention discloses the use of an enzyme in the preparation of a feed to improve animal performance. In a further embodiment, a process for preparing a feed comprising admixing a starch and a PS4 variant polypeptide enzyme is described.

By way of example, use of a component comprising PS4 variant polypeptides and which is capable of degrading resistant starch is advantageous because there is a marked increase in the degradation of starch and/or starch degradation products in an animal. Furthermore, such use is advantageous because there is a marked increase in the digestibility of starch and/or starch degradation products by an animal. Furthermore, such use is advantageous because it provides a means of enhancing the efficiency of deriving energy from a feed by an animal. Furthermore, such use is advantageous because it provides a means to enhance the bioavailability of resistant starch.

Animal feeds for which the PS4 variant polypeptides are suitable for use may be formulated to meet the specific needs of particular animal groups and to provide the necessary carbohydrate, fat, protein and other nutrients in a form that can be metabolised by the animal.

Preferably, the animal feed is a feed for swine or poultry.

As used herein the term 'swine' relates to non-ruminant omnivores such as pigs, hogs or boars. Typically, swine feed includes about 50 percent carbohydrate, about 20 percent protein and about 5% fat. An example of a high energy swine feed is based on corn which is often combined with feed supplements for example, protein, minerals, vitamins and amino acids such as lysine and tryptophan. Examples of swine feeds include animal protein products, marine products, milk products, grain products and plant protein products, all of which may further comprise natural flavourings, artificial flavourings, micro and macro minerals, animal fats, vegetable fats, vitamins, preservatives or medications such as antibiotics.

It is to be understood that where reference is made in the present specification, including the accompanying claims, to 'swine feed' such reference is meant to include "transition" or "starter" feeds (used to wean young swine) and "finishing" or "grower" feeds (used following the transition stage for growth of swine to an age and/or size suitable for market).

As used herein the term 'poultry' relates to fowl such as chickens, broilers, hens, roosters, capons, turkeys, ducks, game fowl, pullets or chicks. Poultry feeds may be referred to as "complete" feeds because they contain all the protein, energy, vitamins, minerals, and other nutrients necessary for proper growth, egg production, and health of the birds. However, poultry feeds may further comprise vitamins, minerals or medications such as coccidiostats (for example Monensin sodium, Lasalocid, Amprolium, Salinomycin, and Sulfaquinoxaline) and/or antibiotics (for example Penicillin, Bacitracin, Chlortetracycline, and Oxytetracycline).

Young chickens or broilers, turkeys and ducks kept for meat production are fed differently from pullets saved for egg production. Broilers, ducks and turkeys have larger bodies and gain weight more rapidly than do the egg-producing types of chickens. Therefore, these birds are fed diets with higher protein and energy levels.

It is to be understood that where reference is made in the present specification, including the accompanying claims, to 'poultry feed' such reference is meant to include "starter" feeds (post-hatching), "finisher", "grower" or "developer" feeds (from 6-8 weeks of age until slaughter size reached) and "layer" feeds (fed during egg production).

Animal feeds may be formulated to meet the animal's nutritional needs with respect to, for example, meat production, milk production, egg production, reproduction and response to stress. In addition, the animal feeds are formulated to improve manure quality.

In a preferred aspect the animal feed contains a raw material such as a legume, for example pea or soy or a cereal, for example wheat, corn (maize), rye or barley. Suitably, the raw material may be potato.

The PS4 variant polypeptides may be used in feeds for animal consumption by the indirect or direct application of the PS4 variant polypeptides to the feed, whether alone or in combination with other ingredients, such as food ingredients.

Typical food ingredients may include any one or more of an additive such as an animal or vegetable fat, a natural or synthetic seasoning, antioxidant, viscosity modifier, essential oil, and/or flavour, dye and/or colorant, vitamin, mineral, natural and/or non-natural amino acid, nutrient, additional enzyme (including genetically manipulated enzymes), a binding agent such as guar gum or xanthum gum, buffer, emulsifier, lubricant, adjuvant, suspending agent, preservative, coating agent or solubilising agent and the like.

Examples of the application methods include, but are not limited to, coating the feed in a material comprising the PS4 variant polypeptide, direct application by mixing the PS4 variant polypeptide with the feed, spraying the PS4 variant polypeptide onto the feed surface or dipping the feed into a preparation of the PS4 variant polypeptide.

The PS4 variant polypeptide is preferably applied by mixing it with a feed or by spraying onto feed particles for animal consumption. Alternatively, the PS4 variant polypeptide may be included in the emulsion of a feed, or the interior of solid products by injection or tumbling.

The PS4 variant polypeptide may be applied to intersperse, coat and/or impregnate a feed. Mixtures with other ingredients may also be used and may be applied separately, simultaneously or sequentially. Chelating agents, binding agents, emulsifiers and other additives such as micro and macro minerals, amino acids, vitamins, animal fats, vegetable fats, preservatives, flavourings, colourings, may be similarly applied to the feed simultaneously (either in mixture or separately) or applied sequentially.

The optimum amount of the PS4 variant polypeptide to be used will depend on the feed to be treated and/or the method of contacting the feed with the PS4 variant polypeptide and/or the intended use for the same. The amount of PS4 variant polypeptide should be in a sufficient amount to be effective to substantially degrade resistant starch following ingestion and during digestion of the feed.

Advantageously, the PS4 variant polypeptide would remain effective following ingestion of a feed for animal consumption and during digestion of the feed until a more complete digestion of the feed is obtained, i.e. an increased calorific value of the feed is released.

The invention discloses in particular combinations of PS4 variant polypeptides with amylases, in particular, maltogenic amylases. Maltogenic alpha-amylase (glucan 1,4-a-maltohydrolase, E.C. 3.2.1.133) is able to hydrolyze amylose and amylopectin to maltose in the alpha-configuration.

A maltogenic alpha-amylase from *Bacillus* (EP 120 693) is commercially available under the trade name Novamyl (Novo Nordisk A/S, Denmark) and is widely used in the baking industry as an anti-staling agent due to its ability to reduce retrogradation of starch. Novamyl is described in detail in International Patent Publication WO 91/04669. The maltogenic alpha-amylase Novamyl shares several characteristics with cyclodextrin glucanotransferases (CGTases), including sequence homology (Henrissat B, Bairoch A; Biochem. J., 316, 695-696 (1996)) and formation of transglycosylation products (Christophersen, C., et al., 1997, Starch, vol. 50, No. 1, 39-45).

In highly preferred embodiments, the invention discloses combinations comprising PS4 variant polypeptides together with Novamyl or any of its variants. Such combinations are useful for food production such as baking. The Novamyl may in particular comprise Novamyl 1500 MG.

Other documents describing Novamyl and its uses include Christophersen, C., Pedersen, S., and Christensen, T., (1993) Method for production of maltose an a limit dextrin, the limit dextrin, and use of the limit dextrin. Denmark, and WO 95/10627. It is further described in U.S. Pat. No. 4,598,048 and U.S. Pat. No. 4,604,355. Each of these documents is hereby incorporated by reference, and any of the Novamyl polypeptides described therein may be used in combinations with any of the PS4 variant polypeptides described here.

Variants, homologues, and mutants of Novamyl may be used for the combinations, provided they retain alpha amylase activity. For example, any of the Novamyl variants disclosed in U.S. Pat. No. 6,162,628, the entire disclosure of which is hereby incorporated by reference, may be used in combination with the PS4 variant polypeptides described here. In particular, any of the polypeptides described in that document, specifically variants of SEQ ID NO: 1 of U.S. Pat. No. 6,162,628 at any one or more positions corresponding to Q13, I16, D17, N26, N28, P29, A30, S32, Y33, G34, L35, K40, M45, P73, V74, D76 N77, D79, N86, R95, N99, I100, H103, Q119, N120, N131, S141, T142, A148, N152, A163, H169, N171, G172, I174, N176, N187, F188, A192, Q201, N203, H220, N234, G236, Q247, K249, D261, N266, L268, R272, N275, N276, V279, N280, V281, D285, N287, F297, Q299, N305, K316, N320, L321, N327, A341, N342, A348, Q365, N371, N375, M378, G397, A381, F389, N401, A403, K425, N436, S442, N454, N468, N474, S479, A483, A486, V487, S493, T494, S495, A496, S497, A498, Q500, N507, I510, N513, K520, Q526, A555, A564, S573, N575, Q581, S583, F586, K589, N595, G618, N621, Q624, A629, F636, K645, N664 and/or T681 may be used.

The invention makes use of a PS4 variant nucleic acid, and the amino acid sequences of such PS4 variant nucleic acids are encompassed by the methods and compositions described here.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The PS4 variant enzyme described here may be used in conjunction with other enzymes. Thus the invention further discloses a combination of enzymes wherein the combination comprises a PS4 variant polypeptide enzyme described here and another enzyme, which itself may be another PS4 variant polypeptide enzyme.

As noted above, the invention disclose nucleotide sequences encoding the PS4 variant enzymes having the specific properties described.

The term "nucleotide sequence" or "nucleic acid sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" as used in this document includes genomic DNA, cDNA, synthetic DNA, and RNA. Preferably it means DNA, more preferably cDNA sequence coding for a PS4 variant polypeptide.

Typically, the PS4 variant nucleotide sequence is prepared using recombinant DNA techniques (i.e. recombinant DNA). However, in an alternative embodiment, the nucleotide sequence could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

A nucleotide sequence encoding either an enzyme which has the specific properties as defined herein (e.g., a PS4 variant polypeptide) or an enzyme which is suitable for modification, such as a parent enzyme, may be identified and/or isolated and/or purified from any cell or organism producing said enzyme. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme or a part of the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for enzyme (i.e. maltose), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al., (1981) *Tetrahedron Letters* 22, p 1859-1869, or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (Science (1988) 239, pp 487-491).

The invention further describes the use of variants, homologues and derivatives of any amino acid sequence of an enzyme or of any nucleotide sequence encoding such an enzyme, such as a PS4 variant polypeptide or a PS4 variant nucleic acid. Unless the context dictates otherwise, the term "PS4 variant nucleic acid" should be taken to include each of the nucleic acid entities described below, and the term "PS4 variant polypeptide" should likewise be taken to include each of the polypeptide or amino acid entities described below.

Here, the term "homologue" means an entity having a certain homology with the subject amino acid sequences and the subject nucleotide sequences. Here, the term "homology" can be equated with "identity".

In the present context, a homologous sequence is taken to include an amino acid sequence which may be at least 75, 80, 85 or 90% identical, preferably at least 95, 96, 97, 98 or 99% identical to the subject sequence. Typically, the homologues will comprise the same active sites etc. as the subject amino acid sequence. Although homology can also be considered in terms of similarity (i.e. amino acid residues having similar chemical properties/functions), in the context of this document it is preferred to express homology in terms of sequence identity.

In the present context, an homologous sequence is taken to include a nucleotide sequence which may be at least 75, 80, 85 or 90% identical, preferably at least 95, 96, 97, 98 or 99% identical to a nucleotide sequence encoding a PS4 variant polypeptide enzyme (such as a PS4 variant nucleic acid). Typically, the homologues will comprise the same sequences that code for the active sites etc as the subject sequence. Although homology can also be considered in terms of similarity (i.e. amino acid residues having similar chemical properties/functions), in the context of this document it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387). Examples of other software than can perform sequence comparisons include, but are not limited to, the BLAST package (see Ausubel et al., 1999 Short Protocols in Molecular Biology, $4^{th}$ Ed—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60).

However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids can be grouped together based on the properties of their side chain alone. However it is more useful to include mutation data as well. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation"

*Comput. Appl Biosci.* 9: 745-756) (Taylor W. R. (1986) "The classification of amino acid conservation" *J. Theor. Biol.* 119; 205-218). Conservative substitutions may be made, for example according to the table below which describes a generally accepted Venn diagram grouping of amino acids.

| Set | | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

The invention further discloses sequences comprising homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

The nucleotide sequences described here, and suitable for use in the methods and compositions described here (such as PS4 variant nucleic acids) may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of this document, it is to be understood that the nucleotide sequences described herein may be modified by any method available in the art. Such modifications may be carried out in order to enhance the in vivo activity or life span of nucleotide sequences.

The invention further describes the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the PS4 variant sequences may be obtained in a number of ways.

Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other species, and probing such libraries with probes comprising all or part of any one of the sequences in the attached sequence listings under conditions of medium to high stringency. Similar considerations apply to obtaining species homologues and allelic variants of the polypeptide or nucleotide sequences described here.

Variants and strain/species homologues may also be obtained using degenerate PCR which will use primers designed to target sequences within the variants and homologues encoding conserved amino acid sequences. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The polynucleotides (nucleotide sequences) such as the PS4 variant nucleic acids described in this document may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides.

Polynucleotides such as DNA polynucleotides and probes may be produced recombinantly, synthetically, or by any means available to those of skill in the art. They may also be cloned by standard techniques. In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector. Preferably, the variant sequences etc. are at least as biologically active as the sequences presented herein.

As used herein "biologically active" refers to a sequence having a similar structural function (but not necessarily to the same degree), and/or similar regulatory function (but not necessarily to the same degree), and/or similar biochemical function (but not necessarily to the same degree) of the naturally occurring sequence.

The invention further describes sequences that are complementary to the nucleic acid sequences of PS4 variants or sequences that are capable of hybridising either to the PS4 variant sequences or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies. Therefore, the use of nucleotide sequences that are capable of hybridising to the sequences that are complementary to the sequences presented herein, or any derivative, fragment or derivative thereof are disclosed.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 50° C. and 0.2×SSC {1×SSC=0.15 M NaCl, 0.015 M Na$_3$citrate pH 7.0}) to the nucleotide sequences presented herein. More preferably, the term "variant" encompasses sequences that are complementary to sequences that are capable of hybridising under high stringent conditions (e.g. 65° C. and 0.1×SSC {1×SSC=0.15 M NaCl, 0.015 M Na$_3$citrate pH 7.0}) to the nucleotide sequences presented herein.

The invention further discloses nucleotide sequences that can hybridise to the nucleotide sequences of PS4 variants (including complementary sequences of those presented herein), as well as nucleotide sequences that are complementary to sequences that can hybridise to the nucleotide sequences of PS4 variants (including complementary sequences of those presented herein). The invention further describes polynucleotide sequences that are capable of hybridising to the nucleotide sequences presented herein under conditions of intermediate to maximal stringency.

In a preferred aspect, the invention discloses nucleotide sequences that can hybridise to the nucleotide sequence of a PS4 variant nucleic acid, or the complement thereof, under stringent conditions (e.g. 50° C. and 0.2×SSC). More preferably, the nucleotide sequences can hybridise to the nucleotide sequence of a PS4 variant, or the complement thereof, under high stringent conditions (e.g. 65° C. and 0.1×SSC).

Once an enzyme-encoding nucleotide sequence has been isolated, or a putative enzyme-encoding nucleotide sequence has been identified, it may be desirable to mutate the sequence in order to prepare an enzyme. Accordingly, a PS4 variant sequence may be prepared from a parent sequence. Mutations may be introduced using synthetic oligonucleotides. These oligonucleotides contain nucleotide sequences flanking the desired mutation sites.

A suitable method is disclosed in Morinaga et al., (*Biotechnology* (1984) 2, p 646-649). Another method of introducing mutations into enzyme-encoding nucleotide sequences is described in Nelson and Long (*Analytical Biochemistry* (1989), 180, p 147-151). A further method is described in Sarkar and Sommer (*Biotechniques* (1990), 8, p 404-407—"The megaprimer method of site directed mutagenesis").

In one aspect the sequence for use in the methods and compositions described here is a recombinant sequence—i.e. a sequence that has been prepared using recombinant DNA techniques. These recombinant DNA techniques are within the capabilities of a person of ordinary skill in the art. Such techniques are explained in the literature, for example, J. Sambrook, E. F. Fritsch, and T. Maniatis, 1989, *Molecular Cloning: A Laboratory Manual*, Second Edition, Books 1-3, Cold Spring Harbor Laboratory Press.

In one aspect the sequence for use in the methods and compositions described here is a synthetic sequence—i.e. a sequence that has been prepared by in vitro chemical or enzymatic synthesis. It includes, but is not limited to, sequences made with optimal codon usage for host organisms—such as the methylotrophic yeasts *Pichia* and *Hansenula*.

The nucleotide sequence for use in the methods and compositions described here may be incorporated into a recombinant replicable vector. The vector may be used to replicate and express the nucleotide sequence, in enzyme form, in and/or from a compatible host cell. Expression may be controlled using control sequences eg. regulatory sequences. The enzyme produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

The PS4 polynucleotides and nucleic acids may include DNA and RNA of both synthetic and natural origin which DNA or RNA may contain modified or unmodified deoxy- or dideoxy-nucleotides or ribonucleotides or analogs thereof. The PS4 nucleic acid may exist as single- or double-stranded DNA or RNA, an RNA/DNA heteroduplex or an RNA/DNA copolymer, wherein the term "copolymer" refers to a single nucleic acid strand that comprises both ribonucleotides and deoxyribonucleotides. The PS4 nucleic acid may even be codon optimised to further increase expression.

The term "synthetic", as used herein, is defined as that which is produced by in vitro chemical or enzymatic synthesis. It includes but is not limited to PS4 nucleic acids made with optimal codon usage for host organisms such as the methylotrophic yeasts *Pichia* and *Hansenula*.

Polynucleotides, for example variant PS4 polynucleotides described here, can be incorporated into a recombinant replicable vector. The vector may be used to replicate the nucleic acid in a compatible host cell. The vector comprising the polynucleotide sequence may be transformed into a suitable host cell. Suitable hosts may include bacterial, yeast, insect and fungal cells.

The term "transformed cell" includes cells that have been transformed by use of recombinant DNA techniques. The transformation typically occurs by insertion of one or more nucleotide sequences into a cell that is to be transformed. The inserted nucleotide sequence may be a heterologous nucleotide sequence (i.e. is a sequence that is not natural to the cell that is to be transformed. In addition, or in the alternative, the inserted nucleotide sequence may be an homologous nucleotide sequence (i.e. is a sequence that is natural to the cell that is to be transformed)—so that the cell receives one or more extra copies of a nucleotide sequence already present in it.

Thus in a further embodiment, the invention provides a method of making PS4 variant polypeptides and polynucleotides by introducing a polynucleotide into a replicable vector, introducing the vector into a compatible host cell, and growing the host cell under conditions which bring about replication of the vector. The vector may be recovered from the host cell.

The PS4 nucleic acid may be operatively linked to transcriptional and translational regulatory elements active in a host cell of interest. The PS4 nucleic acid may also encode a fusion protein comprising signal sequences such as, for example, those derived from the glucoamylase gene from *Schwanniomyces occidentalis*, α-factor mating type gene from *Saccharomyces cerevisiae* and the TAKA-amylase from *Aspergillus oryzae*. Alternatively, the PS4 nucleic acid may encode a fusion protein comprising a membrane binding domain.

The PS4 nucleic acid may be expressed at the desired levels in a host organism using an expression vector.

An expression vector comprising a PS4 nucleic acid can be any vector which is capable of expressing the gene encoding PS4 nucleic acid in the selected host organism, and the choice of vector will depend on the host cell into which it is to be introduced. Thus, the vector can be an autonomously replicating vector, i.e. a vector that exists as an episomal entity, the replication of which is independent of chromosomal replication, such as, for example, a plasmid, a bacteriophage or an episomal element, a minichromosome or an artificial chromosome. Alternatively, the vector may be one which, when introduced into a host cell, is integrated into the host cell genome and replicated together with the chromosome.

The expression vector typically includes the components of a cloning vector, such as, for example, an element that permits autonomous replication of the vector in the selected host organism and one or more phenotypically detectable markers for selection purposes. The expression vector normally comprises control nucleotide sequences encoding a promoter, operator, ribosome binding site, translation initiation signal and optionally, a repressor gene or one or more activator genes. Additionally, the expression vector may comprise a sequence coding for an amino acid sequence capable of targeting the PS4 variant polypeptide to a host cell organelle such as a peroxisome or to a particular host cell compartment. Such a targeting sequence includes but is not limited to the sequence SKL. In the present context, the term "expression signal" includes any of the above control sequences, repressor or activator sequences. For expression under the direction of control sequences, the nucleic acid sequence the PS4 variant polypeptide is operably linked to the control sequences in proper manner with respect to expression.

Preferably, a polynucleotide in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators. The control sequences may in particular comprise promoters.

In the vector, the nucleic acid sequence encoding for the variant PS4 polypeptide is operably combined with a suitable promoter sequence. The promoter can be any DNA sequence having transcription activity in the host organism of choice and can be derived from genes that are homologous or heterologous to the host organism.

Examples of suitable promoters for directing the transcription of the modified nucleotide sequence, such as PS4 nucleic acids, in a bacterial host include the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase gene (amyQ), the promoters of the *Bacillus subtilis* xylA and xylB genes, the promoter of the *Bacillus subtilis* aprE gene and a promoter derived from a *Lactococcus* sp.-derived promoter including the P170 promoter. When the gene encoding the PS4 variant polypeptide is expressed in a bacterial species such as *E. coli*, a suitable promoter can be selected, for example, from a bacteriophage promoter including a T7 promoter and a phage lambda promoter.

For transcription in a fungal species, examples of useful promoters are those derived from the genes encoding the, *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *Aspergillus oryzae* alkaline protease, *Aspergillus oryzae* triose phosphate isomerase or *Aspergillus nidulans* acetamidase.

Examples of suitable promoters for the expression in a yeast species include but are not limited to the Gal 1 and Gal 10 promoters of *Saccharomyces cerevisiae* and the *Pichia pastoris* AOX1 or AOX2 promoters.

Examples of suitable bacterial host organisms are gram positive bacterial species such as Bacillaceae including *Bacillus clausii, Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus lautus, Bacillus megaterium* and *Bacillus thuringiensis, Streptomyces* species such as *Streptomyces murinus*, lactic acid bacterial species including *Lactococcus* spp. such as *Lactococcus lactis, Lactobacillus* spp. including *Lactobacillus reuteri, Leuconostoc* spp., *Pediococcus* spp. and *Streptococcus* spp. Alternatively, strains of a gram-negative bacterial species belonging to Enterobacteriaceae including *E. coli*, or to Pseudomonadaceae can be selected as the host organism.

A suitable yeast host organism can be selected from the biotechnologically relevant yeasts species such as but not limited to yeast species such as *Pichia* sp., *Hansenula* sp or *Kluyveromyces, Yarrowinia* species or a species of *Saccharomyces* including *Saccharomyces cerevisiae* or a species belonging to *Schizosaccharomyce* such as, for example, *S. Pombe* species.

Preferably a strain of the methylotrophic yeast species *Pichia pastoris* is used as the host organism. Preferably the host organism is a *Hansenula* species.

Suitable host organisms among filamentous fungi include species of *Aspergillus*, e.g. *Aspergillus niger, Aspergillus oryzae, Aspergillus tubigensis, Aspergillus awamori* or *Aspergillus nidulans*. Alternatively, strains of a *Fusarium* species, e.g. *Fusarium oxysporum* or of a *Rhizomucor* species such as *Rhizomucor miehei* can be used as the host organism. Other suitable strains include *Thermomyces* and *Mucor* species.

Suitable fungal host organisms may also include *Trichoderma* spp (especially *Trichoderma reesei* formerly *Trichoderma longibrachiatum*; also known as *Hypocrea jecorina*).

Host cells comprising polynucleotides may be used to express polypeptides, such as variant PS4 polypeptides, fragments, homologues, variants or derivatives thereof. Host cells may be cultured under suitable conditions which allow expression of the proteins. Expression of the polypeptides may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Polypeptides can be extracted from host cells by a variety of techniques known in the art, including enzymatic, chemical and/or osmotic lysis and physical disruption. Polypeptides may also be produced recombinantly in an in vitro cell-free system, such as the TnT™ (Promega) rabbit reticulocyte system.

The invention will now be further described by way of the following non-limiting examples.

EXAMPLES

Example 1

Cloning of PS4

Cloning of *Pseudomonas sacharophila* non-maltogenic exoamylase PS4 and the generation of plasmids pCSmta and pCSmta-SBD is described in WO 2005/003339, particularly Example 1.

Site directed mutagenesis (SDM) may be conducted using the methods described in WO 2005/003339, particularly in Example 2 of that document.

Example 2

Multi SDM

The PS4 variants were generated using a QuikChange® Multi Site Directed Mutagenesis Kit (Stratagene) according to the manufactures protocol with some modifications as described.

Step 1: Mutant Strand Synthesis Reaction (PCR)

Inoculate 3 ml. LB (22 g/l Lennox L Broth Base, Sigma)+ antibiotics (0.05 μg/ml kanamycin, Sigma) in a 10 ml Falcon tube
  Incubate o/n 37° C., ca. 200 rpm.
  Spin down the cells by centrifugation (5000 rpm/5 min)
  Poor off the medium
  Prepare ds-DNA template using QIAGEN Plasmid Mini Purification Protocol
  1. The mutant strand synthesis reaction for thermal cycling was prepared as follow:

PCR Mix:

| | |
|---|---|
| 2.5 μl | 10X QuickChange ® Multi reaction buffer |
| 0.75 μl | QuickSolution |
| X μl | Primers { primer length 28 – 35 bp → 10 pmol; primer length 24 – 27 bp → 7 pmol; primer length 20 – 23 bp → 5 pmol } |
| 1 μl | dNTP mix |
| X μl | ds-DNA template (200 ng) |
| 1 μl | QuickChange ® Multi enzyme blend (2.5 U/μl) (PfuTurbo ® DNA polymerase) |
| X μl | dH$_2$O (to a final volume of 25 μl) |

Mix all components by pipetting and briefly spin down the reaction mixtures.

2. Cycle the reactions using the following parameters:
  35 cycles of denaturation (96° C./1 min)
    primer annealing (62.8° C./1 min)
    elongation (65° C./15 min)
    then hold at 4° C.
  Preheat the lid of the PCR machine to 105° C. and the plate to 95° C. before the PCR tubes are placed in the machine (eppendorf thermal cycler).

Step 2: Dpn I Digestion
  1. Add 2 μl Dpn I restriction enzyme (10 U/μl) to each amplification reaction, mix by pipetting and spin down mixture.
  2. Incubate at 37° C. for ~3 hr.

Step 3: Transformation of XL10-Gold® Ultracompetent Cells
  1. Thaw XL10-Gold cells on ice. Aliquot 45 μl cells per mutagenesis reaction to prechilled Falcon tubes.
  2. Turn on the waterbath (42° C.) and place a tube with NZY$^+$ broth in the bath to preheat.
  3. Add 2 l β-mercaptoethanol mix to each tube. Swirl and tap gently and incubate 10 min on ice, swirling every 2 min.
  4. Add 1.5 μl Dpn I-treated DNA to each aliquot of cells, swirl to mix and incubate on ice for 30 min.
  5. Heat-pulse the tubes in 42° C. waterbath for 30 s and place on ice for 2 min.
  6. Add 0.5 ml preheated NZY$^+$ broth to each tube and incubate at 37° C. for 1 hr with shaking at 225-250 rpm.
  7. Plate 200 μl of each transformation reaction on LB plates (33.6 g/l Lennox L Agar, Sigma) containing 1% starch and 0.05 μg/ml kanamycin
  8. Incubate the transformation plates at 37° C. overnight.

"SDM" primers may be used to modify the specified positions using a method described in Example 2 of WO 2005/003339. "MSDM" primers may be used with the method described in Example 3 herein.

| Mutation | Purpose | modification | Strand | 5' Oligo Sequence 3' |
|---|---|---|---|---|
| N33Y, D34N | MSDM | 5' phosphate | + | GCGAAGCGCCCTACAACTGGTACAAC |
| G121F | MSDM | 5' phosphate | + | CCAATCACATGAACCGCttcTACCCGGACAAGGAG |

-continued

| Mutation | Purpose | modification | Strand | 5' Oligo Sequence 3' |
|---|---|---|---|---|
| G134R | SDM | | + | CTGCCGGCCGGCCAGcGCTTCTGGCG |
| G134R- | SDM | | − | CGCCAGAAGCGCTGGCCGGCCGGCAG |
| A141P | MSDM | 5' phosphate | + | CGCAACGACTGCGCCGACCCGGG |
| Y146G | MSDM | 5' phosphate | + | GATCCGGGCAACggcCCCAACGACTGCG |
| I157L | SDM | | + | GACGGTGACCGCTTCcTgGGCGGCGAGTCG |
| I157L- | SDM | | − | CGACTCGCCGCCCAGGAAGCGGTCACCGTC |
| S161A | MSDM | 5' phosphate | + | GGGCGGCGAGgcgGACCTGAACA |
| L178F, A179T | MSDM | 5' phosphate | + | CGCGACGAGTTTACCAACCTGCG |
| G223E | MSDM | 5' phosphate | + | GGCGAGCTGTGGAAAgagCCTTCTGAATATCCGAG |
| S229P | MSDM | 5' phosphate | + | GCCTTCTGAATATCCGccgTGGGACTGGCGCAAC |
| H272Q | MSDM | 5' phosphate | + | CCGACTGGAAGcagGGCCTCAATGGC |
| G303E | MSDM | 5' phosphate | + | CCGGGCAGAACgaaGGCCAGCACCTGTG |
| H307L | SDM | | + | GAACGGCGGCCAGCACctgTGGGCGCTGCAG |
| H307L- | SDM | | − | CTGCAGCGCCCACAGGTGCTGGCCGCCGTTC |
| A309P | MSDM | 5' phosphate | + | GCACCTGTGGccgCTGCAGGACG |
| S334P, D343E | SDM | | + | GTACTGGccgCACATGTACGACTGGGGCTACGGCgaaTTCATC |
| S334P, D343E- | SDM | | − | GATGAATTCGCCGTAGCCCCAGTCGTACATGTGCGGCCAGTAC |

Example 3

Transformation into *Bacillus subtilis* (Protoplast Transformation)

*Bacillus subtilis* (strain DB104A; Smith et al. 1988; Gene 70, 351-361) is transformed with the mutated plasmids according to the following protocol.

A. Media for Protoplasting and Transformation

| | |
|---|---|
| 2 × SMM | per litre: 342 g sucrose (1 M); 4.72 g sodium maleate (0.04 M); 8:12 g MgCl$_2$, 6H$_2$0 (0.04 M); pH 6.5 with concentrated NaOH. Distribute in 50-ml portions and autoclave for 10 min. |
| 4 × YT (1/2 NaCl) | 2 g Yeast extract + 3.2 g Tryptone + 0.5 g NaCl per 100 ml. mix equal volumes of 2 × SMM and 4 × YT. 10 g polyethyleneglycol 6000 (BDH) or 8000 (Sigma) in 25 ml 1 × SMM (autoclave for 10 min.). |
| SMMP | |
| PEG | |

B. Media for Plating/Regeneration

| | |
|---|---|
| agar | 4% Difco minimal agar. Autoclave for 15 min. |
| sodium succinate | 270 g/l (1 M), pH 7.3 with HCl. Autoclave for 15 min. |
| phosphate buffer | 3.5 g K$_2$HPO$_4$ + 1.5 g KH$_2$PO$_4$ per 100 ml. Autoclave for 15 min. |
| MgCl$_2$ | 20.3 g MgCl$_2$, 6H$_2$O per 100 ml (1 M). |
| casamino acids | 5% (w/v) solution. Autoclave for 15 min. |
| yeast extract | 10 g per 100 ml, autoclave for 15 min. |
| glucose | 20% (w/v) solution. Autoclave for 10 min. |

DM3 regeneration medium: mix at 60 C (waterbath; 500-ml bottle):

250 ml sodium succinate
50 ml casamino acids
25 ml yeast extract
50 ml phosphate buffer
15 ml glucose
10 ml MgCl$_2$
100 ml molten agar Add appropriate antibiotics: chloramphenicol and tetracycline, 5 ug/ml; erythromycin, 1 ug/ml. Selection on kanamycin is problematic in DM3 medium: concentrations of 250 ug/ml may be required.

C. Preparation of Protoplasts

1. Use detergent-free plastic or glassware throughout.
2. Inoculate 10 ml of 2×YT medium in a 100-ml flask from a single colony. Grow an overnight culture at 25-30 C in a shaker (200 rev/min).
3. Dilute the overnight culture 20 fold into 100 ml of fresh 2×YT medium (250-ml flask) and grow until OD$_{600}$=0.4-0.5 (approx. 2 h) at 37 C in a shaker (200-250 rev/min).
4. Harvest the cells by centrifugation (9000 g, 20 min, 4 C).
5. Remove the supernatant with pipette and resuspend the cells in 5 ml of SMMP+5 mg lysozyme, sterile filtered.
6. Incubate at 37 C in a waterbath shaker (100 rev/min).

After 30 min and thereafter at 15 min intervals, examine 25 ul samples by microscopy. Continue incubation until 99% of the cells are protoplasted (globular appearance). Harvest the protoplasts by centrifugation (4000 g, 20 min, RT) and pipet off the supernatant. Resuspend the pellet gently in 1-2 ml of SMMP.

The protoplasts are now ready for use. (Portions (e.g. 0.15 ml) can be frozen at −80 C for future use (glycerol addition is not required). Although this may result in some reduction of transformability, 106 transformants per ug of DNA can be obtained with frozen protoplasts).

D. Transformation

1. Transfer 450 ul of PEG to a microtube.
2. Mix 1-10 ul of DNA (0.2 ug) with 150 ul of protoplasts and add the mixture to the microtube with PEG. Mix immediately, but gently.
3. Leave for 2 min at RT, and then add 1.5 ml of SMMP and mix.
4. Harvest protoplasts by microfuging (10 min, 13.000 rev/min (10-12.000 g)) and pour off the supernatant. Remove the remaining droplets with a tissue.

Add 300 ul of SMMP (do not vortex) and incubate for 60-90 min at 37 C in a waterbath shaker (100 rev/min) to allow for expression of antibiotic resistance markers. (The protoplasts become sufficiently resuspended through the shaking action of the waterbath.). Make appropriate dilutions in 1×SSM and plate 0.1 ml on DM3 plates Example 4

Fermentation of PS4 Variants in Shake Flasks

The shake flask substrate is prepared as follows:

| Ingredient | %(w/v) |
| --- | --- |
| Water | — |
| Yeast extract | 2 |
| Soy Flour | 2 |
| NaCl | 0.5 |
| Dipotassium phosphate | 0.5 |
| Antifoam agent | 0.05 |

The substrate is adjusted to pH 6.8 with 4N sulfuric acid or sodium hydroxide before autoclaving. 100 ml of substrate is placed in a 500 ml flask with one baffle and autoclaved for 30 minutes. Subsequently, 6 ml of sterile dextrose syrup is added. The dextrose syrup is prepared by mixing one volume of 50% w/v dextrose with one volume of water followed by autoclaving for 20 minutes.

The shake flasks are inoculated with the variants and incubated for 24 hours at 35° C./180 rpm in an incubator. After incubation cells are separated from broth by centrifugation (10.000×g in 10 minutes) and finally, the supernatant is made cell free by microfiltration at 0.2 μm. The cell free supernatant is used for assays and application tests.

Example 5

Amylase Assays

Betamyl Assay

One Betamyl unit is defined as activity degrading 0.0351 mmole per 1 min. of PNP-coupled maltopentaose so that 0.0351 mmole PNP per 1 min. can be released by excess a-glucosidase in the assay mix. The assay mix contains 50 ul 50 mM Na-citrate, 5 mM CaCl2, pH 6.5 with 25 ul enzyme sample and 25 ul Betamyl substrate (Glc5-PNP and a-glucosidase) from Megazyme, Ireland (1 vial dissolved in 10 ml water). The assay mix is incubated for 30 min. at 40 C and then stopped by adding 150 ul 4% Tris. Absorbance at 420 nm is measured using an ELISA-reader and the Betamyl activity is calculate based on Activity=A420*d in Betamyl units/ml of enzyme sample assayed.

Endo-Amylase Assay

The endo-amylase assay is identical to the Phadebas assay run according to manufacturer (Pharmacia & Upjohn Diagnostics AB).

Exo-Specificity

The ratio of exo-amylase activity to Phadebas activity was used to evaluate exo-specificity.

Specific Activity

For the pSac-D14, pSac-D20 and pSac-D34 variants an average specific activity of 10 Betamyl units per microgram of purified protein is found measured according to Bradford (1976; Anal. Biochem. 72, 248). This specific activity is used for based on activity to calculate the dosages used in the application trials.

Example 6

Half-Life Determination t½ is defined as the time (in minutes) during which half the enzyme activity is inactivated under defined heat conditions. In order to determine the half life of the enzyme, the sample is heated for 1-40 minutes at constant temperatures of 60° C. to 90° C. The half life is calculated based on the residual Betamyl assay.

Procedure: In an Eppendorf vial, 1000 μl buffer is preheated for at least 10 minutes at 60° C. or higher. The heat treatment of the sample is started addition of 100 μl of the sample to the preheated buffer under continuous mixing (800 rpm) of the Eppendorf vial in an heat incubator (Termomixer comfort from Eppendorf). After 0, 2, 4, 6, 8 and 9 minutes of incubation, the treatment is stopped by transferring 45 μl of the sample to 1000 μl of the buffer equilibrated at 20° C. and incubating for one minute at 1500 rpm and at 20° C. The residual activity is measured with the Betamyl assay.

Calculation: Calculation of t½ is based on the slope of log 10 (the base-10 logarithm) of the residual Betamyl activity versus the incubation time. t½ is calculated as Slope/0.301=t½.

Example 7

Model System Baking Tests

The doughs are made in the Farinograph at 30.0° C. 10.00 g reformed flour is weighed out and added in the Farinograph; after 1 min. mixing the reference/sample (reference=buffer or water, sample=enzyme+buffer or water) is added with a sterile pipette through the holes of the kneading vat. After 30 sec. the flour is scraped off the edges—also through the holes of the kneading vat. The sample is kneaded for 7 min.

A test with buffer or water is performed on the Farinograph before the final reference is run. FU should be 400 on the reference, if it is not, this should be adjusted with, for example, the quantity of liquid. The reference/sample is removed with a spatula and placed in the hand (with a disposable glove on it), before it is filled into small glass tubes (of approx. 4.5 cm's length) that are put in NMR tubes and corked up. 7 tubes per dough are made.

When all the samples have been prepared, the tubes are placed in a (programmable) water bath at 33° C. (without corks) for 25 min. and hereafter the water bath is set to stay for 5 min. at 33° C., then to heated to 98° C. over 56 min. (1.1° C. per minute) and finally to stay for 5 min. at 96° C.

The tubes are stored at 20.0° C. in a thermo cupboard. The solid content of the crumb was measured by proton NMR using a Bruker NMS 120 Minispec NMR analyser at day 1, 3 and 7 as shown for crumb samples prepared with 0, 05, 1 and 2 ppm pSac-D34 in FIG. 2. The lower increase in solid content over time represents the reduction in amylopectin retrogradation. After 7 days of storage at 20.0° C. in a thermo cupboard 10-20 mg samples of crumb weighed out and placed in 40 μl aluminium standard DSC capsules and kept at 20° C.

The capsules are used for Differential Scanning Calorimetry on a Mettler Toledo DSC 820 instrument. As parameters are used a heating cycle of 20-95° C. with 10° C. per min. heating and Gas/flow: $N_2$/80 ml per min. The results are analysed and the enthalpy for melting of retrograded amylopectin is calculated in J/g.

Example 8

Antistaling Effects

Model bread crumbs are prepared and measured according to Example 7. PS4 variants show a strong reduction of the amylopectin retrogradation after baking as measured by Differential Scanning Calorimetry in comparison to the control. The PS4 variants show a clear dosage effect.

Example 9

Recipe for Baking Trials

Baking trials were carried out with a standard white bread sponge and dough recipe for US toast. The sponge dough is prepared from 1400 g of flour "Gold Medal" from General Mills, USA, 800 g of water, 40 g of rape seed oil, 7.5 g GRINDSTED™ SSL P55 Veg, 10 g emulsifier DIMODAN™ PH200 and 60 g of compressed yeast. The sponge is mixed for 1 min. at low speed and subsequently 3 min. at speed 2 on a Hobart spiral mixer. The sponge is subsequently fermented for 3 hours at 25° C., 85% RH.

Thereafter, 600 g of "Gold Medal" flour, 18 g of compressed yeast, 5 g of calcium propionate, 160 g of sucrose, 5 g of calcium propionate, 432 g of water and ascorbic acid (60 ppm final concentration) and ADA (azodicarbonamide; 40 ppm final concentration) are added to the sponge. The resulting dough is mixed for 1 min. at low speed and then 2 min. on high speed on a Diosna mixer. Then 30 g of salt is added to the dough.

The dough is rested for 5 min. at ambient temperature, and then 550 g dough pieces are scaled, moulded on Glimek sheeter with the settings 1:4, 2:4, 3:15, 4:12 and width 8 on both sides and transferred to a baking form. After 65 min. proofing at 43° C. at 95% RH the doughs are baked for 26 min. at 200° C. in an MIWE oven.

Example 10

Control of Volume of Danish Rolls

Danish Rolls are prepared from a dough based on 2000 g Danish reform flour (from Cerealia), 120 g compressed yeast, 32 g salt, and 32 g sucrose. Water is added to the dough according to prior water optimisation.

The dough is mixed on a Diosna mixer (2 min. at low speed and 5 min. at high speed). The dough temperature after mixing is kept at 26° C. 1350 g dough is scaled and rested for 10 min. in a heating cabinet at 30° C. The rolls are moulded on a Fortuna molder and proofed for 45 min. at 34° C. and at 85% relative humidity. Subsequently the rolls are baked in a Bago 2 oven for 18 min. at 250° C. with steam in the first 13 seconds. After baking the rolls are cooled for 25 min. before weighing and measuring of volume.

The rolls are evaluated regarding crust appearance, crumb homogeneity, capping of the crust, ausbund and specific volume (measuring the volume with the rape seed displacement method).

Based on these criteria it is found that the PS4 variants increase the specific volume and improve the quality parameters of Danish rolls. Thus PS4 variants are able to control the volume of baked products.

Example 11

Protocol for Evaluation of Firmness, Resilience and Cohesiveness

Texture Profile Analysis of Bread

Firmness, resilience and cohesiveness are determined by analysing bread slices by Texture Profile Analysis using a Texture Analyser From Stable Micro Systems, UK. Calculation of firmness and resilience is done according to preset standard supplied by Stable Micro System, UK. The probe used is aluminium 50 mm round.

Bread is sliced with the width of 12.5 mm. The slices are stamped out to a circular piece with a diameter of 45 mm and measured individually.

The following settings are used:
Pre Test Speed: 2 mm/s
Test Speed: 2 mm/s
Post Test Speed: 10 mm/s
Rupture Test Distance: 1%
Distance: 40%
Force: 0.098 N
Time: 5.00 sec
Count: 5
Load Cell: 5 kg
Trigger Type Auto −0.01 N The mode of compression is a modification to the one used in Standard method AACC 74-09. The sample is compressed twice in the test. FIG. 1 shows an example of a curve from the Texture Analyser.

Example 12

Protocol for Evaluation of Firmness

Firmness is determined at 40% compression during the first compression. The figure is the force needed to compress the slice to 40% of the total thickness. The lower the value, the softer the bread. The firmness is expressed as a pressure, for example, in hPa.

This assay may be referred to as the "Firmness Evaluation Protocol".

Example 13

Protocol for Evaluation of Resilience

Area under the curve is a measure of work applied during the test. The area under the curve in the compression part (A1) and the withdrawal part (A2) during the first compression are shown in FIG. 1.

The ratio between A1 and A2 is defined as the resilience of the sample, and is expressed as Resilience Units. True elastic material will give a symmetric curve, as the force applied during the first part will be equal to the force in the second part. For bread and bread-like material, A2 is normally smaller than A2 due to disturbance of the structure during compression. Hence, resilience is always lower than 1.

This assay may be referred to as the "Resilience Evaluation Protocol".

Example 14

Protocol for Evaluation of Cohesiveness

The cohesiveness is defined as the ratio between the area under second compression to the area under first compression (A3/A1+A2), and is expressed as Cohesiveness Units. It is a measure of the decay of the sample during compression. The higher the ability of the sample to regain its shape after first compression the closer the value will be to 1. For bread and bread-like material cohesiveness is always lower than 1.

This assay may be referred to as the "Cohesiveness Evaluation Protocol".

Example 15

Enhanced Exo-Specificity of PS4 Variant Polypeptide with Mutation 272Q

A PS4 variant polypeptide designated pMD229 having amino acid mutations at N33Y D34N G121F G134R A141P Y146G I157L S161A L178F A179T G223E S229P H272Q G303E H307L A309P S334P is tested for exo-specificity. This polypeptide displays improved exo-specificity as shown in the table below.

| Variant | t½-85 | Betamyl/ Phadebas | Mutations |
|---|---|---|---|
| pMD172 | | 446 | N33Y D34N G121F G134R A141P Y146G I157L S161A L178F A179T G223E S229P G303E H307L A309P S334P |
| pMD229 | | 583 | N33Y D34N G121F G134R A141P Y146G I157L S161A L178F A179T G223E S229P H272Q G303E H307L A309P S334P |

The halt-life t½-85 is determined according to Example 6, after gel-titration of the samples with PD-10 columns (from Amersham Biosciences) using a 50 mM sodium citrate, 5 mM $CaCl_2$, pH 6.5 buffer.

Example 16

Firmness Effects of pMD229, 248, 253 and 271 in Baking Trials

Baking trials are carried out with a standard white bread sponge and dough recipe for US toast as described in Example 10. Samples of pMD229, 248, 253 and 271 were applied in dosages of the interval 0.1 to 20 mg/kg of flour. The enzyme samples are added to the dough after sponge fermentation together with the remaining ingredients.

Firmness measurements show that the enzymes significantly reduce the firmness development from day 1 to day 7 and show a higher effect with increasing enzyme dosage.

Example 17

Improved Handling Properties of Food Products Treated with PS4 Variant Polypeptides: Firmness Bread is baked with 40,000 Betamyl units/kg of pSac-pMD229 and the firmness of the bread is tested according to the protocol set out in Example 12 at various times after baking. Bread is also baked with 40,000 Betamyl units/kg of pSac-D34/pMD3 (SEQ ID NO: 2). The firmness of the bread is tested. As a control, firmness of bread baked without any enzyme is also measured.

Figure 2:
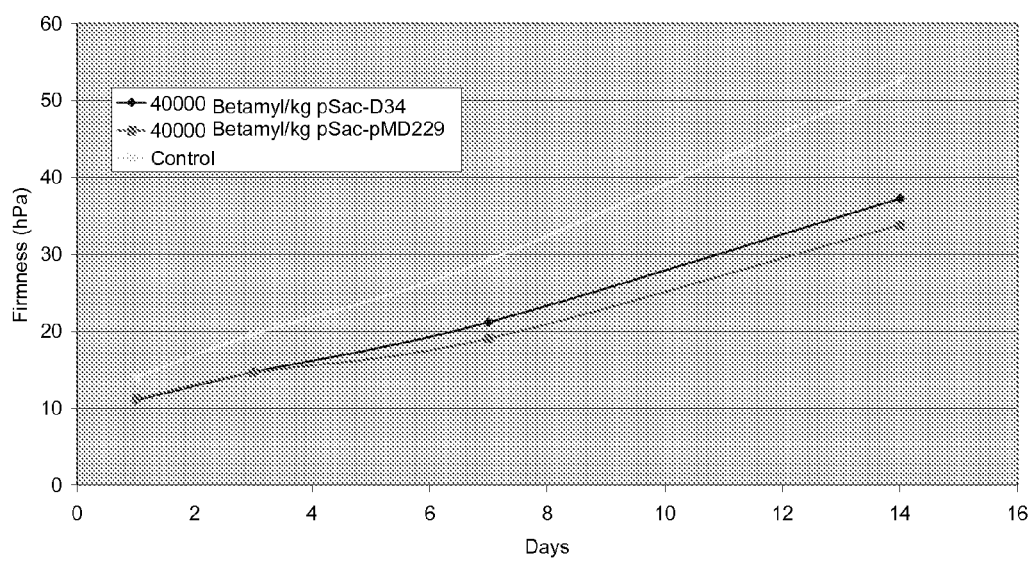
FIG. 2 shows an improved firmness effect, i.e. lower firmness, of bread treated with pSac-pMD229 versus bread treated pSac-D34 during storage time after baking. The figure shows the results of a baking trial in which firmness of bread treated with pSac-pMD229, pSac-D34 and untreated bread are tested. The X-axis shows the number of days, while the Y-axis shows firmness expressed as hPa. Diamond: 40,000 Betamyl units/kg of pSac-D34. Square: 40,000 Betamyl units/kg of pSac-pMD229. Cross: Control (no enzyme).

FIG. 2 shows the results of a baking trial in which firmness of bread treated with pSac-pMD229 is compared to firmness of bread treated with pSac-D34.

Example 18

Improved Handling Properties of Food Products Treated with PS4 Variant Polypeptides: Resilience Bread is baked with 40,000 Betamyl units/kg of pSac-pMD229 and the resilience of the bread is tested according to the protocol set out in Example 13 at various times after baking. Bread is also baked with 40,000 Betamyl units/kg of pSac-D34/pMD3 (SEQ ID NO: 2). The resilience of the bread is tested. As a control, resilience of bread baked without any enzyme is also measured.

Figure 3:
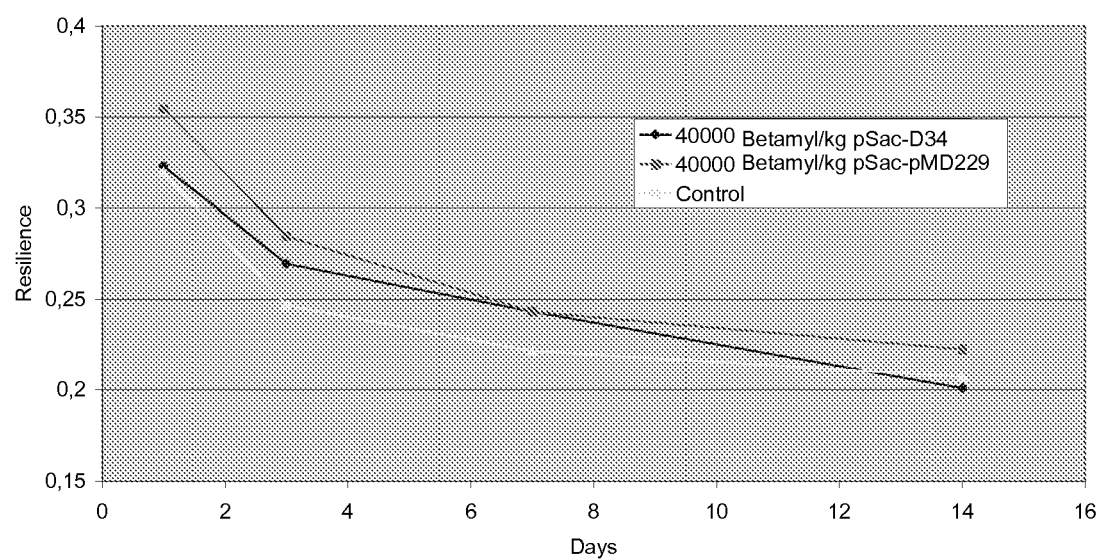
FIG. 3 shows an improved resilience effect, i.e. higher resilience, of bread treated with pSac-pMD229 versus bread treated with pSac-D34 during storage time after baking. The figure shows the results of a baking trial in which resilience of bread treated with pSac-pMD229, pSac-D34 and untreated bread are tested. The X-axis shows the number of days, while the Y-axis shows resilience expressed as Resilience Units. Diamond: 40,000 Betamyl units/kg of pSac-D34. Square: 40,000 Betamyl units/kg of pSac-pMD229. Cross: Control (no enzyme).

FIG. 3 shows the results of a baking trial in which resilience of bread treated with pSac-pMD229 is compared to resilience of bread treated with pSac-D34.

Example 19

Improved Handling Properties of Food Products Treated with PS4 Variant Polypeptides: Cohesiveness Bread is baked with 40,000 Betamyl units/kg of pSac-pMD229 and the cohesiveness of the bread is tested according to the protocol set out in Example 14 at various times after baking. Bread is also baked with 40,000 Betamyl units/kg of pSac-D34/pMD3 (SEQ ID NO: 2). The cohesiveness of the bread is tested. As a control, cohesiveness of bread baked without any enzyme is also measured.

Figure 4:
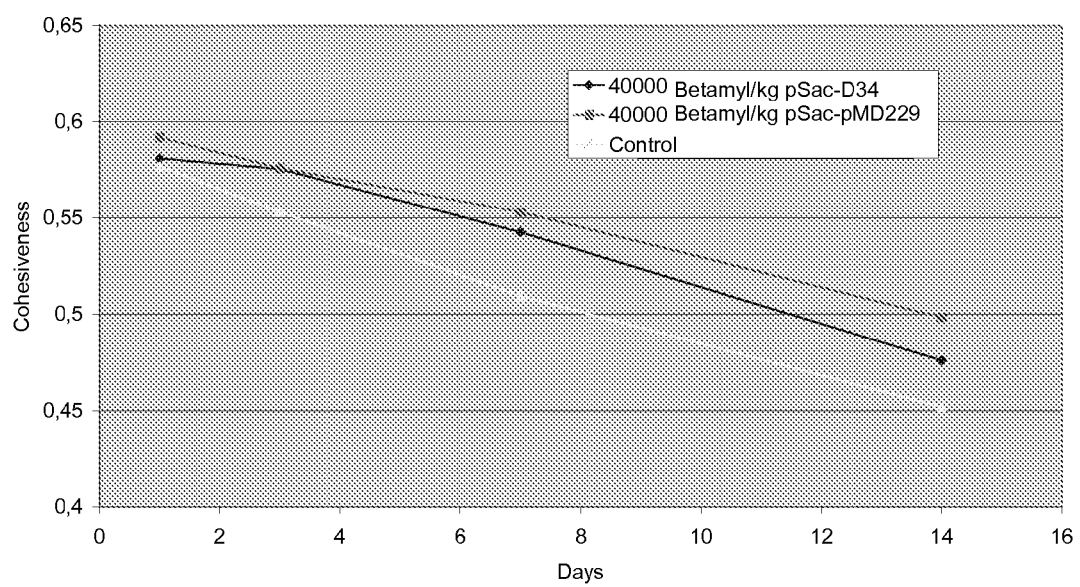
FIG. 4 shows an improved cohesiveness effect, i.e. higher cohesiveness, of bread treated with pSac-pMD229 versus bread treated with pSac-D34 during storage time after baking. The figure shows the results of a baking trial in which cohesiveness of bread treated with pSac-pMD229, pSac-D34 and untreated bread are tested. The X-axis shows the number of days, while the Y-axis shows cohesiveness expressed as Cohesiveness Units. Diamond: 40,000 Betamyl/kg of pSac-D34. Square: 40,000 Betamyl/kg of pSac-pMD229. Cross: Control (no enzyme).

FIG. 4 shows the results of a baking trial in which cohesiveness of bread treated with pSac-pMD229 is compared to cohesiveness of bread treated with pSac-D34.

REFERENCES

Penning a, D., van der Veen, B. A., Knegtel, R. M., van Hijum, S. A., Rozeboom, H. J., Kalk, K. H., Dijkstra, B. W., Dijkhuizen, L. (1996). The raw starch binding domain of cyclodextrin glycosyltransferase from *Bacillus circulans* strain 251. J. Biol. Chem. 271, 32777-32784.

Sambrook J, F.E.M.T. (1989). Molecular Cloning: A Laboratory Manual, 2nd Edn. Cold Spring Harbor Laboratory, Cold Spring Harbor N.Y.

Zhou, J. H., Baba, T., Takano, T., Kobayashi, S., Arai, Y. (1989). Nucleotide sequence of the maltotetraohydrolase gene from *Pseudomonas saccharophila*. FEBS Lett. 255, 37-41.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention is further described by the following numbered paragraphs:

1. A PS4 variant polypeptide derivable from a parent polypeptide having amylase activity selected from the group consisting of:
   (a) a polypeptide comprising an amino acid mutation at each of positions 33, 34, 121, 134, 141, 146, 157, 161, 178, 179, 223, 229, 272, 303, 307, 309 and 334;
   (b) a polypeptide comprising an amino acid mutation at each of positions 33, 34, 121, 134, 141, 145, 146, 157, 178, 179, 223, 229, 272, 303, 307 and 334;
   (c) a polypeptide comprising an amino acid mutation at each of positions 33, 34, 121, 134, 141, 146, 157, 178, 179, 223, 229, 272, 303, 307, 309 and 334;
   (d) a polypeptide comprising an amino acid mutation at each of positions 3, 33, 34, 70, 121, 134, 141, 146, 157, 178, 179, 223, 229, 272, 303, 307, 309 and 334;
with reference to the position numbering of a *Pseudomonas saccharophilia* exoamylase sequence shown as SEQ ID NO: 1.

2. A PS4 variant polypeptide according to Paragraph 1, in which each of the amino acid mutations in polypeptide (a) are independently selected from the group consisting of: 33Y, 34N, 121F, 134R, 141P, 146G, 157L, 161A, 178F, 179T, 223E, 229P, 272Q, 303E, 307L, 309P and 334P, preferably N33Y, D34N, G121F, G134R, A141P, Y146G, I157L, S161A, L178F, A179T, G223E, S229P, H272Q, G303E, H307L, A309P and S334P.

3. A PS4 variant polypeptide according to Paragraph 2, which comprises the sequence pSac-pMD229 (SEQ ID NO: 13).

4. A PS4 variant polypeptide according to Paragraph 1, in which each of the amino acid mutations in polypeptide (b) are independently selected from the group consisting of: 33Y, 34N, 121F, 134R, 141P, 145D, 146G, 157L, 178F, 179T, 223E, 229P, 272Q, 303E, 307L and 334P, preferably N33Y, D34N, G121F, G134R, A141P, N145D, Y146G, I157L, L178F, A179T, G223E, S229P, H272Q, G303E, H307L and S334P.

5. A PS4 variant polypeptide according to Paragraph 4, which comprises the sequence pSac-pMD248 (SEQ ID NO: 15).

6. A PS4 variant polypeptide according to Paragraph 1, in which each of the amino acid mutations in polypeptide (c) are independently selected from the group consisting of: 33Y, 34N, 121D, 134R, 141P, 146G, 157L, 178F, 179T, 223E, 229P, 272Q, 303E, 307L, 309P and 334P, preferably N33Y, D34N, G121D, G134R, A141P, Y146G, I157L, L178F, A179T, G223E, S229P, H272Q, G303E, H307L, A309P and S334P.

7. A PS4 variant polypeptide according to Paragraph 6 which comprises the sequence pSac-pMD253 (SEQ ID NO: 17).

8. A PS4 variant polypeptide according to Paragraph 1, in which each of the amino acid mutations in polypeptide (d) are independently selected from the group consisting of: 3S, 33Y, 34N, 70D, 121D, 134R, 141P, 146G, 157L, 178F, 179T, 223E, 229P, 272Q, 303E, 307L, 309P and 334P, preferably A3S, N33Y, D34N, G70D, G121D, G134R, A141P, Y146G, I157L, L178F, A179T, G223E, S229P, H272Q, G303E, H307L, A309P and S334P.

9. A PS4 variant polypeptide according to Paragraph 8 which comprises the sequence pSac-pMD271 (SEQ ID NO: 19).

10. A PS4 variant polypeptide according to Paragraph 1, in which the parent polypeptide comprises exoamylase activity, preferably a non-maltogenic exoamylase, more preferably a glucan 1,4-alpha-maltotetrahydrolase (EC 3.2.1.60).

11. A PS4 variant polypeptide according to Paragraph 1, in which the parent polypeptide is or is derivable from *Pseudomonas* species, preferably *Pseudomonas saccharophilia* or *Pseudomonas stutzeri*.

12. A PS4 variant polypeptide according to Paragraph 1, in which the parent polypeptide is a non-maltogenic exoamylase from *Pseudomonas saccharophilia* exoamylase having a sequence shown as SEQ ID NO: 1 or SEQ ID NO: 5.

13. A PS4 variant polypeptide according to Paragraph 12 having an amino acid sequence which at least 75% identical to SEQ ID NO: 1 or SEQ ID NO: 5.

14. A PS4 variant polypeptide according to Paragraph 1, in which the parent polypeptide is a non-maltogenic exoamylase from *Pseudomonas stutzeri* having a sequence shown as SEQ ID NO: 7 or SEQ ID NO: 11.

15. A PS4 variant polypeptide according to according to Paragraph 14 having an amino acid sequence which at least 75% identical to SEQ ID NO: 7 or SEQ ID NO: 11.

16. A PS4 variant polypeptide according to Paragraph 1, in which the PS4 variant polypeptide has a higher thermostability compared to the parent polypeptide or a wild type polypeptide when tested under the same conditions.

17. A PS4 variant polypeptide according to Paragraph 16, in which the half life (t½), preferably at 60 degrees C., is increased by 15% or more, preferably 50% or more, most preferably 100% or more, relative to the parent polypeptide or the wild type polypeptide.

18. A PS4 variant polypeptide according to Paragraph 1, in which the PS4 variant polypeptide has a higher exo-specificity compared to the parent polypeptide or a wild type polypeptide when tested under the same conditions.

19. A PS4 variant polypeptide according to Paragraph 18, in which the PS4 variant polypeptide has 10% or more, preferably 20% or more, preferably 50% or more, exo-specificity compared to the parent polypeptide or the wild type polypeptide.

20. A PS4 variant polypeptide according to Paragraph 1, in which a food product treated with a the PS4 variant polypeptide has any one or more, preferably all of the following properties: (a) lower firmness; (b) higher resilience; and (c) higher cohesiveness compared to a food product which has been treated with a parent polypeptide or a wild type polypeptide.

21. A PS4 variant polypeptide according to Paragraph 20, in which the resilience or cohesiveness of the food product is independently increased by 15% or more, preferably 50% or more, most preferably 100% or more, relative to a food product which has been treated with a parent polypeptide or a wild type polypeptide.

22. A PS4 variant polypeptide according to Paragraph 21, in which each of resilience and cohesiveness of a food product treated with a the PS4 variant polypeptide is increased compared to a food product which has been treated with a parent polypeptide or a wild type polypeptide.

23. A PS4 variant polypeptide according to Paragraph 20, in which the firmness of the food product is independently decreased by 15% or more, preferably 50% or more, most preferably 100% or more, relative to a food product which has been treated with a parent polypeptide or a wild type polypeptide.

24. A PS4 variant polypeptide according to Paragraph 23, in which the firmness of a food product treated with a the PS4 variant polypeptide is increased compared to a food product which has been treated with a parent polypeptide or a wild type polypeptide.

25. A polypeptide derivable from a PS4 variant polypeptide according to Paragraph 1 by mutation at one or more residues of the PS4 variant polypeptide sequence, in which the polypeptide has a higher thermostability or a higher exo-specificity, or both, compared to the parent polypeptide of the PS4 variant polypeptide or a wild type polypeptide, or in which a food product treated with a the PS4 variant polypeptide has any one or more, preferably all of the following properties: (a) lower firmness; (b) higher resilience; or (c) higher cohesiveness as compared to a food product which has been treated with a parent polypeptide or a wild type polypeptide.

26. A polypeptide comprising a fragment of at least 20 residues of a PS4 variant polypeptide according to Paragraph 1, in which the polypeptide has non-maltogenic exoamylase activity.

27. A polypeptide derivable from a polypeptide according to Paragraph 1 by mutation at one or more residues of the PS4 variant polypeptide sequence, in which the polypeptide has a higher thermostability or a higher exo-specificity, or both, compared to the parent polypeptide of the PS4 variant polypeptide or a wild type polypeptide.

28. A method of producing a food or feed additive comprising admixing a polypeptide as set out in Paragraph 1 with one or more components.

29. A process for treating a starch comprising contacting the starch with a polypeptide as set out in Paragraph 1 and allowing the polypeptide to generate from the starch one or more linear products.

30. A method of producing a food or feed product comprising admixing a polypeptide as set out in Paragraph 1 with a food or feed.

31. A process of preparing a food or feed product comprising admixing a polypeptide as set out in Paragraph 1 with a food or feed ingredient.

32. A method according to Paragraph 30, or a process according to Paragraph 31, in which the food product comprises a dough or a dough product, preferably a processed dough product.

33. A use or process according to any of Paragraphs 28 to 31, in which the food product is a bakery product.

34. A process for making a bakery product comprising: (a) providing a starch medium; (b) adding to the starch medium a polypeptide as set out in Paragraph 1; and (c) applying heat to the starch medium during or after step (b) to produce a bakery product.

35. A food product, feed product, dough product or a bakery product obtained or obtainable by a process according to any of Paragraphs 28 to 31.

36. An improver composition for a dough, in which the improver composition comprises a polypeptide as set out in Paragraph 1, and at least one further dough ingredient or dough additive.

37. A composition comprising a flour and a polypeptide as set out in Paragraph 1.

38. A method of retarding or reducing staling, preferably detrimental retrogradation, of a dough product, the method comprising admixing a polypeptide as set out in Paragraph 1 with a dough product.

39. A method of improving any one or more of firmness, resilience or cohesiveness of a dough product, the method comprising admixing a polypeptide as set out in Paragraph 1 with a dough product.

40. A combination of a PS4 variant polypeptide as set out in Paragraph 1, together with Novamyl, or a variant, homologue, or mutants thereof which has maltogenic alpha-amylase activity.

41. A process for treating a food product comprising admixing a combination according to Paragraph 40 with a food product.

42. A food or feed product produced by treatment with a combination according to Paragraph 40.

43. A nucleic acid which encodes a polypeptide according to Paragraph 1.

44. A nucleic acid according to Paragraph 43 having a nucleic acid sequence which at least 75% identical to SEQ ID NO: 6 or SEQ ID NO: 12.

45. A nucleic acid comprising a fragment of at least 60 residues of a nucleic acid according to Paragraph 44 which is capable of encoding a polypeptide having non-maltogenic exoamylase activity.

46. A nucleic acid sequence derivable from a parent sequence, the parent sequence capable of encoding an amylase, which nucleic acid sequence comprises a substitution at one or more residues such that the nucleic acid encodes one or more of the following mutations at the positions specified: (a) 33Y, 34N, 121F, 134R, 141P, 146G, 157L, 161A, 178F, 179T, 223E, 229P, 272Q, 303E, 307L, 309P and 334P; (b) 33Y, 34N, 121F, 134R, 141P, 145D, 146G, 157L, 178F, 179T, 223E, 229P, 272Q, 303E, 307L and 334P (c) 33Y, 34N, 121D, 134R, 141P, 146G, 157L, 178F, 179T, 223E, 229P, 272Q, 303E, 307L, 309P and 334P; (d) 3S, 33Y, 34N, 70D, 121D, 134R, 141P, 146G, 157L, 178F, 179T, 223E, 229P, 272Q, 303E, 307L, 309P and 334P; with reference to the position numbering of a *Pseudomonas saccharophilia* exoamylase sequence shown as SEQ ID NO: 1.

47. A nucleic acid sequence according to Paragraph 43, which is derived from a parent sequence encoding a non-maltogenic exoamylase by substitution of one or more nucleotide residues.

48. A nucleic acid sequence according Paragraph 43, selected from the group consisting of: pSac-pMD229 (SEQ ID NO: 14), pSac-pMD248 (SEQ ID NO: 16), pSac-pMD253 (SEQ ID NO: 18) and pSac-pMD271 (SEQ ID NO: 20).

49. A plasmid comprising a PS4 nucleic acid according to Paragraph 43.

50. An expression vector comprising a PS4 nucleic acid according to Paragraph 43, or capable of expressing a polypeptide according to Paragraph 1.

51. A host cell comprising, preferably transformed with, a plasmid according to Paragraph 49 or an expression vector according to Paragraph 50.

52. A cell capable of expressing a polypeptide according to Paragraph 1.

53. A host cell according to Paragraph 51, or a cell according to Paragraph 52, which is a bacterial, fungal or yeast cell.

54. A method of expressing a PS4 variant polypeptide, the method comprising obtaining a host cell or a cell according to Paragraph 51 or 52 and expressing the polypeptide from the cell or host cell, and optionally purifying the polypeptide.

55. A method of altering the sequence of a polypeptide by introducing an amino acid substitution selected from the group consisting of: (a) 33Y, 34N, 121F, 134R, 141P, 146G, 157L, 161A, 178F, 179T, 223E, 229P, 272Q, 303E, 307L, 309P and 334P; (b) 33Y, 34N, 121F, 134R, 141P, 145D, 146G, 157L, 178F, 179T, 223E, 229P, 272Q, 303E, 307L and 334P (c) 33Y, 34N, 121D, 134R, 141P, 146G, 157L, 178F, 179T, 223E, 229P, 272Q, 303E, 307L, 309P and 334P; (d) 3S, 33Y, 34N, 70D, 121D, 134R, 141P, 146G, 157L, 178F, 179T, 223E, 229P, 272Q, 303E, 307L, 309P and 334P (with reference to the position numbering of a *Pseudomonas saccharophilia* exoamylase sequence shown as SEQ ID NO: 1), into a parent polypeptide having amylase activity.

56. A method of altering the sequence of a non-maltogenic exoamylase by introducing a substitution selected from the group consisting of: (a) 33Y, 34N, 121F, 134R, 141P, 146G, 157L, 161A, 178F, 179T, 223E, 229P, 272Q, 303E, 307L, 309P and 334P; (b) 33Y, 34N, 121F, 134R, 141P, 145D, 146G, 157L, 178F, 179T, 223E, 229P, 272Q, 303E, 307L and 334P (c) 33Y, 34N, 121D, 134R, 141P, 146G, 157L, 178F, 179T, 223E, 229P, 272Q, 303E, 307L, 309P and 334P; (d) 3S, 33Y, 34N, 70D, 121D, 134R, 141P, 146G, 157L, 178F, 179T, 223E, 229P, 272Q, 303E, 307L, 309P and 334P with reference to the position numbering of a *Pseudomonas saccharophilia* exoamylase sequence shown as SEQ ID NO: 1.

57. A method according to Paragraph 55, in which the sequence of the non-maltogenic exoamylase is altered by altering the sequence of a nucleic acid which encodes the non-maltogenic exoamylase.

58. A method of producing a PS4 polypeptide variant, the method comprising introducing an amino acid substitution into a parent polypeptide having amylase activity, the amino acid substitution being selected from the group consisting of: (a) 33Y, 34N, 121F, 134R, 141P, 146G, 157L, 161A, 178F, 179T, 223E, 229P, 272Q, 303E, 307L, 309P and 334P; (b) 33Y, 34N, 121F, 134R, 141P, 145D, 146G, 157L, 178F, 179T, 223E, 229P, 272Q, 303E, 307L and 334P (c) 33Y, 34N, 121D, 134R, 141P, 146G, 157L, 178F, 179T, 223E, 229P, 272Q, 303E, 307L, 309P and 334P; (d) 3S, 33Y, 34N, 70D, 121D, 134R, 141P, 146G, 157L, 178F, 179T, 223E, 229P, 272Q, 303E, 307L, 309P and 334P with reference to the position numbering of a *Pseudomonas saccharophilia* exoamylase sequence shown as SEQ ID NO: 1.

59. A method according to Paragraph 55, in which the sequence of a nucleic acid encoding the parent polypeptide is altered to introduce the amino acid substitution.

60. A method of altering the sequence of a nucleic acid encoding a non-maltogenic exoamylase, the method comprising introducing into the sequence a codon which encodes an amino acid residue selected from the group consisting of: (a) 33Y, 34N, 121F, 134R, 141P, 146G, 157L, 161A, 178F, 179T, 223E, 229P, 272Q, 303E, 307L, 309P and 334P; (b) 33Y, 34N, 121F, 134R, 141P, 145D, 146G, 157L, 178F, 179T, 223E, 229P, 272Q, 303E, 307L and 334P (c) 33Y, 34N, 121D, 134R, 141P, 146G, 157L, 178F, 179T, 223E, 229P, 272Q, 303E, 307L, 309P and 334P; (d) 3S, 33Y, 34N, 70D, 121D, 134R, 141P, 146G, 157L, 178F, 179T, 223E, 229P, 272Q, 303E, 307L, 309P and 334P, with reference to the position numbering of a *Pseudomonas saccharophilia* exoamylase sequence shown as SEQ ID NO: 1.

61. A method of increasing the thermostability, or the exo-specificity, or both, of a polypeptide, the method comprising the steps as set out in Paragraph 55.

62. A method according to Paragraph 55, in which the polypeptide is isolated or purified, or both.

63. A polypeptide obtainable by a method according to Paragraph 55.

64. A polypeptide obtained by a method according to Paragraph 55.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

SEQUENCE LISTINGS

```
SEQ ID NO: 1
PS4 reference sequence, derived from Pseudomonas saccharophila
maltotetrahydrolase amino acid sequence.
  1 DQAGKSPAGV RYHGGDEIIL QGFHWNVVRE AP NDWYNILR QQASTIAADG FSAIWMPVPW
 61 RDFSSWTDGG KSGGGEGYFW HDFNKNGRYG SDAQLRQAAG ALGGAGVKVL YDVVPNHMNR
121 GYPDKEINLP AGQGFWRNDC ADPGNYPNDC DDGDRFIGGE SDLNTGHPQI YGMFRDELAN
181 LRSGYGAGGF RFDFVRGYAP ERVDSWMSDS ADSSFCVGEL WKGPSEYPSW DWRNTASWQQ
241 IIKDWSDRAK CPVFDFALKE RMQNGSVADW KHGLNGNPDP RWREVAVTFV DNHDTGYSPG
301 QNGGQHHWAL QDGLIRQAYA YILTSPGTPV VYWSHMYDWG YGDFIRQLIQ VRRTAGVRAD
361 SAISFHSGYS GLVATVSGSQ QTLVVALNSD LANPGQVASG SFSEAVNASN GQVRVWRSGS
421 GDGGGNDGGE GGLVNVNFRC DNGVTQMGDS VYAVGNVSQL GNWSPASAVR LTDTSSYPTW
481 KGSIALPDGQ NVEWKCLIRN EADATLVRQW QSGGNNQVQA AAGASTSGSF SEQ ID NO:2
pSac-D34 sequence; Pseudomonas saccharophila maltotetrahydrolase
amino acid sequence with 11 substitutions and deletion of the starch
binding domain. pSac-D34 (also known as pMD3) comprises mutations
N33Y, D34N, G121D, G134R, A141P, I157L, L178F, A179T, G223A, H307L,
S334P relative to wild type non-maltogenic exoamylase.
  1 DQAGKSPAGV RYHGGDEIIL QGFHWNVVRE AP YNWYNILR QQASTIAADG FSAIWMPVPW
 61 RDFSSWTDPG KSGGGEGYFW HDFNKNGRYG SDAQLRQAAG ALGGAGVKVL YDVVPNHMNR
121 DYPDKEINLP AGQRFWRNDC PDPGNYPNDC DDGDRFLGGE SDLNTGHPQI YGMFRDEFTN
181 LRSGYGAGGF RFDFVRGYAP ERVDSWMSDS ADSSFCVGEL WKAPSEYPSW DWRNTASWQQ
241 IIKDWSDRAK CPVFDFALKE RMQNGSVADW KHGLNGNPDP RWREVAVTFV DNHDTGYSPG
301 QNGGQHLWAL QDGLIRQAYA YILTSPGTPV VYWPHMYDWG YGDFIRQLIQ VRRTAGVRAD
361 SAISFHSGYS GLVATVSGSQ QTLVVALNSD LANPGQVASG SFSEAVNASN GQVRVWRSGS
421 GDGGGNDGG SEQ ID NO:3
pSac-D20 sequence; Pseudomonas saccharophila maltotetrahydrolase
amino acid sequence with 13 substitutions and deletion of the
starch binding domain.
  1 DQAGKSPAGV RYHGGDEIIL QGFHWNVVRE AP YNWYNILR QQASTIAADG FSAIWMPVPW
 61 RDFSSWTDPG RSGGGEGYFW HDFNKNGRYG SDAQLRQAAG ALGGAGVKVL YDVVPNHMNR
121 DYPDKEINLP AGQRFWRNDC PDPGNYPNDC DDGDRFLGGE SDLNTGHPQI YGMFRDEFTN
```

-continued

```
181 LRSGYGAGGF RFDFVRGYAP ERVDSWMSDS ADSSFCVGEL WKAPSEYPSW DWRNTASWQQ
241 IIKDWSDRAK CPVFDFALKE RMQNGSVADW KHGLNGNPDP RWREVAVTFV DNHDTGYSPG
301 QNGGQHLWAL QDGLIRQAYA YILTSPGTPV VYWPHMYDWG YGEFIRQLIQ VRRTAGVRAD
361 SAISFHSGYS GLVATVSGSQ QTLVVALNSD LANPGQVASG SFSEAVNASN GQVRVWRSGS
421 GDGGGNDGG
```

SEQ ID NO:4
pSac-D14 sequence; Pseudomonas saccharophila maltotetrahydrolase
amino acid sequence with 14 substitutions and deletion of the
starch binding domain.

```
  1 DQAGKSPAGV RYHGGDEIIL QGFHWNVVRE APYNWYNILR QQASTIAADG FSAIWMPVPW
 61 RDFSSWTDPG RSGGGEGYFW HDFNKNSRYG SDAQLRQAAG ALGGAGVKVL YDVVPNHMNR
121 DYPDKEINLP AGQRFWRNDC PDPGNYPNDC DDGDRFLGGE SDLNTGHPQI YGMFRDEFTN
181 LRSGYGAGGF RFDFVRGYAP ERVDSWMSDS ADSSFCVGEL WKAPSEYPSW DWRNTASWQQ
241 IIKDWSDRAK CPVFDFALKE RMQNGSVADW KHGLNGNPDP RWREVAVTFV DNHDTGYSPG
301 QNGGQHLWAL QDGLIRQAYA YILTSPGTPV VYWPHMYDWG YGEFIRQLIQ VRRTAGVRAD
361 SAISFHSGYS GLVATVSGSQ QTLVVALNSD LANPGQVASG SFSEAVNASN GQVRVWRSGS
421 GDGGGNDGG
```

SEQ ID NO: 5
Pseudomonas saccharophila Glucan 1,4-alpha-maltotetrahydrolase
precursor (EC 3.2.1.60) (G4-amylase) (Maltotetraose-forming amylase)
(Exo-maltotetraohydrolase) (Maltotetraose-forming exo-amylase).
SWISS-PROT accession number P22963.

```
MSHILRAAVL AAVLLPFPAL ADQAGKSPAG VRYHGGDEII LQGFHWNVVR EAPNDWYNIL
RQQASTIAAD GFSAIWMPVP WRDFSSWTDG KSGGGEGYF WHDFNKNGRY GSDAQLRQAA
GALGGAGVKV LYDVVPNHMN RGYPDKEINL PAGQGFWRND CADPGNYPND CDDGDRFIGG
ESDLNTGHPQ IYGMFRDELA NLRSGYGAGG FRFDFVRGYA PERVDSWMSD SADSSFCVGE
LWKGPSEYPS WDWRNTASWQ QIIKDWSDRA KCPVFDFALK ERMQNGSVAD WKHGLNGNPD
PRWREVAVTF VDNHDTGYSP GQNGGQHHWA LQDGLIRQAY AYILTSPGTP VVYWSHMYDW
GYGDFIRQLI QVRRTAGVRA DSAISFHSGY SGLVATVSGS QQTLVVALNS DLANPGQVAS
GSFSEAVNAS NGQVRVWRSG SGDGGGNDGG EGGLVNVNFR CDNGVTQMGD SVYAVGNVSQ
LGNWSPASAV RLTDTSSYPT WKGSIALPDG QNVEWKCLIR NEADATLVRQ WQSGGNNQVQ
AAAGASTSGS F
```

SEQ ID NO: 6
P. saccharophila mta gene encoding maltotetrahydrolase (EC
number = 3.2.1.60). GenBank accession number X16732.

```
gatcggcgta ggtttcgcat tcgttgccca ggcgatattc cgccggtgcc ccagcagcct
ggaagcaggc ctggtcgccg ccgccggccg tggcgccgac gcccgaacgc agatagccgt
ggaaatcgac cgccagggcc gggccggcga ccagcagggc ggcaagcagg caggcgggtt
ttaggacgaa caggggggtgc gcggtgtgct tcatgacgag gtccttgttt ttcttgttaa
tgccgaatcg atcacgcctt cgctgcgtgt cgcagggcgc agtcggtgg cgaaagcctc
ggggatggct ccgctggcgg catcctcccg accagagatt cgctggcgc agctcgaggg
cgtaatcagg atgagtgcgg cgtaatccct gggtgggc tacgcccggc agggcgcaga
tgattgccag gggccttcgg cctggccact acgccgcctg caactgggcg ggggaggttg
gtggtcgggg cgtgcagggg cagcctgcgg gtgccggtcg aagacccggc cggcgttcat
cctcgtccgg cggccttgcc gtaggatacc cgaacaagca caagaaccgg agtattgcga
tgagccacat cctgcgtgcc gccgtattgg cggcggtcct gctgccgttt ccgcactgg
ccgatcaggc cggcaagagc ccggccgggg tgcgctacca cggcggcgac gaaatcatcc
tccaggcctt ccactggaac gtcgtccgcg aagcgcccaa cgactggtac aacatcctcc
gccaacaggc ctcgacgatc gcggccgacg gcttctcggc aatctggatg ccggtgccct
ggcgtgactt ctccagctgg accgacgggc gcaagtccgg cggcggcgaa ggctacttct
ggcacgactt caacaagaac ggccgctacg gcagcgacgc ccagctgcgc caggccgccg
gcgcactcgg tggcgccggg gtgaaggtgc tctacgatgt ggtgcccaat cacatgaacc
gctactaccc ggacaaggag atcaacctgc cggccggcca gggcttctgg cgcaacgact
gcgccgaccc gggcaactac cccaacgact gcgacgacgg tgaccgcttc atcggcggcg
agtcggacct gaacaccggc catccgcaga tttacggcat gttcgcgac gagcttgcca
acctgcgcag cggctacggc gccggcggct tccgcttcga cttcgttcgc ggctatgcgc
ccgagcgggt cgacagctgg atgagcgaca gcgccgacag cagcttctgc gttggcgagc
tgtggaaagg cccttctgaa tatccgagct gggactggcg caacacgcg agctggcagc
agatcatcaa ggactggtcc gacgggccaa gtgccgt gttcgacttc gctctcaagg
agcgcatgca gaacggctcg gtcgccgact ggaagcatgg cctcaatggc aaccccgacc
cgcgctggcg cgaggtggcg gtgaccttcg tcgacaacca cgacaccggc tattcgccag
ggcagaacgg cggccagcac cactgggcg tgcaggacgg gctgatccgc caggcctacg
cctacatcct caccagcccg ggcacgccgg tggtgtactg gtcgcacatg tacgactggg
gctacggcga cttcatccgc cagctgatcc aggtgcggcg caccgccggc gtgcgcgcc
attcggcgat cagcttccat agcggctaca gcggtctgt cgctaccgtc agcggcagcc
agcagaccct ggtggtggcg ctcaactccg atctggccaa ccccggccag gttgccagcg
gcagcttcag cgaggtggtc aacgccagca acggccaggt gcgcgtctgg cgcagcggta
gcggcgatgg cggcggaat gacggcggcg agggtggctt ggtcaatgtg aactttcgct
gcgacaacgg cgtgacgcag atgggcgaca gcgtctacgc ggtgggcaac gtcagccagc
tcggcaactg gagcccggcc tccgcggtac ggctgaccga caccagcagc tatccgacct
ggaagggcag catcgccctg cctgacggtc agaacgtgga atggaagtgc ctgatccgca
acgaggcgga cgcgacgctg gtgcgtcagt ggcaatcggg cggcaacaac caggtccagg
ccgccggcgg ctccgagcac agcacctctg tctgacgacg ccccg gcctcggcta
cgcctacgcc gggcggctcc tcccgaccca ggctgggcag ggaggaggcc ggcgactggc
cgggccgccg atgctggcac gacaaccata aagccttcg cgctgcgctg tcgtatcagg
agctgttcat gttgggccag accgctcga ccccttccg gcttggcttc ctggccggc
tgtacctgct gatcgccgca ctggtggcct tgctgatgct ggtagccggc accagcctgg
ttgccatcgg ccgcctgcaa ggcaatgccg agcaaatctc gtcgaccgcg tcgcgtctgc
```

```
tggtcagcga gagcttcttc ggtacgttgc agagcctgac gcagaacctg tccgacgccc
tggccgagga ccggcctgac cagctcgacg gctatgtcgg ccggcatcgc acgctgcagg
accaggccct cgagctgttc gcccagctgg agcgggtgac gccggcacat gccgagacca
agcaagcctg gcgcgctgt tgccggagct cgaccgccgc agcctggcgc tgatcgatgc
gcacgcgacc tgctcgcgcg tggggcgcaa cgccgtcgcc tgcgcgatct gcagctgcag
ttctcgcggc tcaagcagga cctgctgcag gcgcagttcg tgacgggcga ggcagctggtc
gcctattcca tcaagcagtt catcatcccg ctcgagcagg tcgagcgctg ctgttcgatg
ccatcggcgt gtcttcgatc aaggcactcg atgaagcggg tgcgcagatc SEQ ID NO:7
PS4 reference sequence, derived from Pseudomonas stutzeri malto-
tetrahydrolase amino acid sequence.
  1 DQAGKSPNAV RYHGGDEIIL QGFHWNVVRE APNDWYNILR QQAATIAADG FSAIWMPVPW
 61 RDFSSWSDGS KSGGGEGEYFW HDFNKNGRYG SDAQLRQAAS ALGGAGVKVL YDVVPNHMNR
121 GYPDKEINLP AGQGFWRNDC ADPGNYPNDC DDGDRFIGGD ADLNTGHPQV YGMFRDEFTN
181 LRSQYGAGGF RFDFVRGYAP ERVNSWMTDS ADNSFCVGEL WKGPSEYPNW DWRNTASWQQ
241 IIKDWSDRAK CPVFDFALKE RMQNGSIADW KHGLNGNPDP RWREVAVTFV DNHDTGYSPG
301 QNGGQHHWAL QDGLIRQAYA YILTSPGTPV VYWSHMYDWG YGDFIRQLIQ VRRAAGVRAD
361 SAISFHSGYS GLVATVSGSQ QTLVVALNSD LGNPGQVASG SFSEAVNASN GQVRVWRSGT
421 GSGGGEPGAL VSVSFRCDNG ATQMGDSVYA VGNVSQLGNW SPAAALRLTD TSGYPTWKGS
481 IALPAGQNEE WKCLIRNEAN ATQVRQWQGG ANNSLTPSEG ATTVGRL SEQ ID NO: 8
PStu-D34 sequence; Pseudomonas stutzeri maltotetrahydrolase amino
acid sequence with 9 substitutions.
  1 DQAGKSPNAV RYHGGDEIIL QGFHWNVVRE APYNWYNILR QQAATIAADG FSAIWMPVPW
 61 RDFSSWSDPS KSGGGEGEYFW HDFNKNGRYG SDAQLRQAAS ALGGAGVKVL YDVVPNHMNR
121 DYPDKEINLP AGQRFWRNDC PDPGNYPNDC DDGDRFLGGD ADLNTGHPQV YGMFRDEFTN
181 LRSQYGAGGF RFDFVRGYAP ERVNSWMTDS ADNSFCVGEL WKAPSEYPNW DWRNTASWQQ
241 IIKDWSDRAK CPVFDFALKE RMQNGSIADW KHGLNGNPDP RWREVAVTFV DNHDTGYSPG
301 QNGGQHLWAL QDGLIRQAYA YILTSPGTPV VYWPHMYDWG YGDFIRQLIQ VRRAAGVRAD
361 SAISFHSGYS GLVATVSGSQ QTLVVALNSD LGNPGQVASG SFSEAVNASN GQVRVWRSGT
421 GSGGGEPGAL VSVSFRCDNG ATQMGDSVYA VGNVSQLGNW SPAAALRLTD TSGYPTWKGS
481 IALPAGQNEE WKCLIRNEAN ATQVRQWQGG ANNSLTPSEG ATTVGRL SEQ ID NO: 9
PStu-D20 sequence; Pseudomonas stutzeri maltotetrahydrolase amino
acid sequence with 11 substitutions.
  1 DQAGKSPNAV RYHGGDEIIL QGFHWNVVRE APYNWYNILR QQAATIAADG FSAIWMPVPW
 61 RDFSSWSDPS RSGGGEGEYFW HDFNKNGRYG SDAQLRQAAS ALGGAGVKVL YDVVPNHMNR
121 DYPDKEINLP AGQRFWRNDC PDPGNYPNDC DDGDRFLGGD ADLNTGHPQV YGMFRDEFTN
181 LRSQYGAGGF RFDFVRGYAP ERVNSWMTDS ADNSFCVGEL WKAPSEYPNW DWRNTASWQQ
241 IIKDWSDRAK CPVFDFALKE RMQNGSIADW KHGLNGNPDP RWREVAVTFV DNHDTGYSPG
301 QNGGQHLWAL QDGLIRQAYA YILTSPGTPV VYWPHMYDWG YGEFIRQLIQ VRRAAGVRAD
361 SAISFHSGYS GLVATVSGSQ QTLVVALNSD LGNPGQVASG SFSEAVNASN GQVRVWRSGT
421 GSGGGEPGAL VSVSFRCDNG ATQMGDSVYA VGNVSQLGNW SPAAALRLTD TSGYPTWKGS
481 IALPAGQNEE WKCLIRNEAN ATQVRQWQGG ANNSLTPSEG ATTVGRL SEQ ID NO: 10
PStu-D14 sequence; Pseudomonas stutzeri maltotetrahydrolase amino
acid sequence with 12 substitutions.
  1 DQAGKSPNAV RYHGGDEIIL QGFHWNVVRE APYNWYNILR QQAATIAADG FSAIWMPVPW
 61 RDFSSWSDPS RSGGGEGEYFW HDFNKNSRYG SDAQLRQAAS ALGGAGVKVL YDVVPNHMNR
121 DYPDKEINLP AGQRFWRNDC PDPGNYPNDC DDGDRFLGGD ADLNTGHPQV YGMFRDEFTN
181 LRSQYGAGGF RFDFVRGYAP ERVNSWMTDS ADNSFCVGEL WKAPSEYPNW DWRNTASWQQ
241 IIKDWSDRAK CPVFDFALKE RMQNGSIADW KHGLNGNPDP RWREVAVTFV DNHDTGYSPG
301 QNGGQHLWAL QDGLIRQAYA YILTSPGTPV VYWPHMYDWG YGEFIRQLIQ VRRAAGVRAD
361 SAISFHSGYS GLVATVSGSQ QTLVVALNSD LGNPGQVASG SFSEAVNASN GQVRVWRSGT
421 GSGGGEPGAL VSVSFRCDNG ATQMGDSVYA VGNVSQLGNW SPAAALRLTD TSGYPTWKGS
481 IALPAGQNEE WKCLIRNEAN ATQVRQWQGG ANNSLTPSEG ATTVGRL SEQ ID NO: 11
Pseudomonas stutzeri (Pseudomonas perfectomarina). Glucan 1,4-alpha-
maltotetrahydrolase precursor (EC 3.2.1.60) (G4-amylase) (Malto-
tetraose-forming amylase) (Exo-maltotetraohydrolase)(Maltotetraose-
forming exo-amylase). SWISS-PROT accession number P13507.
MSHILRAAVL AAMLLPLPSM ADQAGKSPNA VRYHGGDEII LQGFHWNVVR EAPNDWYNIL
RQQAATIAAD GFSAIWMPVP WRDFSSWSDG SKSGGGEGYF WHDFNKNGRY GSDAQLRQAA
SALGGAGVKV LYDVVPNHMN RGYPDKEINL PAGQGFWRND CADPGNYPND CDDGDRFIGG
DADLNTGHPQ VYGMFRDEFT NLRSQYGAGG FRFDFVRGYA PERVNSWMTD SADNSFCVGE
LWKGPSEYPN WDWRNTASWQ QIIKDWSDRA KCPVFDFALK ERMQNGSIAD WKHGLNGNPD
PRWREVAVTF VDNHDTGYSP GQNGGQHHWA LQDGLIRQAY AYILTSPGTP VVYWSHMYDW
GYGDFIRQLI QVRRAAGVRA DSAISFHSGY SGLVATVSGS QQTLVVALNS DLGNPGQVAS
GSFSEAVNAS NGQVRVWRSG TGSGGGEPGA LVSVSFRCDN GATQMGDSVY AVGNVSQLGN
WSPAAALRLT DTSGYPTWKG SIALPAGQNE EWKCLIRNEA NATQVRQWQG GANNSLTPSE
GATTVGRL SEQ ID NO: 12
P. stutzeri maltotetraose-forming amylase (amyP) gene, complete
cds. GenBank accession number M24516.
  1 gatcggcctt tacggaaagt gatagagctt ctcttccggc aaactttgtt ccccagtgac
```

```
  61 agagggttag tatcggatcg cttcctcttt gggtttggta gatcaggagc gccgagagca
 121 ggatgaaatc ctgcgccag aaggtcgcgc cgaagatgtg gaactgctgc tggccgagat
 181 ccggccggcg ttcatcctcg tccggcggcc ttgccgccag ctacccgaac aagcacaaga
 241 accggagtat tgcgatgagc cacatcctgc gagccgccgt attggcggcg atgctgttgc
 301 cgttgccgtc catggccgat caggccggca agagcccgca cgctgtgcgc taccacggcg
 361 gcgacgaaat cattctccag ggctttcact ggaacgtcgt ccgcgaagcg cccaacgact
 421 ggtacaacat cctgcgccag caggccgcga ccatcgccgc cgacggcttc tcggcgatct
 481 ggatgccggt gccctggcgc gacttctcca gctggagcga cggcagcaag tccggcggcg
 541 gtgaaggcta cttctggcac gacttcaaca agaacggccg ctatggcagt gacgcccagc
 601 tgcgtcaggc cgccagcgcg ctcggtgggc ccggcgtgaa agtgcttttac gacgtggtgc
 661 ccaaccacat gaaccgtggc tatccggaca aggagatcaa cctcccggcc ggccagggct
 721 tctggcgcaa cgactgcgcc gacccggca actaccccaa tgattgcgac gacggcgacc
 781 gcttcatcgg cggcgatgcg gacctcaaca ccggccaccc gcaggtctac ggcatgttcc
 841 gcgatgaatt caccaacctg cgcagtcagt acggtgccgg cggcttccgc ttcgactttg
 901 ttcggggcta tgcgccggag cgggtcaaca gctggatgac cgatagcgcc gacaacagct
 961 tctgcgtcgg cgaactgtgg aaaggcccct ctgagtaccc gaactgggac tggcgcaaca
1021 ccgccagctg gcagcagatc atcaaggact ggtccgaccg ggccaagtgc ccggtgttcg
1081 acttcgccct caaggaacgc atgcagaacg ctcgatcgcc gactggaagc acgcctgaac
1141 ggcaatcccg accgcgtgg cgcgaggtgg cggtgacctt cgtcgacaac cacgacaccg
1201 gctactcgcc cgggcagaac ggtgggcagc accactgggc tctgcaggac gggctgatcc
1261 gccaggccta cgcctacatc ctcaccagcc ccggtacgcc ggtggtgtac tggtcgcaca
1321 tgtacgactg gggttacggc gacttcatcc gtcagctgat ccaggtgcgt cgccgccgca
1381 gcgtgcgcgc cgattcggcg atcagcttcc acagcggcta cagcggtctg gtcgccaccg
1441 tcagcggcag ccagcagacc ctggtggtgg cgctcaactc cgacctgggc aatcccggcc
1501 aggtggccag cggcagcttc agcgaggcgg tcaacgccag caacgccagt gcgcgtgtgt
1561 ggcgtagcg cacgggcagc ggtggcggtg aacccggcgc tctggtcagt gtgagtttcc
1621 gctgcgacaa cggcgcgacg cagatggcg acagcgtcta cgcggtcgc aacgtcagcc
1681 agctcggtaa ctggagcccg gccgcggcgt tgcgcctgac cgacaccagc ggctacccga
1741 cctggaaggg cagcattgcc ttgcctgccg gccagaacga ggaatggaaa tgcctgatcc
1801 gcaacgaggc caacgccacc caggtgcggc aatggcaggg cggggcaaac aacagcctga
1861 cgccgagcga gggcgccacc accgtcggcc ggctctagcc cgggcggcaa ctcgcgcgtc
1921 tcgcggatgt gaggcggctg gtctcggcgg cggtatcgtt gcgctggggg cggggccgcc
1981 gttcacgcgc cctgctatcg ctagtttcg gcgctccgcg catcggccag ttgccagcga
2041 atcgcctgcg cttcggcctg gtgcaggtcg tcgagcagcg ct
```

SEQ ID NO: 13
pSac-pMD229 sequence; *Pseudomonas saccharophila* maltotetrahydrolase
amino acid sequence with 17 substitutions and deletion of the starch
binding domain. pSac-pMD229 comprises mutations N33Y, D34N, G121F,
G134R, A141P, Y146G, I157L, S161A, L178F, A179T, G223L, S229P,
H272Q, G303E, H307L, A309P, S334P relative to wild type non-
maltogenic exoamylase.
MDQAGKSPAGVRYHGGDEIILQGFHWNVVREAPYNWYNILRQQASTIAADGFSAIWMPVPWRDFSSWT
DGGKSGGGEGYFWHDFNKNGRYGSDAQLRQAAGALGGAGVKVLYDVVPNHMNRFYPDKEINLPAGQRF
WRNDCPDPGNGPNDCDDGDRFLGGEADLNTGHPQIYGMFRDEFTNLRSGYGAGGFRFDFVRGYAPERV
DSWMSDSADSSFCVGELWKEPSEYPPWDWRNTASWQQIIKDWSDRAKCPVFDFALKERMQNGSVADWK
QGLNGNPDPRWREVAVTFVDNHDTGYSPGQNEGQHLWPLQDGLIRQAYAYILTSPGTPVVYWPHMYDW
GYGDFIRQLIQVRRTAGVRADSAISFHSGYSGLVATVSGSQQTLVVALNSDLANPGQVASGSFSEAVN
ASNGQVRVWRSGSGDGGGNDGG- SEQ ID NO: 14
pSac-pMD229 sequence; *Pseudomonas saccharophila* maltotetrahydrolase
nucleotide sequence with 17 substitutions and deletion of the starch
binding domain.
```
   1 atggatcagg ccggcaagag cccggccggg gtgcgctacc acggcggcga cgaaatcatc
  61 ctccagggct ccactggaa cgtcgtccgc gaagcgccct acaactggta caacatcctc
 121 cgccaacagg cctcgacgat cgcggccgac ggcttctcgg caatctggat gccagtgccc
 181 tggcgtgact ctccagctg gaccgacggc ggcaagtccg gcggcggcga aggctacttc
 241 tggcacgact tcaacaagaa cggccgctac ggcagcgacg cccagctgcg ccaggccgcc
 301 ggcgcactcg gtggcgccgg ggtgaaggtg ctctacgatg tggtgcccaa tcacatgaac
 361 cgcttctacc cggacaagga gatcaacctg ccggccggcc agcgcttctg gcgcaacgac
 421 tgcccggatc cgggcaacgg ccccaacgac tgcgacgacg gtgaccgctt cctgggcggc
 481 gaggcggacc tgaacaccgg ccatccgcag atttacggca tgtttcgcga cgagtttacc
 541 aacctgcgca gccggctacgg cgccggcggc ttccgcttcg acttcgttcg cggctatgcg
 601 cccgagcggg tcgacagctg gatgagcgac agcgccgaca gcagcttctg cgttggcgag
 661 ctgtggaaag agccttctga atatccgccc tgggactggc gcaacaccgc gagctggcag
 721 cagatcatca aggactggtc cgaccgggcc aagtgcccgg tgttcgactt cgctctcaag
 781 gagcgcatgc agaacggctc ggtcgccgac tggaagcagg gcctcaatgg caaccccgac
 841 ccgcgctggc gcgaggtggc ggtgaccttc gtcgacaacc acgacaccgg ctattcgccc
 901 gggcagaacg aaggccagca cctgtggccg ctgcaggacg gctgatccg ccaggcctac
 961 gcctacatcc tcaccagccc gggcacgccg gtggtgtact ggccgcacat gtacgactgg
1021 ggctacggcg acttcatccg ccagctgatc caggtgcgc gcaccgccgg cgtgcgcgcc
1081 gattcggcga tcagcttcca tagcggctac agcggtctgg tcgctaccgt cagcggcagc
1141 cagcagaccc tggtggtggc gctcaactcc gatctggcca accccggcca ggttgccagc
1201 ggcagcttca gcgaggcggt caacgccagc aacggccagg tgcgcgtctg gcgcagcggt
1261 agcggcgatg gcggcgggaa tgacggcggc tga
```

SEQ ID NO: 15
pSac-pMD248 sequence; *Pseudomonas saccharophila* maltotetrahydrolase
amino acid sequence with 16 substitutions and deletion of the starch
binding domain.

-continued

MDQAGKSPAGVRYHGGDEIILQGFHWNVVREAPYNWYNILRQQASTIAADGFSAIWMPVPWRDFSSWT
DGGKSGGGEGYFWHDFNKNGRYGSDAQLRQAAGALGGAGVKVLYDVVPNHMNRFYPDKEINLPAGQRF
WRNDCPDPGDGPNDCDDGDRFLGGESDLNTGHPQIYGMFRDEFTNLRSGYGAGGFRFDFVRGYAPERV
DSWMSDSADSSFCVGELWKEPSEYPPWDWRNTASWQQIIKDWSDRAKCPVFDFALKERMQNGSVADWK
QGLNGNPDPRWREVAVTFVDNHDTGYSPGQNEGQHLWALQDGLIRQAYAYILTSPGTPVVYWPHMYDW
GYGDFIRQLIQVRRTAGVRADSAISFHSGYSGLVATVSGSQQTLVVALNSDLANPGQVASGSFSEAVN
ASNGQVRVWRSGSGDGGGNDGG

SEQ ID NO: 16
pSac-pMD248 sequence; *Pseudomonas saccharophila* maltotetrahydrolase
nucleotide sequence with 16 substitutions and deletion of the starch
binding domain.
```
   1 atggatcagg ccggcaagag cccggccggg gtgcgctacc acggcggcga cgaaatcatc
  61 ctccagggct ccactggaa cgtcgtccgc gaagcgccct acaactggta caacatcctc
 121 cgccaacagg cctcgacgat cgcggccgac ggcttctcgg caatctggat gccagtgccc
 181 tggcgtgact tctccagctg gaccgacggc ggcaagtccg gcggcggcga aggctacttc
 241 tggcacgact tcaacaagaa cggccgctac ggcagcgacg cccagctgcg ccaggccgcc
 301 ggcgcactcg gtggcgccgg ggtgaaggtg tctctacgatg tggtgcccaa tcacatgaac
 361 cgcttctacc cggacaagga gatcaacctg ccggccggcc agcgcttctg cgcaacgac
 421 tgcccgacc cgggcgacgg ccccaacgac tgcgacgacg gtgaccgctt cctgggcggc
 481 gagtcggacc tgaacaccgg ccatccgcag atttacggca tgtttcgcga cgagtttacc
 541 aacctgcgca gcggctacgg cgccggcggc ttccgcttcg acttcgttcg cggctatgcg
 601 cccgagcggg tcgacagctg gatgagcgac agcgccgaca gcagcttctg cgttggcgag
 661 ctgtggaaag agccttctga atatccgccg tgggactggc gcaacacggc gagctggcag
 721 cagatcatca aggactggtc cgaccgggcc aagtgcccgg tgttcgactt cgctctcaag
 781 gagcgcatgc agaacggctc ggtcgccgac tggaagcagg gcctcaatgg caacccgac
 841 ccgcgctggc gcgaggtggc ggtgaccttc gtcgacaacc acgacaccgg ctattcgccc
 901 gggcagaacg aaggccagca cctgtgggcg ctgcaggacg gctgatccg ccaggcctac
 961 gcctacatcc tcaccagccc gggcacgccg gtggtgtact ggccgcacat gtacgactgg
1021 ggctacggcg acttcatccg ccagctgatc caggtcggc gcaccgccgg cgtgcgcgcc
1081 gattcggcga tcagcttcca tagcggctac agcggtctgg tcgctaccgt cagcggcagc
1141 cagcagaccc tggtggtggc gctcaactcc gatctggcca accccggcca ggttgccagc
1201 ggcagcttca gcgaggcggt caacgccagc aacggccagg tgcgcgtctg gcgcagcggt
1261 agcggcgatg gcggcgggaa tgacggcggc tga
```

SEQ ID NO: 17
pSac-pMD253 sequence; *Pseudomonas saccharophila* maltotetrahydrolase
amino acid sequence with 16 substitutions and deletion of the starch
binding domain.
MDQAGKSPAGVRYHGGDEIILQGFHWNVVREAPYNWYNILRQQASTIAADGFSAIWMPVPWRDFSSWT
DGGKSGGGEGYFWHDFNKNGRYGSDAQLRQAAGALGGAGVKVLYDVVPNHMNRDYPDKEINLPAGQRF
WRNDCPDPGNGPNDCDDGDRFLGGESDLNTGHPQIYGMFRDEFTNLRSGYGAGGFRFDFVRGYAPERV
DSWMSDSADSSFCVGELWKEPSEYPPWDWRNTASWQQIIKDWSDRAKCPVFDFALKERMQNGSVADWK
QGLNGNPDPRWREVAVTFVDNHDTGYSPGQNEGQHLWPLQDGLIRQAYAYILTSPGTPVVYWPHMYDW
GYGDFIRQLIQVRRTAGVRADSAISFHSGYSGLVATVSGSQQTLVVALNSDLANPGQVASGSFSEAVN
ASNGQVRVWRSGSGDGGGNDGG SEQ ID NO: 18
pSac-pMD253 sequence; *Pseudomonas saccharophila* maltotetrahydrolase
nucleotide sequence with 16 substitutions and deletion of the starch
binding domain.
```
   1 atggatcagg ccggcaagag cccggccggg gtgcgctacc acggcggcga cgaaatcatc
  61 ctccagggct ccactggaa cgtcgtccgc gaagcgccct acaactggta caacatcctc
 121 cgccaacagg cctcgacgat cgcggccgac ggcttctcgg caatctggat gccagtgccc
 181 tggcgtgact tctccagctg gaccgacggc ggcaagtccg gcggcggcga aggctacttc
 241 tggcacgact tcaacaagaa cggccgctac ggcagcgacg cccagctgcg ccaggccgcc
 301 ggcgcactcg gtggcgccgg ggtgaaggtg tctctacgatg tggtgcccaa tcacatgaac
 361 cgcgactacc cggacaagga gatcaacctg ccggccggcc agcgcttctg cgcaacgac
 421 tgcccgacc cgggcaacgg ccccaacgac tgcgacgacg gtgaccgctt cctgggcggc
 481 gagtcggacc tgaacaccgg ccatccgcag atttacggca tgtttcgcga cgagtttacc
 541 aacctgcgca gcggctacgg cgccggcggc ttccgcttcg acttcgttcg cggctatgcg
 601 cccgagcggg tcgacagctg gatgagcgac agcgccgaca gcagcttctg cgttggcgag
 661 ctgtggaaag agccttctga atatccgccg tgggactggc gcaacacggc gagctggcag
 721 cagatcatca aggactggtc cgaccgggcc aagtgcccgg tgttcgactt cgctctcaag
 781 gagcgcatgc agaacggctc ggtcgccgac tggaagcagg gcctcaatgg caacccgac
 841 ccgcgctggc gcgaggtggc ggtgaccttc gtcgacaacc acgacaccgg ctattcgccc
 901 gggcagaacg aaggccagca cctgtgggcg ctgcaggacg gctgatccg ccaggcctac
 961 gcctacatcc tcaccagccc gggcacgccg gtggtgtact ggccgcacat gtacgactgg
1021 ggctacggcg acttcatccg ccagctgatc caggtcggc gcaccgccgg cgtgcgcgcc
1081 gattcggcga tcagcttcca tagcggctac agcggtctgg tcgctaccgt cagcggcagc
1141 cagcagaccc tggtggtggc gctcaactcc gatctggcca accccggcca ggttgccagc
1201 ggcagcttca gcgaggcggt caacgccagc aacggccagg tgcgcgtctg gcgcagcggt
1261 agcggcgatg gcggcgggaa tgacggcggc tga
```

SEQ ID NO: 19
pSac-pMD271 sequence; *Pseudomonas saccharophila* maltotetrahydrolase
amino acid sequence with 18 substitutions and deletion of the starch
binding domain.
MDQSGKSPAGVRYHGGDEIILQGFHWNVVREAPYNWYNILRQQASTIAADGFSAIWMPVPWRDFSSWT
DGDKSGGGEGYFWHDFNKNGRYGSDAQLRQAAGALGGAGVKVLYDVVPNHMNRDYPDKEINLPAGQRF
WRNDCPDPGNGPNDCDDGDRFLGGESDLNTGHPQIYGMFRDEFTNLRSGYGAGGFRFDFVRGYAPERV -continued DSWMSDSADSSFCVGELWKEPSEYPPWDWRNTASWQQIIKDWSDRAKCPVFDFALKERMQNGSVADWK
QGLNGNPDPRWREVAVTFVDNHDTGYSPGQNEGQHLWPLQDGLIRQAYAYILTSPGTPVVYWPHMYDW
GYGDFIRQLIQVRRTAGVRADSAISFHSGYSGLVATVSGSQQTLVVALNSDLANPGQVASGSFSEAVN
ASNGQVRVWRSGSGDGGNDGG SEQ ID NO: 20
pSac-pMD271 sequence; *Pseudomonas saccharophila* maltotetrahydrolase
nucleotide sequence with 18 substitutions and deletion of the starch
binding domain.

```
   1 atggatcaga gcggcaagag cccggccggg gtgcgctacc acggcggcga cgaaatcatc
  61 ctccagggct tccactggaa cgtcgtccgc gaagcgccct acaactggta caacatcctc
 121 cgccaacagg cctcgacgat cgcggccgac ggcttctcgg caatctggat gccagtgccc
 181 tggcgtgact tctccagctg gaccgacggc gacaagtccg gcggcggcga aggctacttc
 241 tggcacgact tcaacaagaa cggccgctac cccagctgcg ccagccgcc
 301 ggcgcactcg gtggcgccgg ggtgaaggtg ctctacgatg tggtgcccaa tcacatgaac
 361 cgcgactacc cggacaagga gatcaacctg ccggccggcc agcgcttctg gcgcaacgac
 421 tgcccggacc cgggcaacgg ccccaacgac tgcgacgacg gtgaccgctt cctgggcggc
 481 gagtcggacc tgaacaccgg ccatccgcag atttacggca tgtttcgcga cgagtttacc
 541 aacctgcgca gcggctacgg cgccggcggc ttccgcttcg acttcgttcg cggctatgcg
 601 cccgagcggg tcgacagctg gatgagcgac agcgccgaca gcagcttctg cgttggcgag
 661 ctgtggaaag agccttctga atatccgccc tgggactggc gcaacaccgg cagctggcag
 721 cagatcatca aggactggtc cgaccggccc aagtgcccgg tgttcgactt cgctctcaag
 781 gagcgcatgc agaacggctc ggtcgccgac tggaagcagg gcctcaatgg caaccccgac
 841 ccgcgctggc gcgaggtggc ggtgaccttc gtcgacaacc acgacaccgg ctattcgccc
 901 gggcagaacg aaggccagca cctgtggccc ctgcaggacg gcctgatccg ccaggcctac
 961 gcctacatcc tcaccagccc gggcacgccg gtggtgtact ggccgcacat gtacgactgg
1021 ggctacggcg acttcatccg ccagctgatc caggtgcggc gcaccgccgg cgtgcgcgcc
1081 gattcggcga tcagcttcca tagcggctac agcggtctgg tcgctaccgt cagcggcagc
1141 cagcagaccc tggtggtggc gctcaactcc gatctggcca accccggcca ggttgccagc
1201 ggcagcttca gcgaggcggt caacgccagc aacggccagg tgcgcgtctg gcgcagcggt
1261 agcggcgatg gcggcgggaa tgacggcggc tga
```

---

What is claimed is:

1. A non-naturally occurring polypeptide having an amino acid sequence, which with reference to the position numbering of a *Pseudomonas saccharophila* exoamylase sequence shown as SEQ ID NO: 1, the amino acid sequence comprises a mutation independently selected from the group consisting of: 33Y, 34N, 121F, 134R, 141P, 146G, 157L, 161A, 178F, 179T, 223E, 229P, 272Q, 303E, 307L, 309P and 334P;

wherein the polypeptide has non-maltogenic exoamylase activity.

2. The polypeptide according to claim 1, in which each of the amino acid mutations are independently selected from the group consisting of: N33Y, D34N, G121F, G134R, A141P, Y146G, I157L, S161A, L178F, A179T, G223E, S229P, H272Q, G303E, H307L, A309P and S334P.

3. The polypeptide according to claim 2, which comprises the sequence pSac-pMD229 (SEQ ID NO: 13).

4. The polypeptide according to claim 1, wherein the polypeptide is prepared from a *Pseudomonas* parent polypeptide having exoamylase activity.

5. The polypeptide according to claim 4, wherein the *Pseudomonas* parent polypeptide is from *Pseudomonas saccharophila* or *Pseudomonas stutzeri*.

6. The polypeptide according to claim 5, wherein the *Pseudomonas* parent polypeptide is a non-maltogenic exoamylase from *Pseudomonas saccharophila* having a sequence shown as SEQ ID NO: 1.

7. The polypeptide according to claim 1 wherein the polypeptide has a higher thermostability compared to a *Pseudomonas* parent polypeptide from which the polypeptide can be prepared or a wild type *Pseudomonas* polypeptide when tested under the same conditions.

8. The polypeptide according to claim 7, wherein the half life (t½), at 60 degrees C., is increased by 15% or more relative to the *Pseudomonas* parent polypeptide or the wild type *Pseudomonas* polypeptide.

9. The polypeptide according to claim 1, wherein the polypeptide has a higher exo-specificity compared to a *Pseudomonas* parent polypeptide from which the polypeptide can be prepared or a wild type *Pseudomonas* polypeptide when tested under the same conditions.

10. The polypeptide according to claim 9, wherein the polypeptide has 10% or more exo-specificity compared to the *Pseudomonas* parent polypeptide or the wild type *Pseudomonas* polypeptide.

11. The polypeptide according to claim 1, wherein a food product treated with the polypeptide has any one or more of the following properties: (a) lower firmness; (b) higher resilience; and (c) higher cohesiveness compared to a food product which has been treated with a *Pseudomonas* parent polypeptide from which the polypeptide can be prepared or a wild type *Pseudomonas* polypeptide.

12. The polypeptide according to claim 11, wherein the resilience or cohesiveness of the food product treated with the polypeptide is independently increased by 15% or more relative to the food product which has been treated with the *Pseudomonas* parent polypeptide or the wild type *Pseudomonas* polypeptide.

13. The polypeptide according to claim 12, wherein each of resilience and cohesiveness of the food product treated with the polypeptide is increased compared to the food product which has been treated with the *Pseudomonas* parent polypeptide or the wild type *Pseudomonas* polypeptide.

14. The polypeptide according to claim 11, wherein the firmness of the food product treated with the polypeptide is independently decreased by 15% or more relative to the food product which has been treated with the *Pseudomonas* parent polypeptide or the wild type *Pseudomonas* polypeptide.

15. The polypeptide according to claim 1, wherein the polypeptide has a higher thermostability or a higher exo-specificity, or both, compared to a *Pseudomonas* parent polypeptide from which the polypeptide can be prepared or a wild type *Pseudomonas* polypeptide, or wherein a food product treated with the polypeptide has any one or more of the following properties: (a) lower firmness; (b) higher resilience; or (c) higher cohesiveness as compared to a food product which has been treated with the *Pseudomonas* parent polypeptide or the wild type *Pseudomonas* polypeptide.

16. The polypeptide according to claim 1, wherein the polypeptide has a higher thermostability or a higher exo-specificity, or both, compared to a *Pseudomonas* parent polypeptide from which the polypeptide can be prepared or a wild type *Pseudomonas* polypeptide.

17. The polypeptide according to claim 16 having an amino acid sequence which is at least 95% identical to SEQ ID NO: 13.

18. A non-naturally occurring polypeptide having an amino acid sequence of amino acids 1-429 of SEQ ID NO: 1, which with reference to the position numbering of a *Pseudomonas saccharophila* exoamylase sequence shown as SEQ ID NO: 1, the amino acid sequence comprises a mutation:

(a) independently selected from the group consisting of: 33Y, 34N, 121F, 134R, 141P, 146G, 157L, 161A, 178F, 179T, 223E, 229P, 272Q, 303E, 307L, 309P and 334P, preferably N33Y, D34N, G121F, G134R, A141P, Y146G, I157L, S161A, L178F, A179T, G223E, S229P, H272Q, G303E, H307L, A309P and S334P or (b) independently selected from the group consisting of: 33Y, 34N, 121F, 134R, 141P, 145D, 146G, 157L, 178F, 179T, 223E, 229P, 272Q, 303E, 307L and 334P, preferably N33Y, D34N, G121F, G134R, A141P, N145D, Y146G, I157L, L178F, A179T, G223E, S229P, H272Q, G303E, H307L and S334P or (c) independently selected from the group consisting of: 33Y, 34N, 121D, 134R, 141P, 146G, 157L, 178F, 179T, 223E, 229P, 272Q, 303E, 307L, 309P and 334P, preferably N33Y, D34N, G121D, G134R, A141P, Y146G, I157L, L178F, A179T, G223E, S229P, H272Q, G303E, H307L, A309P and S334P or (d) independently selected from the group consisting of: 3S, 33Y, 34N, 70D, 121D, 134R, 141P, 146G, 157L, 178F, 179T, 223E, 229P, 272Q, 303E, 307L, 309P and 334P, preferably A3S, N33Y, D34N, G70D, G121D, G134R, A141P, Y146G, I157L, L178F, A179T, G223E, S229P, H272Q, G303E, H307L, A309P and S334P;

wherein the polypeptide has non-maltogenic exoamylase activity.

19. The polypeptide according to claim 4, wherein the *Pseudomonas* parent polypeptide is a non-maltogenic exoamylase.

20. The polypeptide according to claim 19, wherein the *Pseudomonas* parent polypeptide is a glucan 1,4-alpha-maltotetrahydrolase (EC 3.2.1.60).

21. The polypeptide according to claim 8, wherein the half life (t½), at 60 degrees C., is increased by 50% or more relative to the *Pseudomonas* parent polypeptide or the wild type *Pseudomonas* polypeptide.

22. The polypeptide according to claim 21, wherein the half life (t½), at 60 degrees C., is increased by 100% or more relative to the *Pseudomonas* parent polypeptide or the wild type *Pseudomonas* polypeptide.

23. The polypeptide according to claim 10, wherein the polypeptide has 20% or more exo-specificity compared to the *Pseudomonas* parent polypeptide or the wild type *Pseudomonas* polypeptide.

24. The polypeptide according to claim 23, wherein the polypeptide has 50% or more exo-specificity compared to the *Pseudomonas* parent polypeptide or the wild type *Pseudomonas* polypeptide.

25. The polypeptide according to claim 11, wherein the food product treated with the polypeptide has all of the following properties: (a) lower firmness; (b) higher resilience; and (c) higher cohesiveness compared to the food product which has been treated with the parent *Pseudomonas* polypeptide or the wild type *Pseudomonas* polypeptide.

26. The polypeptide according to claim 12, wherein the resilience or cohesiveness of the food product treated with the polypeptide is independently increased by 50% or more relative to the food product which has been treated with the *Pseudomonas* parent polypeptide or the wild type *Pseudomonas* polypeptide.

27. The polypeptide according to claim 26, wherein the resilience or cohesiveness of the food product treated with the polypeptide is independently increased by 100% or more relative to the food product which has been treated with the *Pseudomonas* parent polypeptide or the wild type *Pseudomonas* polypeptide.

28. The polypeptide according to claim 14, wherein the firmness of the food product treated with the polypeptide is independently decreased by 50% or more relative to the food product which has been treated with the *Pseudomonas* parent polypeptide or the wild type *Pseudomonas* polypeptide.

29. The polypeptide according to claim 28, wherein the firmness of the food product treated with the polypeptide is independently decreased by 100% or more relative to the food product which has been treated with the *Pseudomonas* parent polypeptide or the wild type *Pseudomonas* polypeptide.

30. The polypeptide according to claim 15, wherein the polypeptide has a higher thermostability or a higher exo-specificity, or both, compared to the *Pseudomonas* parent polypeptide from which the polypeptide can be prepared or the wild type *Pseudomonas* polypeptide, or wherein the food product treated with the polypeptide has all of the following properties: (a) lower firmness; (b) higher resilience; or (c) higher cohesiveness as compared to the food product which has been treated with the *Pseudomonas* parent polypeptide or the wild type *Pseudomonas* polypeptide.

* * * * *